United States Patent [19]
Kilama

[11] Patent Number: 5,643,855
[45] Date of Patent: Jul. 1, 1997

[54] HERBICIDAL IMIDAZOLONES

[75] Inventor: John Jolly Kilama, Wilmington, Del.

[73] Assignee: E. I. Du Pont de Nemours and Company, Wilmington, Del.

[21] Appl. No.: 454,155

[22] PCT Filed: Dec. 7, 1993

[86] PCT No.: PCT/US93/11636

§ 371 Date: Jun. 15, 1995

§ 102(e) Date: Jun. 15, 1995

[87] PCT Pub. No.: WO94/14817

PCT Pub. Date: Jul. 7, 1994

Related U.S. Application Data

[63] Continuation-in-part of Ser. No. 109,875, Aug. 20, 1993, abandoned, which is a continuation-in-part of Ser. No. 96,526, Jul. 22, 1993, abandoned, which is a continuation-in-part of Ser. No. 73,010, Jun. 4, 1993, abandoned, which is a continuation-in-part of Ser. No. 992,880, Dec. 21, 1992, abandoned.

[51] Int. Cl.$^6$ ............. C07D 471/04; C07D 235/02; C07D 498/04; C07D 487/04; A01N 43/90; A01N 43/50

[52] U.S. Cl. ............. 504/224; 504/241; 504/246; 504/249; 504/266; 504/276; 504/277; 504/278; 504/279; 504/222; 504/225; 504/235; 544/48; 544/105; 544/281; 544/350; 544/139; 546/128; 546/199; 548/126; 548/302.9; 548/316.4; 548/317.1; 548/323.1; 548/323.5; 548/324.1; 548/324.5; 548/325.5; 548/322.5

[58] Field of Search ............. 544/105, 139, 544/48, 281, 350; 546/199, 121; 504/225, 249, 276, 222, 224, 235, 241, 246, 266, 277, 278, 279; 548/302.7, 126, 316.4, 317.1, 322.7, 323.1, 323.5, 324.1, 324.5, 325.5

[56] References Cited

U.S. PATENT DOCUMENTS 3,284,447  11/1966  Kusuda ............. 260/239.9

(List continued on next page.)

FOREIGN PATENT DOCUMENTS 0068822  1/1983  European Pat. Off. ..

(List continued on next page.)

OTHER PUBLICATIONS

Weinreb et al, *Tetrahedron Letters*, 4171–4174 (1977).

(List continued on next page.)

Primary Examiner—Patricia I. Morris

[57] ABSTRACT

Compounds such as Formula I having herbicidal utility are disclosed:

wherein
Q is $R_1$ is H; alkyl, haloalkyl or halogen $R^2$ is $C_1$–$C_2$alkyl optionally substituted with one or more halogens, $OR^8$, CN, $COR^9$, $CO_2R^{31}$ or $CONR^{32}R^{33}$; CN; $CO_2R^{34}$; $CONR^{35}R^{36}$; $S(O)_nR^8$; $S(O)_nNR^{19}R^8$ or $COR^{37}$; or $R^1$ and $R^2$ can be taken together along with the carbon to which they are attached to form $C=CHCO_2R^{31}$; $C=(CH_3)CO_2R^{31}$; $C=(C_2H_5)CO_2R^{31}$; $C=CHCONR^{32}R^{33}$; $C=C(CH_3)CONR^{32}R^{33}$ or $C=C(C_2H_5)CONR^{32}R^{33}$.

5 Claims, No Drawings

U.S. PATENT DOCUMENTS

| | | | |
|---|---|---|---|
| 3,442,892 | 5/1969 | Kusuda | 260/2.4 |
| 4,531,964 | 7/1985 | Shimano et al. | 71/92 |
| 4,902,335 | 2/1990 | Kume et al. | 71/90 |
| 5,053,071 | 10/1991 | Semple | 71/92 |

FOREIGN PATENT DOCUMENTS

| | | |
|---|---|---|
| 46-16990 | 5/1971 | Japan . |
| 8802143 | 6/1988 | Spain . |
| 1114397 | 5/1968 | United Kingdom . |

OTHER PUBLICATIONS

Fischer, R. et al, *Chemical Abstracts*, 113, p. 705, Abstract No. 59178u (1990).

Hoffman–LaRoche, *Chemical Abstracts*, 69, p. 5545, Abstract No. 59272t (1968).

HERBICIDAL IMIDAZOLONES

This application is a 371 of PCT/US93/11636 filed Dec. 7, 1993 which is a continuation-in-part of U.S. Ser. No. 08/109,875 filed Aug. 20, 1993 now abandoned, which is a continuation-in-part of U.S. Ser. No. 08/096,526 filed Jul. 22, 1993 now abandoned, which is a continuation-in-part of U.S. Ser. No. 08/073,010 filed Jun. 4, 1993 now abandoned, which is a continuation-in-part of U.S. Ser. No. 07/992,880 filed Dec. 21, 1992 now abandoned.

This invention comprises novel imidazolones and their agriculturally suitable salts for weed control in crops. This invention further comprises a simple one-pot procedure for preparing amino amides from the corresponding α-amino acid, ester or lactone, a trialkylaluminum and an amine, the reaction proceeding with retention of configuration and without the need for prior protection of the α-amino moiety.

Certain related imidazolidinone derivatives with analgesic, anti-inflammatory and antipyretic activities are disclosed in U.S. Pat. No. 3,442,892 as pharmaceuticals. The imidazolones of the present invention are not disclosed therein.

A general method for the conversion of esters to amides by reaction of an aluminum amide with an ester has been described, see for example, Weinreb et al., *Tetrahedron Lett.*, (1977), 4171–4174. Weinreb et al. discloses the amidation of a protected N-acetyl amino acid, however, no mention is made of unprotected amino acids or peptides or the retention or loss of configuration at the carbon bearing the amino moiety. Numerous prior art methods are known for the amidation of protected α-amino acids or esters, however, the prior art does not disclose the direct amidation of unprotected α-amino acids or esters without substantial concomitant racemization when the α-amino acids or esters are enantiomerically enriched.

The present invention demonstrates an advance over the prior art by the direct synthesis of α-amino amides from the corresponding α-amino acids, esters or lactones, without prior protection of the amino group and with retention of configuration at the carbon bearing the α-amino group. A specific application of the method of the present invention is the synthesis of peptides.

SUMMARY OF THE INVENTION

The compounds of this invention are compounds of the formula:

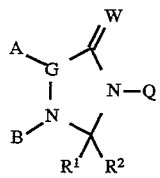

wherein

Q is

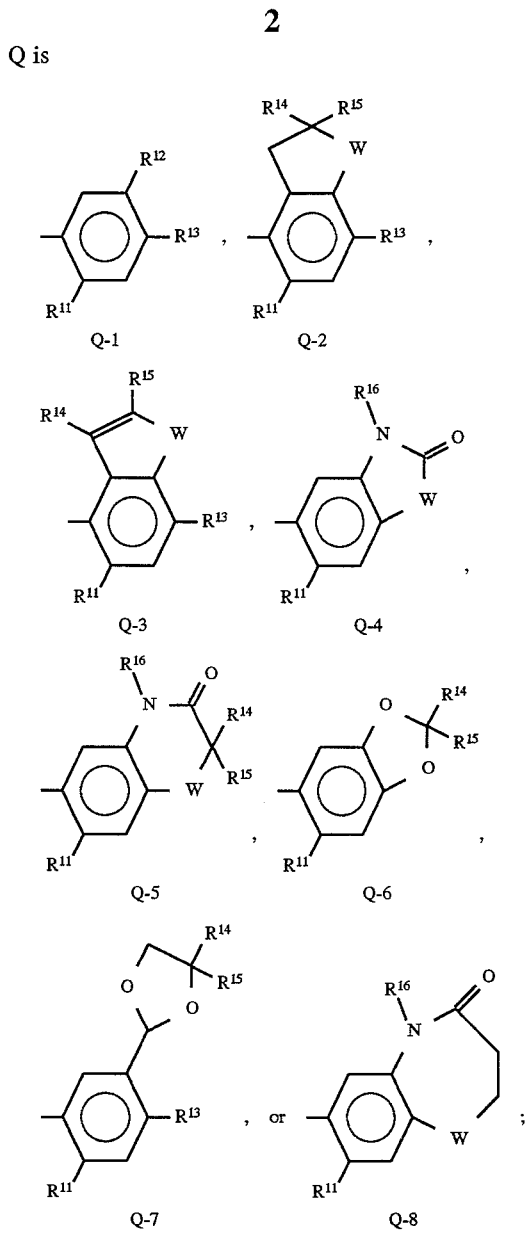

$R^1$ is H; $C_1$–$C_4$ alkyl, $C_1$–$C_4$ haloalkyl; or halogen;

$R^2$ is $C_1$–$C_2$ alkyl optionally substituted with one or more halogens, $OR^8$, CN, $COR^9$, $CO_2R^{31}$ or $CONR^{32}R^{33}$; CN; $CO_2R^{34}$; $CONR^{35}R^{36}$; $S(O)_nR^8$; $S(O)_nNR^{19}R^8$ or $COR^{37}$; or $R^1$ and $R^2$ can be taken together along with the carbon to which they are attached to form $C=CHCO_2R^{31}$; $C=C(CH_3)CO_2R^{31}$; $C=C(C_2H_5)CO_2R^{31}$; $C=CHCONR^{32}R^{33}$; $C=C(CH_3)CONR^{32}R^{33}$ or $C=C(C_2H_5)CONR^{32}R^{33}$;

G is CH; C($C_1$–$C_4$ alkyl); or N;

A is $C_1$–$C_4$ alkyl; $C_1$–$C_4$ haloalkyl; $C_2$–$C_4$ alkenyl; $C_2$–$C_4$ alkynyl; $OR^{10}$; $SR^{10}$ or halogen;

B is $C_1$–$C_4$ alkyl; $C_1$–$C_4$ haloalkyl; $C_3$–$C_4$ alkenyl or $C_3$–$C_4$ alkynyl;

A and B can be taken together as X–Y–Z to form a fused ring such that X is connected to nitrogen and Z is connected to G;

X is $CHR^3$; $CHR^4CHR^5$; $CR^4=CR^5$;

Y is $CHR^6$; $CR^6=CR^6$; $NR^{38}$; O or $S(O)_n$;

Z is CHR$^7$; CHR$^4$CHR$^5$; CR$^4$=CR$^5$; NR$^{38}$O; or S(O)$_n$;

n is independently 0; 1 or 2;

R$^3$, R$^4$, R$^5$, R$^6$ and R$^7$ are independently H; halogen; C$_1$–C$_4$ alkyl or C$_1$–C$_4$ haloalkyl; or R$^3$ and R$^6$, or R$^6$ and R$^7$, can be taken together to form —CH$_2$—;

R$^8$ and R$^9$ are independently H; C$_1$–C$_6$ alkyl; C$_2$–C$_6$ alkenyl; C$_3$–C$_6$ cycloalkyl or phenyl optionally substituted with one or more CH$_3$, OCH$_3$, NO$_2$, CN or halogens;

W is independently O or S;

R$^{10}$ is C$_1$–C$_4$ alkyl or C$_1$–C$_4$ haloalkyl;

R$^{11}$ is halogen;

R$^{12}$ is H; C$_1$–C$_8$ alkyl; C$_1$–C$_8$ haloalkyl; halogen; OH; OR$^{17}$; SH; S(O)$_n$R$^{17}$; COR$^{17}$; CO$_2$R$^{17}$; C(O)SR$^{17}$; C(O)NR$^{19}$R$^{20}$; CHO; CR$^{19}$=NOR$^{26}$; CH=CR$^{27}$CO$_2$R$^{17}$; CH$_2$CHR$^{27}$CO$_2$R$^{17}$; CO$_2$N=CR$^{21}$R$^{22}$; NO$_2$; CN; NHSO$_2$R$^{23}$; NHSO$_2$NHR$^{23}$; NR$^{17}$R$^{28}$; NH$_2$ or phenyl optionally substituted with R$^{29}$;

R$^{13}$ is C$_1$–C$_2$ alkyl; C$_1$–C$_2$ haloalkyl; OCH$_3$; SCH$_3$; OCHF$_2$; halogen; CN or NO$_2$;

R$^{14}$ is H; C$_1$–C$_3$ alkyl or halogen;

R$^{15}$ is H; C$_1$–C$_3$ alkyl; halogen; C$_1$–C$_3$ haloalkyl; cyclopropyl; vinyl; C$_2$ alkynyl; CN; C(O)R$^{28}$; CO$_2$R$^{28}$; C(O)NR$^{28}$R$^{30}$; CR$^{24}$R$^{25}$CN; CR$^{24}$R$^{25}$C(O)R$^{28}$; CR$^{24}$R$^{25}$CO$_2$R$^{28}$; CR$^{24}$R$^{25}$C(O)NR$^{28}$R$^{30}$; CHR$^{24}$OH; CHR$^{24}$OC(O)R$^{28}$ or OCHR$^{24}$OC(O)NR$^{28}$R$^{30}$; or when Q is Q-2 or Q-6, R$^{14}$ and R$^{15}$ can be taken together with the carbon to which they are attached to form C=O;

R$^{16}$ is H; C$_1$–C$_6$ alkyl; C$_1$–C$_6$ haloalkyl; C$_2$–C$_6$ alkoxyalkyl; C$_3$–C$_6$ alkenyl;

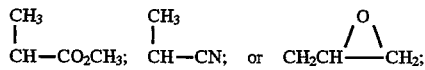

C$_3$–C$_6$ alkynyl;

R$^{17}$ is C$_1$–C$_8$ alkyl; C$_3$–C$_8$ cycloalkyl; C$_3$–C$_8$ alkenyl; C$_3$–C$_8$ alkynyl; C$_1$–C$_8$ haloalkyl; C$_2$–C$_8$ alkoxyalkyl; C$_2$–C$_8$ alkylthioalkyl; C$_2$–C$_8$ alkylsulfinylalkyl; C$_2$–C$_8$ alkylsulfonylalkyl; C$_4$–C$_8$ alkoxyalkoxyalkyl; C$_4$–C$_8$ cycloalkylalkyl; C$_6$–C$_8$ cycloalkoxyalkyl; C$_4$–C$_8$ alkenyloxyalkyl; C$_4$–C$_8$ alkynyloxyalkyl; C$_3$–C$_8$ haloalkoxyalkyl; C$_4$–C$_8$ haloalkenyloxyalkyl; C$_4$–C$_8$ haloalkynyloxyalkyl; C$_6$–C$_8$ cycloalkylthioalkyl; C$_4$–C$_8$ alkenylthioalkyl; C$_4$–C$_8$ alkynylthioalkyl; C$_1$–C$_4$ alkyl substituted with phenoxy or benzyloxy, each ring optionally substituted with halogen, C$_1$–C$_3$ alkyl or C$_1$–C$_3$ haloalkyl; C$_4$–C$_8$ trialkylsilylalkyl; C$_3$–C$_8$ cyanoalkyl; C$_3$–C$_8$ halocycloalkyl; C$_3$–C$_8$ haloalkenyl; C$_5$–C$_8$ alkoxyalkenyl; C$_5$–C$_8$ haloalkoxyalkenyl; C$_5$–C$_8$ alkylthioalkenyl; C$_3$–C$_8$ haloalkynyl; C$_5$–C$_8$ alkoxyalkynyl; C$_5$–C$_8$ haloalkoxyalkynyl; C$_5$–C$_8$ alkylthioalkynyl; C$_2$–C$_8$ alkyl carbonyl; benzyl optionally substituted with halogen, C$_1$–C$_3$ alkyl or C$_1$–C$_3$ haloalkyl; CHR$^{24}$COR$^{18}$; CHR$^{24}$P(O)(OR$^{18}$)$_2$; CHR$^{24}$P(S)(OR$^{18}$)$_2$; CHR$^{24}$C(O)NR$^{19}$R$^{20}$; CHR$^{24}$C(O)NH$_2$; CHR$^{24}$CO$_2$R$^{18}$; CO$_2$R$^{18}$;

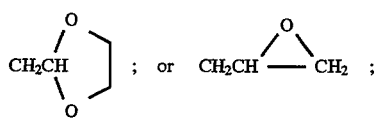

R$^{18}$ is C$_1$–C$_6$ alkyl; C$_1$–C$_6$ haloalkyl; C$_3$–C$_6$ alkenyl or C$_3$–C$_6$ alkynyl;

R$^{19}$ and R$^{21}$ are independently H or C$_1$–C$_4$ alkyl;

R$^{20}$ and R$^{22}$ are independently C$_1$–C$_4$ alkyl or phenyl optionally substituted with halogen, C$_1$–C$_3$ alkyl or C$_1$–C$_3$ haloalkyl;

R$^{19}$ and R$^{20}$ may be taken together along with the nitrogen to which they are attached to form a piperidinyl, pyrrolidinyl or morpholinyl ring, each ring optionally substituted with C$_1$–C$_3$ alkyl, phenyl or benzyl;

R$^{21}$ and R$^{22}$ may be taken together with the carbon to which they are attached to form C$_3$–C$_8$ cycloalkyl;

R$^{23}$ is C$_1$–C$_4$ alkyl or C$_1$C$_4$ haloalkyl;

R$^{24}$ and R$^{25}$ are independently H or C$_1$–C$_4$ alkyl;

R$^{26}$ is H, C$_1$–C$_6$ alkyl, C$_3$–C$_6$ alkenyl or C$_3$–C$_6$ alkynyl;

R$^{27}$ is H, C$_1$–C$_4$ alkyl or halogen;

R$^{28}$ and R$^{30}$ are independently H or C$_1$–C$_4$ alkyl; and

R$^{29}$ is C$_1$–C$_2$ alkyl; C$_1$–C$_2$ haloalkyl; OCH$_3$; SCH$_3$; OCHF$_2$; halogen; CN or NO$_2$;

R$^{31}$, R$^{32}$, R$^{33}$, R$^{34}$. R$^{35}$, R$^{36}$ and R$^{37}$ are independently H; C$_1$–C$_6$ alkyl; C$_2$–C$_6$ alkenyl; C$_3$–C$_6$ alkynyl; C$_3$–C$_6$ cycloalkyl; or benzyl or phenyl each optionally substituted on the phenyl ring with one or more CH$_3$, OCH$_3$, NO$_2$, CN or halogen;

R$^{38}$ is H; C$_1$–C$_4$ alkyl or C$_1$–C$_4$ haloalkyl;

and their corresponding N-oxides and agriculturally suitable salts provided that 1) the sum of atoms in the backbone of the moiety of the fused ring formed by X, Y and Z is no greater than 4;

2) only one of X, Y and Z can be other than a carbon containing link;

3) when G is N and A and B are taken together as X-Y-Z, then Z is CHR$^7$; CHR$^4$CHR$^5$; or CR$^4$=CR$^5$;

4) when Q is Q-1 and R$^2$ is methyl or ethyl, then A and B are taken together as X-Y-Z; and 5) when G is N, A is other than OR$^{10}$, SR$^{10}$, or halogen.

Another embodiment of the invention is an agriculturally suitable composition for controlling the growth of undesired vegetation comprising an effective amount of a compound of Formula I with the substituents as defined above.

A further embodiment of the invention is a method for controlling the growth of undesired vegetation which comprises applying to the locus to be protected an effective amount of a compound of Formula I with the substituents as defined above.

The present invention also involves a process for the preparation of an amino amide of Formula IX which comprises contacting an unprotected α-amino acid, ester or lactone of Formula XIII, with an amine of Formula X or a hydrogen halide salt thereof, and a trialkylaluminum reagent of Formula XI

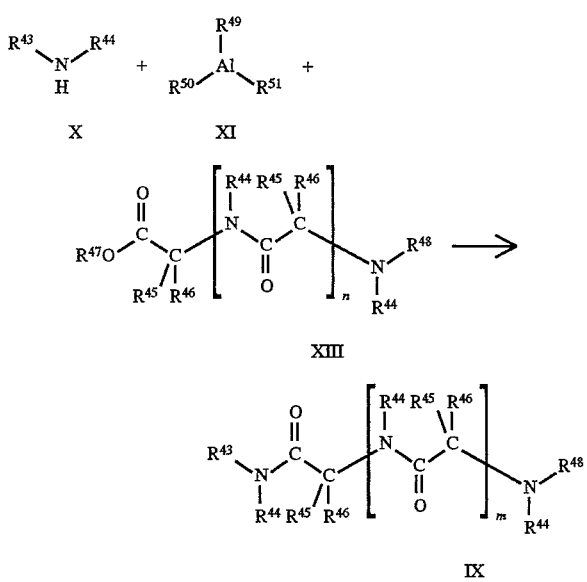

wherein:

$R^{43}$ is selected from the group H; $NH_2$; $C_2$–$C_{12}$ alkenyl; $C_1$–$C_{12}$ alkyl or $C_3$–$C_6$ cycloalkyl each optionally substituted with a substituent selected from the group morpholinyl, $C_1$–$C_6$ alkylamino, $C_2$–$C_6$ dialkylamino, pyridinyl and phenyl, each pyridinyl or phenyl optionally substituted with 1 to 3 substituents independently selected from the group halogen and $C_1$–$C_4$ alkyl; and a 5- or 6-membered monocyclic aromatic ring or 9- to 10-membered fused bicyclic aromatic ring each containing 0 to 3 heteroatoms independently selected from the group 0–2 O, 0–2 S, 0–4 N and 0–2 $NR^{52}$, each ring further optionally substituted with 1, 2 or 3 substituents independently selected from the group halogen, OH, $NO_2$, SH, CN, $C_1$–$C_6$ alkyl, $C_1$–$C_6$ alkylthio, $C_1$–$C_6$ alkylsulfonyl, $C_1$–$C_6$ alkoxy, $C_2$–$C_6$ alkenyloxy and $C_3$–$C_6$ alkynyloxy; provided that when $R^{44}$, $R^{45}$ or $R^{46}$ occur multiply in the same formula, each substituent is independently selected from the defined group;

$R^{44}$ is selected from the group H; $C_2$–$C_{12}$ alkenyl; $C_1$–$C_{12}$ alkyl or $C_3$–$C_6$ cycloalkyl each optionally substituted with a substituent selected from the group morpholinyl, $C_1$–$C_6$ alkylamino, $C_2$–$C_6$ dialkylamino, pyridinyl and phenyl, each pyridinyl or phenyl optionally substituted with 1 to 3 substituents independently selected from the group halogen and $C_1$–$C_4$ alkyl; and phenyl optionally substituted with 1 or 2 substituents independently selected from the group halogen and $C_1$–$C_6$ alkyl; or $R^{43}$ and $R^{44}$ are taken together to form a member selected from the group $-CH_2CH_2CH_2CH_2CH_2-$, $-CH_2CH_2CH_2CH_2-$ and $-CH_2CH_2CH_2-$;

$R^{45}$ is selected from the group H and $C_1$–$C_6$ alkyl;

$R^{46}$ is selected from the group H; $C_1$–$C_6$ alkoxy; $C_1$–$C_6$ haloalkyl; $C_1$–$C_{12}$ alkyl optionally substituted with a substituent selected from the group OH, $C_1$–$C_6$ alkoxy, SH, $C_1$–$C_6$ alkylthio, $C_1$–$C_6$ alkylsulfonyl, pyridinyl, phenyl, hydroxyphenyl, morpholinyl, amino, $C_1$–$C_6$alkylamino, $C_2$–$C_6$ dialkylamino, 3-indolyl, 4-imidazolyl, 1-methyl-4-imidazolyl, $C(=O)NH_2$, $C(=O)OH$, $NH(C=NH)NH_2$, and $C(=NH)NH_2$; and phenyl optionally substituted with 1 or 2 substituents independently selected from the group halogen and $C_1$–$C_6$ alkyl; or $R^{45}$ and $R^{46}$ are taken together to form a member selected from the group $-CH_2CH_2CH_2CH_2CH_2-$, $-CH_2CH_2CH_2CH_2-$ and $-CH_2CH_2CH_2-$; or $R^{46}$ and $R^{47}$ are taken together to form a member selected from the group $-CH_2CH_2CH_2CH_2-$, $-CH_2CH_2CH_2-$ and $-CH_2CH_2-$;

$R^{47}$ is selected from the group H, phenyl and $C_1$–$C_{12}$ alkyl; or $R^{44}$ and $R^{46}$ are taken together to form a member selected from the group $-CH_2CH_2CH_2CH_2-$, $-CH_2CH_2CH_2-$, $-CH_2CH_2-$, $-CH_2CH(OH)CH_2-$ and $-CH_2CH_2OCH_2-$;

$R^{48}$ is selected from the group H and $C_1$–$C_4$ alkyl; or $R^{44}$ and $R^{48}$ are taken together to form a member selected from the group $CH_2CH_2CH_2CH_2CH_2-$ and $-CH_2CH_2CH_2CH_2-$;

$R^{49}$, $R^{50}$ and $R^{51}$ are independently $C_1$–$C_6$ alkyl;

$R^{52}$ is selected from the group H and $C_1$–$C_6$ alkyl; and m is 0 or an integer from 1 to 5.

The reactants X, XI and XIII may be combined in any order to produce the desired amino amide of Formula IX. When m is other than 0, the process involves a method for converting the terminal carboxylic acid, ester and lactone of di- and polypeptides to the corresponding amide.

The present invention further involves a process for the preparation of one or both peptides of Formulae XV and XVI comprising contacting an unprotected. α-amino acid, ester or lactone of Formula XIV with a trialkylaluminum of Formula XI and an unprotected α-amino acid, ester or lactone of Formula XIIIa (compounds of Formula XIII wherein m is 0)

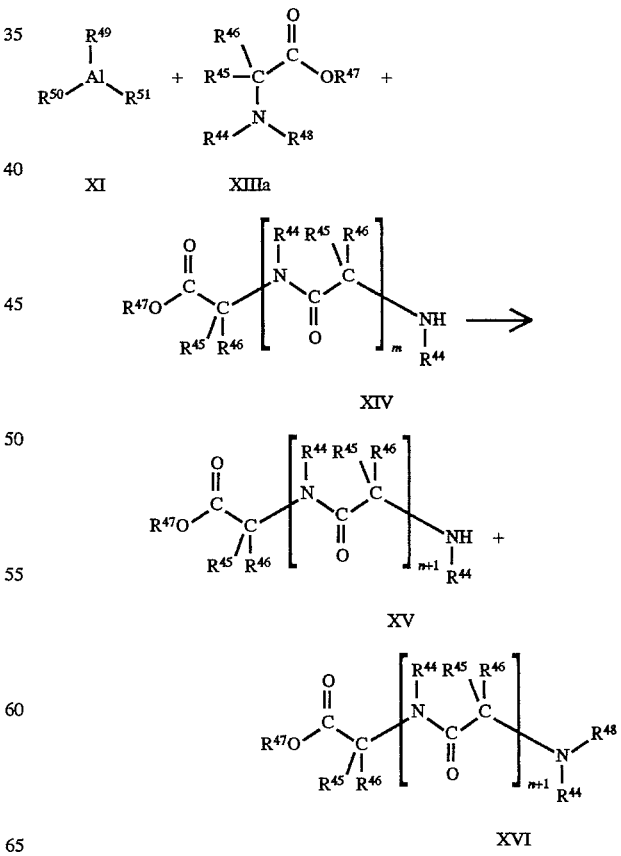

wherein:

$R^{44}$ is selected from the group H; $C_2$–$C_{12}$ alkenyl; $C_1$–$C_{12}$ alkyl or $C_3$–$C_6$ cycloalkyl each optionally substituted with a substituent selected from the group morpholinyl, $C_1$–$C_6$ alkylamino, $C_2$–$C_6$ dialkylamino, pyridinyl and phenyl, each pyridinyl or phenyl optionally substituted with 1 or 2 substituents independently selected from the group halogen and $C_1$–$C_4$ alkyl; and phenyl optionally substituted with 1 or 2 substituents independently selected from the group halogen and $C_1$–$C_6$ alkyl; provided that when $R^{44}$, $R^{45}$ or $R^{46}$ occur multiply in the same formula, each substituent is independently selected from the defined group;

$R^{45}$ is selected from the group H and $C_1$–$C_6$ alkyl;

$R^{46}$ is selected from the group H; $C_1$–$C_6$ alkoxy; $C_1$–$C_6$ haloalkyl; $C_1$–$C12$ alkyl optionally substituted with a substituent selected from the group OH, $C_1$–$C_6$ alkoxy, SH, $C_1$–$C_6$ alkylthio, $C_1$–$C_6$ alkylsulfonyl, pyridinyl, phenyl, hydroxyphenyl, morpholinyl, amino, $C_1$–$C_6$ alkylamino, $C_2$–$C_6$ dialkylamino, 3-indolyl, 4-imidazolyl, 1-methyl-4-imidazolyl, C(=O)NH$_2$, C(=O)OH, NHC(=NH)NH$_2$, and C(=NH)NH$_2$; and phenyl optionally substituted with 1 or 2 substituents independently selected from the group halogen and $C_1$–$C_6$ alkyl; or $R^{45}$ and $R^{46}$ are taken together to form a member selected from the group —CH$_2$CH$_2$CH$_2$CH$_2$CH$_2$—, —CH$_2$CH$_2$CH$_2$CH$_2$— and —CH$_2$CH$_2$CH$_2$—; or $R^{46}$ and $R^{47}$ are taken together to form a member selected from the group —CH$_2$CH$_2$CH$_2$CH$_2$—, —CH$_2$CH$_2$CH$_2$— and —CH$_2$CH$_2$—;

$R^{47}$ is selected from the group H, phenyl and $C_1$–$C_{12}$ alkyl; or $R^{44}$ and $R^{46}$ are taken together to form a member selected from the group —CH$_2$CH$_2$CH$_2$CH$_2$—, —CH$_2$CH$_2$CH$_2$—, —CH$_2$CH$_2$—, —CH$_2$CH(OH)CH$_2$— and —CH$_2$CH$_2$OCH$_2$—;

$R^{48}$ is selected from the group H and $C_1$–$C_4$ alkyl; or $R^{44}$ and $R^{48}$ are taken together to form a member selected from the group —CH$_2$CH$_2$CH$_2$CH$_2$CH$_2$— and —CH$_2$CH$_2$CH$_2$CH$_2$—;

$R^{49}$, $R^{50}$ and $R^{51}$ are independently $C_1$–$C_6$ alkyl; and n is 0 or an integer from 1 to 5.

Preferred embodiments of the above process comprise processes wherein n is 0 in XIV, XV and XVI and involves:

(a) first contacting the trialkylaluminum with the α-amino acid, ester or lactone of Formula XIV followed by contacting the mixture with an α-amino acid, ester or lactone of Formula XIIIa to produce the dipeptide of Formula XV, provided that $R^{48}$ is H; or (b) first contacting the trialkylaluminum with an α-amino acid, ester or lactone of Formula XIIIa followed by contacting the mixture with an α-amino acid, ester or lactone of Formula XIV to produce the dipeptide of Formula XV; or (c) adding the trialkylaluminum to a mixture of compounds of Formulae XIIIa and XIV to produce one or both dipeptides of Formulae XV and XVI.

DETAILS OF THE INVENTION

Compounds of Formula I may exist as one or more stereoisomers. The various stereoisomers include enantiomers, diastereomers and geometric isomers. One skilled in the art will appreciate that one stereoisomer may be the more active. One skilled in the art knows how to separate said enantiomers, diasteriomers and geometric isomers. Accordingly, the present invention comprises racemic mixtures, individual stereoisomers, and optically active mixtures.

The term "monocyclic aromatic ring" is defined as those monocyclic rings which satisfy the Hückel rule, examples include: 5- or 6- membered monocyclic aromatic rings containing 0 to 4 heteroatoms such as phenyl, furyl, furazanyl, thienyl, pyrrolyl, pyrazolyl, oxazolyl, oxadiazolyl, imidazolyl, isoxazolyl, thiazolyl, thiadiazolyl, isothiazolyl, tetrazolyl, pyridinyl, pyrimidinyl, pyridazinyl, pyrazinyl and triazinyl with said ring attached through any available carbon or nitrogen, for example, when the aromatic ring system is furyl, it can be 2-furyl or 3-furyl, for pyrrolyl, the aromatic ring system is 1-pyrrolyl, 2-pyrrolyl or 3-pyrrolyl, for pyridyl, the aromatic ring system is 2-pyridyl, 3-pyridyl or 4-pyridyl and similarly for other monocyclic aromatic rings.

The term "fused bicyclic aromatic ring" is defined as a fused bicyclic ring wherein at least one ring satisfies the Hückel rule, examples include quinolyl, isoquinolyl, quinoxalinyl, benzofuranyl, 2,3-dihydrobenzofuranyl, isobenzofuranyl, benzothienyl, benzodioxolyl, chromanyl, indolinyl, isoindolyl, naphthyl, thienofuranyl, and purinyl. As with the monocyclic aromatic rings, the fused bicyclic aromatic rings can be attached through any available carbon or nitrogen, for example, for naphthyl, the carbobicyclic aromatic ring is 1-naphthyl or 2-naphthyl and for benzofuranyl, the aromatic ring system can be 2-, 3-, 4-, 5-, 6-, or 7-benzofuranyl.

In the above recitations, the term "alkyl" used either alone or in compound words such as "alkylthio" denotes straight or branched alkyl such as methyl, ethyl, n-propyl, isopropyl and the different butyl, pentyl and hexyl isomers. Examples of "alkylsulfonyl" include CH$_3$S(O)$_2$, CH$_3$CH$_2$S(O)$_2$, CH$_3$CH$_2$CH$_2$S(O)$_2$, (CH$_3$)$_2$CHS(O)$_2$ and the different butylsulfonyl, pentylsulfonyl and hexylsulfonyl isomers. Alkoxy denotes methoxy, ethoxy, n-propyloxy, isopropyloxy and the different butoxy, pentoxy and hexyloxy isomers. Alkenyl denotes straight or branched chain alkenes such as vinyl, 1-propenyl, 2-propenyl and the different butenyl, pentenyl and hexenyl isomers. "Alkenyloxy" denotes straight-chain or branched alkenyloxy moieties, examples include H$_2$C=CHCH$_2$O, (CH$_3$)$_2$C=CHCH$_2$O, (CH$_3$)CH=CHCH$_2$O, (CH$_3$)CH=C(CH$_3$)CH$_2$O and CH$_2$=CHCH$_2$CH$_2$O. "Alkynyloxy" denotes straight-chain or branched alkynyloxy moieties, examples include HC≡CCH$_2$O, CH$_3$C≡CCH$_2$O and CH$_3$C≡CCH$_2$CH$_2$O. Cycloalkyl denotes cyclopropyl, cyclobutyl, cyclopentyl and cyclohexyl.

The term "halogen", either alone or in compound word such as "haloalkyl", denotes fluorine, chlorine, bromine or iodine. Further, when used in compound words such as "haloalkyl", said alkyl can be partially or fully substituted with independently selected halogen atoms. Examples of haloalkyl include CH$_2$CH$_2$F, CF$_2$CF$_3$ and CH$_2$CHFCl.

The total number of carbon atoms in a substituent group is indicated by the "$C_i$–$C_j$" prefix where i and j are numbers from 1 to 12. For example, $C_4$ alkoxy designates the various isomers of an alkoxy group containing a total of 4 carbon atoms, examples including OCH$_2$CH$_2$CH$_2$CH$_3$, OCH$_2$CH(CH$_3$)$_2$, OC(CH$_3$)$_3$.

Preferred compounds of Formula I for reasons including ease of synthesis and/or greater herbicidal efficacy are:

1. A compound of Formula I wherein
A and B are taken together as X-Y-Z;

X is $CHR^3$; or $CHR^4CHR^5$;
Y is $CHR^6$ or O;
Z is $CHR^7$; $CHR^4CHR^5$; or —X-Y— or —Y-Z— is

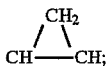

$R^{12}$ is H; $C_1$-$C_8$ alkyl; $C_1$-$C_8$ haloalkyl; halogen; OH; $OR^{17}$; SH; $S(O)_nR^{17}$; $COR^{17}$; $CO_2R^{17}$; $C(O)SR^{17}$; $C(O)NR^{19}R^{20}$; CHO; $CH=CHCO_2R^{17}$; $CO_2N=CR^{21}R^{22}$; $NO_2$; CN; $NHSO_2R^{23}$; or $NHSO_2NHR^{23}$; and $R^3$, $R^4$, $R^5$, $R^6$ and $R^7$ are independently H; halogen; $CF_3$ or $C_1$-$C_4$ alkyl;

provided that only one of $R^3$, $R^4$, $R^5$, $R^6$ and $R^7$ is other than hydrogen.

2. Compounds of Preferred 1 wherein

Q is selected from the group consisting of Q-1, Q-2, Q-3, Q-4 and Q-5;

$R^{17}$ is $C_1$-$C_4$ alkyl; $C_3$-$C_4$ alkenyl; $C_3$-$C_4$ alkynyl; $C_2$-$C_4$ alkoxyalkyl; $C_1$-$C_4$ haloalkyl; $C_3$-$C_4$ haloalkenyl or $C_3$-$C_4$ haloalkynyl; and $R^3$, $R^4$, $R^5$, $R^6$ and $R^7$ are independently H; F; $CH_3$ or $CF_3$.

3. Compounds of Preferred 2 wherein $R^1$ is H; and $R^{13}$ is halogen or CN.

4. Compounds of Preferred 3 wherein $R^2$ is $CO_2R^{34}$ or $CONR^{35}R^{36}$; and $R^3$, $R^4$, $R^5$, $R^6$ and $R^7$ are independently H or F.

Specifically preferred is a compound of Preferred 4 which is:

ethyl 2-(4-chloro-2-fluorophenyl)octahydro-1-oxoimidazo[1,5-a]pyridine-3-carboxylate.

The compounds represented by Formula I can be prepared according to the methods illustrated below in Schemes 1–8. The definitions of A, B, G, W, X, Y, Z, and $R^1$ through $R^{38}$ in the compounds of Formula I–VIII below are as defined above in the Summary of the Invention. Compounds of Formula Ia–Ih are within the defintion of compounds of Formula I.

Compounds of Formula Ia wherein $R^{40}$ is hydrogen, $C_1$-$C_4$ alkyl, or $C_1$-$C_4$ haloalkyl may be prepared by condensing amides of Formula II with dihalides or carbonyl compounds of Formula III as illustrated in Scheme 1. Compounds of Formula Ia are compounds of Formula I wherein $R^1$ is other than halogen.

Scheme 1

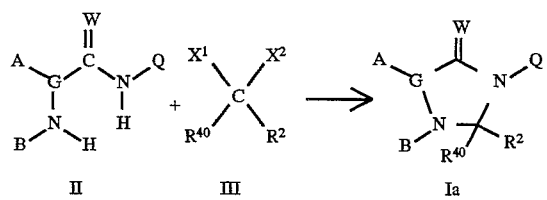

$R^{40} = R^1$ other than halogen;

$X^1$ and $X^2$ are independently F, Br, Cl, or I; or $X^1$ and $X^2$ can be taken together along with the carbon to which they are attached to form C=O.

When the compound of Formula III is an aldehyde or ketone ($X^1$ and $X^2$ are taken together with the attached carbon to form C=O), amides of Formula II are condensed with the carbonyl compound in the presence of sodium hydroxide in water at a temperature between 0° and 25° C. using the procedures described by D. A. Johnson in *J. Org. Chem.*, (1966), 31, 897.

When the compound of Formula III is a dihalide ($X^1$ and $X^2$ are halogens), the condensation is conducted in the presence of a base by heating the mixture 6f II and III in an inert solvent. Preferred dihalides of Formula III are ethyl bromofluoroacetate and ethyl bromodifluoroacetate. Examples of suitable bases include alkali salts of carbonate, such as potassium, sodium and lithium, and hydride bases such as sodium hydride. Examples of inert solvents include ethers such as diethyl ether, tetrahydrofuran and dioxane; esters such as ethyl acetate; amides such as dimethylformamide; and acetonitrile. Although the cyclization of compounds of Formula II with dihalides of Formula III proceeds at room temperature, the reaction is preferably performed by heating above room temperature.

Once the reaction is complete, the reaction mixture is diluted with an organic solvent and washed with water. Evaporation of the solvent affords the crude imidazolinone of Formula Ia which can be purified by chromatography or recrystallization.

Dihalides, aldehydes and ketones of Formula III can be prepared by known methods and many are commercially available. For example, see March, J. *Advanced Organic Chemistry*; 3rd ed., John Wiley: New York, 1985.

Compounds of Formula I wherein $R^1$ is halogen can also be prepared using the procedure as outlined in Scheme 2. In this instance, $X^1$ and $X^2$ are halogens as indicated in the compounds of Formula IIIa.

Scheme 2

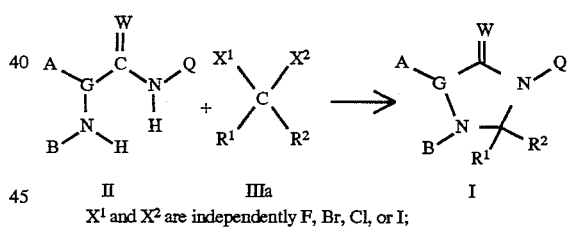

$X^1$ and $X^2$ are independently F, Br, Cl, or I;

Some compounds of Formula II, compounds of Formula IIa, can be prepared as outlined in Scheme 3. Compounds of Formula IIa are compounds of Formula II wherein G is CH or C($C_1$-$C_4$ alkyl) and W is O. The ester or acid of Formula V wherein $R^{39}$ is hydrogen, $C_1$-$C_6$ alkyl, phenyl, or benzyl, (e.g., proline, pipecolinic, or valine acid or esters), is reacted with a substituted-phenyl amine of Formula IV and a trialkylaluminum reagent (e.g., trimethylaluminum), in a non-coordinating solvent such as an aromatic hydrocarbon (e.g., benzene and toluene) or halogenated hydrocarbon (e.g., methylene chloride, chloroform, carbon tetrachloride, and dichlorobutane) to obtain an amide of Formula IIa. Generally, the reaction requires 0.1 to 48 h at a temperature of 0° to 25° C. to proceed to completion. The amides of Formula IIa are isolated by extraction into an organic solvent, aqueous wash, and removal of the solvent in vacuo. Purification can be accomplished by chromatography or recrystallization.

Scheme 3

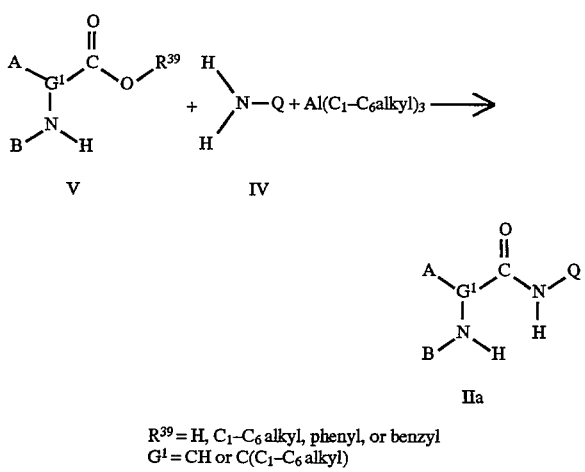

$R^{39}$ = H, $C_1$-$C_6$ alkyl, phenyl, or benzyl
$G^1$ = CH or C($C_1$-$C_6$ alkyl)

Alternatively, amides of Formula IIa can be generated using conventional 1,3-dicyclohexylcarbodiimide (DCC) procedures for coupling N-protected compounds of Formula Va with amines of Formula IV followed by removal of the protecting group according to the procedures outlined by Bodanszky, M. in *Principles of Peptide Synthesis*, Volume 16, Springer-Verlag, New York, (1984) (Scheme 4).

Scheme 4

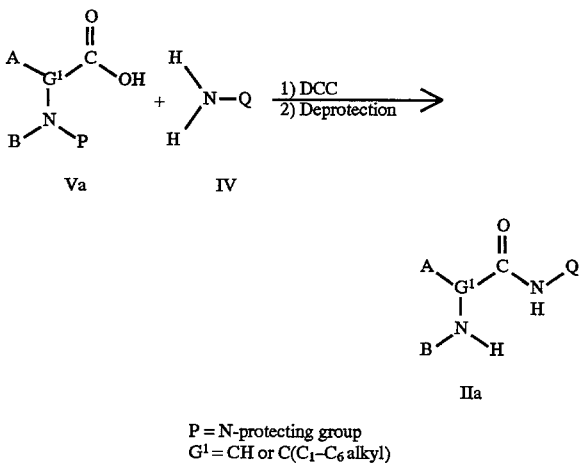

P = N-protecting group
$G^1$ = CH or C($C_1$-$C_6$ alkyl)

α-Amino esters and acids of Formulae V and Va can be prepared by known methods and many are commercially available. See for example, R. M. Williams in *Synthesis of Optically Active α-Amino Acids*, Vol. 27, Pergamon, New York: (1989). Substituted-phenyl amines of Formula IV can also be prepared by known methods. For example, the synthesis of amines of Formula IV wherein Q is Q-1, Q-4, Q-5, and Q-8 is described in U.S. Pat. No. 4,902,335. The synthesis of amines wherein Q is Q-2 and Q-3 can be prepared as described in U.S. Pat. No. 5,053,071 or by well known modifications thereof. The amines of Formula Q-6 and Q-7 can be prepared by well known functional group transformations of known phenyl derivatives.

Amides of Formula II wherein G is N, compounds of Formula IIb, can be prepared according to the method outlined in Scheme 5. Hydrazines of Formula VI are reacted with an isocyanate (W=O) or isothiocyanate (W=S) of Formula VII in an inert solvent such as methylene chloride at about 0° to 80° C. The isocyanates and isothiocyanates are prepared by known methods from the appropriate aniline (see EP-A-448,188). Many hydrazines of Formula VI are known and others can be prepared by known methods.

Scheme 5

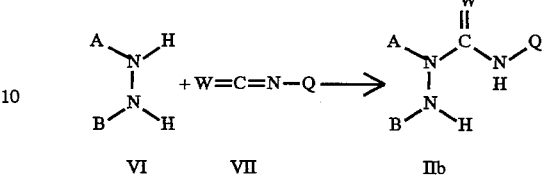

Alternatively, some compounds of Formula I (compounds of Formula Id) may be prepared by transforming the nature of the $R^2$ group of imidazolinones of Formula Ic (Scheme 6). Compounds of Formula Id are compounds of Formula I wherein W is O and $R^2$ is methyl optionally substituted with one or more halogens, $OR^8$, CN, $COR^9$, $CO_2R^{31}$ or $CONR^{32}R^{33}$; CN; $CO_2R^{34}$; $CONR^{35}R^{36}$; $S(O)_nR^8$; or $S(O)_nNR^8R^{19}$. Compounds of Formula Ic are compounds of Formula I wherein W is O and $R^2$ is $CO_2Et$ and may be prepared by the methods illustrated in Schemes 1 and 2.

Scheme 6

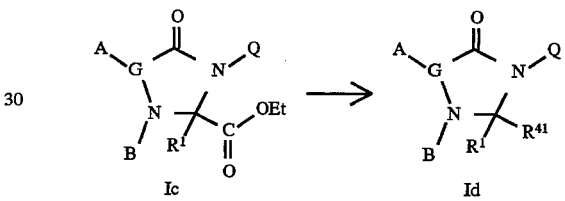

$R^{41}$ = methyl optionally substituted with halogens,
$OR^8$, CN, $COR^9$, $CO_2R^{31}$, or $CONR^{32}R^{33}$;
CN; $CO_2R^{34}$; $CONR^{35}R^{36}$; $S(O)_nR^8$;
$S(O)_nNR^{19}R^8$; or $COR^{37}$ The ester of Formula Ic is hydrolyzed with sodium hydroxide in solvent such as methanol or ethanol at about 0° to 50° C. to provide the corresponding carboxylic acid. The acid can be convened to the corresponding ester ($R^{41}$=$CO_2R^{34}$) or the amide ($R^{41}$=$CONR^{35}R^{36}$) of Formula Id by treatment with thionyl chloride or oxalyl chloride to form the acid chloride followed by treatment with the appropriate alcohol $R^{34}$—OH or amine H—$NR^{35}R^{36}$, respectively.

Treatment of the acid chloride with ammonia produces the unsubstituted amide, $R^{41}$=$CONH_2$, which can be dehydrated by conventional procedures to form the nitrile, $R^{41}$=CN.

Alternatively, esterification of the carboxylic acid can be be achieved by reacting the acid with an appropriate alkyl halide in the presence of a base such as potassium carbonate in an inert solvent such as dimethylformamide at about 0° to 60° C. to give the ester of Formula Id ($R^{41}$=$CO_2R^{34}$).

The amide of compound Id ($R^2$=$CONR^{35}R^{36}$), can also be obtained by conventional 1,3-dicyclohexylcarbodiimide (DCC) coupling between the carboxylic acid and the appropriate amine H—$NR^{35}R^{36}$. The DCC coupling procedure is described by Bodanszky, M. and Bodanszky, A; in *The Practice of Peptide Synthesis*, Vol. 21; Springer-Verlag, New York: (1984).

Reduction of the carboxylic acid or ester with a reducing agent such as lithium aluminum hydride in solvent such as terahydrofuran at 0° to 80° C. produces the corresponding alcohol, a compound of Formula Id wherein $R^{41}$=$CH_2OH$.

Treatment of the alcohol with an $R^8$-halide, in the presence of a base, such as potassium carbonate, in an inert solvent, such as acetonitrile, produces compounds of Formula Id wherein $R^{41}$ is $CH_2OR^8$.

Other $R^{41}$ substituents are also derivable from the $CO_2Et$ group in compounds of Formula Ic using known functional group transformations.

Imidazolinones of Formula I wherein $R^1$ and $R^2$ are taken together, compounds of Formula Ih, are prepared as illustrated in Scheme 7. Amides of Formula II are treated with ketene dithioacetals of Formula VIII to form imidazolinones of Formula Ig. The reaction occurs in the presence of triethylamine or sodium methoxide/ethoxide in ethanol or methanol at reflux according to the procedure outlined by Z. T. Huang et al. in Synth. Commun., (1991), 21, 1177–1187. The ketene dithioacetals of Formula VIII are known or can be prepared by known methods.

The ester group in imidazolinones of Formula Ig can be hydrolyzed to the corresponding carboxylic acid as described previously (see Scheme 6). The acid can then be converted to other esters or to amides using well-known procedures and discussed above to give compounds of Formula Ih.

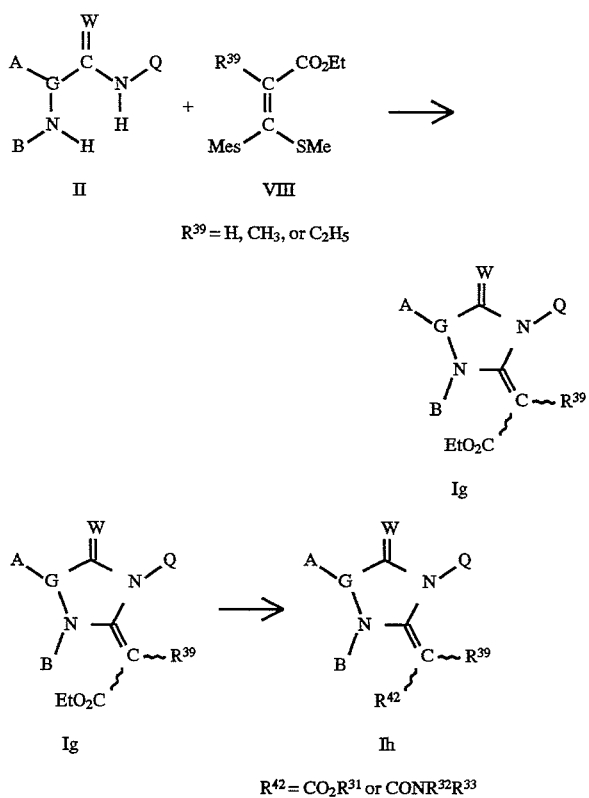

In addition to the methods described above, compounds of Formula I wherein W=S (If) can be obtained from the corresponding compound of Formula I wherein W=O (Ie) by treatment with Lawesson's reagent (2,4-bis(4-methoxyphenyl)-1,3-dithia-2,4-diphosphetane-2,4-disulfide, Scheme 8). If the imidazolinone of Formula Ie contains a second carbonyl group, one skilled in the an recognizes that protection of said carbonyl group may be required. See Greene, T. W. and Wuts, P. G. M.; Protective Groups in Organic Synthesis, 2nd Ed.; John Wiley & Sons, Inc.; New York, (1980) for suitable protecting groups. The thionation is performed in an inert solvent such as benzene, toluene, or chloroform at room temperature to 115° C. according to the method of S. O. Lawesson et al. in Nouv. J. Chim., (1980), 4, 47.

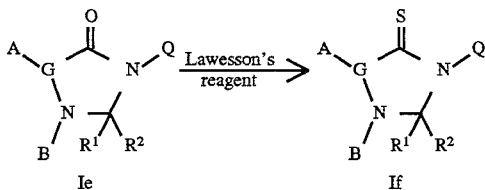

The process for the preparation of amides of Formula IX and peptides of Formulae XV and XVI is described below.

One skilled in the art will recognize that some amides of Formula IX are the amide intermediates of Formula II used in the preparation of the imidazolones of Formula I. Some compounds of Formula II are some compounds of Formula IX wherein $R^{43}$ is Q, $R^{44}$ is H, $R^{46}$ is A, m is 0, $R^{44}$ is B, and $R^{48}$ is H. Therefore, the process described hereinafter can be used to prepare imidazolones of Formula I.

The term α-amino defines an amino group, $NH_2$, or its hydrogen halide salt, attached to the α-carbon of a carboxylic acid, ester or lactone. The nitrogen atom of the amino group can optionally be substituted or is part of a cyclic ring containing 5 to 6 atoms. The term unprotected is defined to mean that no synthetic manipulation is required to functionalize (protect) the α-amino group of the acid, ester or lactone prior to contact with the trialkylaluminum and amine. Protection of the α-amino moiety is normally required in the synthetic manipulation of α-amino acids to (i) overcome undesired product formation resulting from the unwanted participation of the α-amino moiety in the reaction and/or (ii) loss of configurational integrity at the carbon bearing the α-amino moiety. The loss of configurational integrity is defined to mean substantial racemization when the starting α-amino acid, ester or lactone is chiral at the carbon bearing the α-amino moiety. The term chiral when applied to the α-amino acid, ester or lactone is defined to mean enantiomerically pure, that is, consists of a single enantiomer, or enriched in one enantiomer. That is, the chiral molecules are optically active. Typical N-protecting groups used in α-amino acid manipulations, particularly for the synthesis of α-amino amides from α-amino acids, include forming carbamates, formamides, acetamides, benzamides or cyclic derivatives (using phosgene). For a discussion of the protection of amino groups see Greene, T. W. and Wuts, P. G. M., Protective Groups in Organic Synthesis, 2nd Ed.; John Wiley & Sons, Inc.: New York, (1991).

In a preferred embodiment of the process of the present invention, the desired amine is first converted to an aluminum amide of Formula XII by treatment of the amine in a non-coordinating solvent such as benzene, chlorobutane, 1,2-dichloroethane, carbon tetrachloride, chloroform, hexane, acetonitrile, toluene or methylene chloride with a trialkylaluminum at a temperature of about –10° C. to about 150° C. The resultant aluminum amide which is not isolated is treated at a temperature of about –10° C. to about 150° C. with the free base or hydrogen halide salt of an α-amino carboxylic acid, ester or lactone to yield the corresponding α-amino amide. A representative reaction is shown in Equations 1 and 2 of Scheme 9.

15

Scheme 9

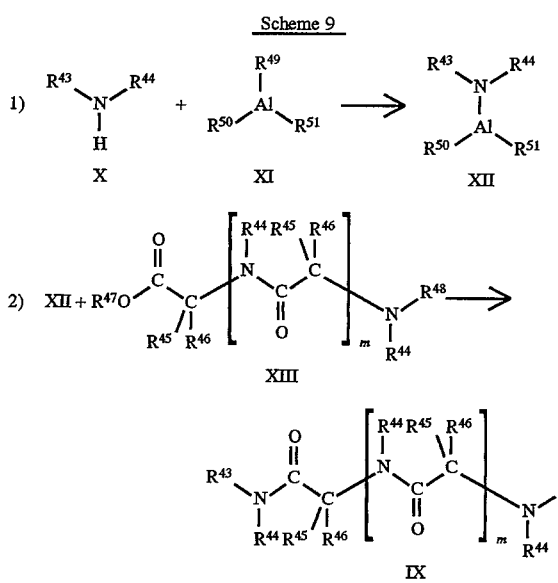

wherein $R^{43}$, $R^{44}$, $R^{45}$, $R^{46}$, $R^{47}$, $R^{48}$, $R^{49}$, $R^{50}$, $R^{51}$ and m are as defined above in the corresponding Formulae. A preferred embodiment of the process illustrated in Scheme 9 involves compounds XIII and IX wherein m is 0. A more preferred process is that in which m is 0 and the α-amino acid, ester or lactone of Formula XIII is optically active.

The amines (X) and the α-amino carboxylic acid, ester or lactones (XIII) are known or easily prepared by known methods or by the method of the present invention. Trialkylaluminum reagents of Formula XI are commercially available or easily prepared by known methods. The process of the present invention is particularly advantageous when the α-amino carboxylic acid, ester or lactone is chiral, as no detectable racemization occurs. Thus, the process of the present invention is an improvement over known methods in its simple (one-pot) procedure for convening an α-amino carboxylic acid, ester or lactone, without protection of the α-amino group, while maintaining the configurational integrity of the starting α-amino containing substrate.

In one example of the process of the present invention, an amine of Formula X is dissolved or suspended in a non-coordinating solvent such as benzene, chlorobutane, 1,2-dichloroethane, carbon tetrachloride, chloroform, hexane, acetonitrile, toluene or methylene chloride. A solution of 1–4 molar equivalents added to the amine solution at 0° C. The resultant mixture containing the aluminum amide is allowed to warm to room temperature and is stirred for 0.1 to 48 hours. The mixture is then cooled to 5°–10° C., treated with the α-amino carboxylic acid, ester or lactone of Formula XIII and allowed to warm to room temperature and stirred for 0.1 to 72 hours. Isolation of the amino amide (IX) yields a product with no detectable loss of stereochemical integrity.

Alternatively, the order of addition of the reactants can be reversed when m is 0. The α-amino carboxylic acid, ester or lactone of Formula XIII is dissolved or suspended in one of the organic solvents listed above and treated with 1–4 molar equivalents of a trialkylaluminum (e.g., trimethylaluminum in hexane) at 0° C. After warming the resulting mixture to room temperature, stirring for 0.1 to 48 hours, and subsequent cooling to 5°–10° C., the mixture is then treated with the amine of Formula X. Again, the amino amide (IX) which forms after 0.1 to 72 hours at room temperature undergoes no detectable loss of stereochemical integrity.

A third method of performing the process of the present invention is to add the trialkylaluminum to a cooled mixture of the α-amino carboxylic acid, ester or lactone of Formula XIII and amine of Formula X in a non-coordinating solvent. The mixture is warmed to room temperature and stirred for 0.1 to 72 hours. Once again, isolation of the amino amide (IX) yields a product with no detectable racemization.

When the starting amine is an α-amino carboxylic acid, ester or lactone, that is, a compound of Formula XIV, one skilled in the art will recognize the present process as a convenient procedure for making di- and polypeptides of Formulae XV and XVI (see Scheme 10)

Scheme 10

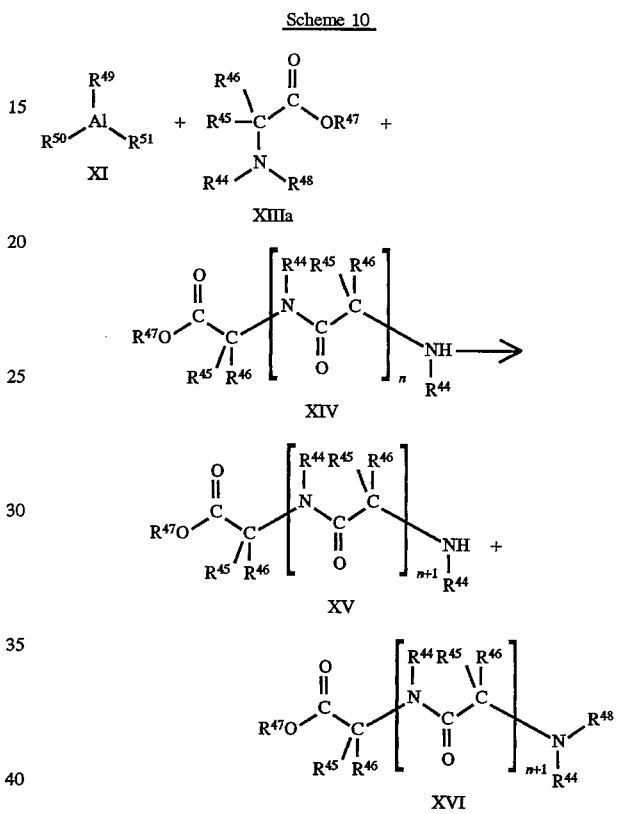

wherein $R^{44}$, $R^{45}$, $R^{46}$, $R^{47}$, $R^{48}$, $R^{49}$, $R^{50}$, $R^{51}$ and n are as defined above in the corresponding Formulae.

A preferred embodiment of the process illustrated in Scheme 10 involves compounds of Formula XIV wherein n is 0. In these cases, two α-amino acids, esters or lactones react to form one or more dipeptides of Formulae XV and XVI. The order of addition of the reactants influences whether one or both dipeptides are formed, and when one dipeptide is formed, whether the structure is of Formula XV or XVI. Another preferred embodiment of the process illustrated in Scheme 10 involves an α-amino carboxylic acid, ester, or lactone of Formula XIIIa which is optically active. Also preferred is the process involving an optically active α-amino carboxylic acid, ester, or lactone of Formula XIV. A more preferred embodiment involves α-amino carboxylic acids, esters, or lactones of Formulae XIIIa and XIV which are both optically active.

In an example of the process illustrated in Scheme 10, an α-amino acid, ester or lactone of Formula XIIIa is dissolved or suspended in a non-coordinating solvent such as benzene, chlorobutane, 1,2-dichloroethane, carbon tetrachloride, chloroform, hexane, acetonitrile, toluene or methylene chloride. A solution of 1–4 molar equivalents (depending on the nature of the amine) of trimethylaluminum in hexane is slowly added to the amine solution at 0° C. The resultant mixture containing the aluminum amide is allowed to warm to room temperature and is stirred for 0.1 to 48 hours. The mixture is then cooled to 5°–10° C., treated with the α-amino carboxylic acid, ester or lactone of Formula XIV and allowed to warm to room temperature and stirred for 0.1 to 72 hours. Isolation of the compound of Formulae XV or XVI, or both XV and XVI, yields a di- or polypeptide with no detectable loss of stereochemical integrity.

Scheme 11 illustrates the process of the present invention for the preparation of dipeptides of Formula XV (n is 0).

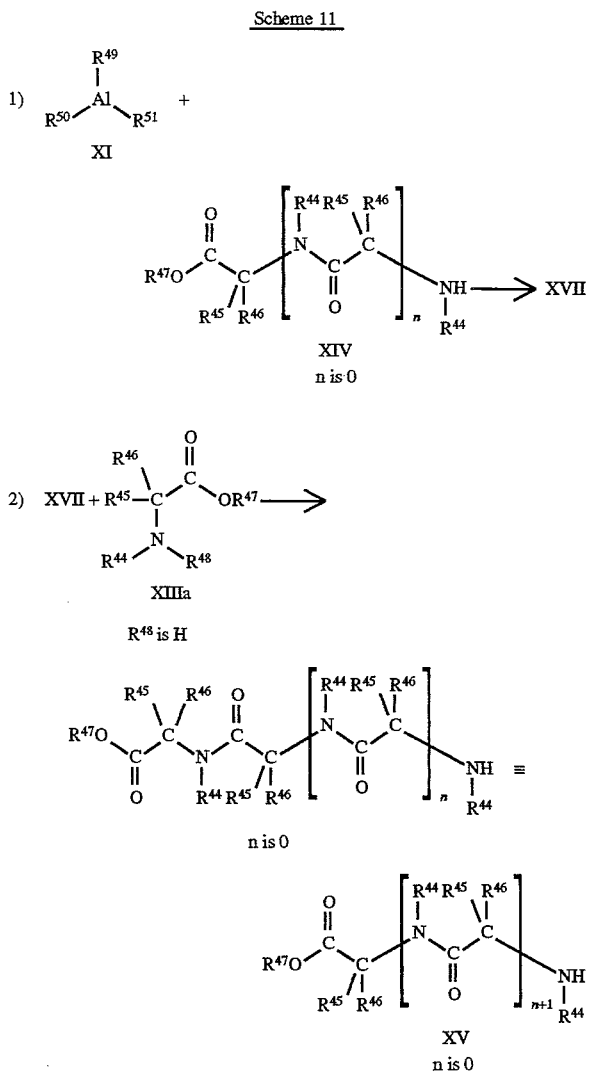

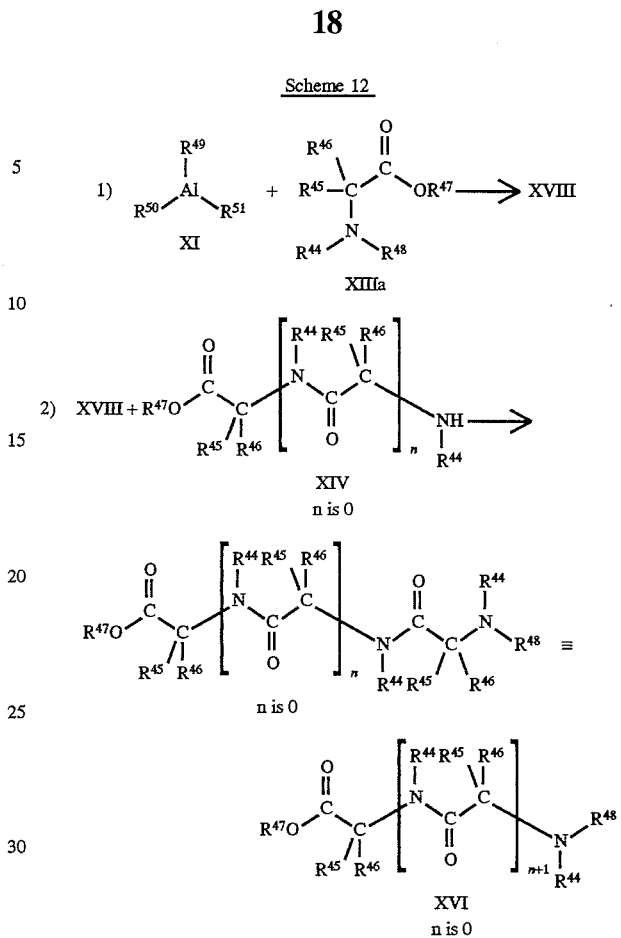

In Equation 1, a trialkylaluminum reagent of Formula XI is first contacted with an α-amino carboxylic acid, ester or lactone of Formula XIV to form the (α-amino carboxylic acid, ester, or lactone):alkylaluminum complex of Formula XVII. In Equation 2, this complex is then reacted with an α-amino carboxylic acid, ester or lactone of Formula XIIIa (provided $R^{48}$ is H) to afford the dipeptide product of Formula XV (n is 0).

Scheme 12 illustrates the process of the present invention for the preparation of dipeptides of Formula XVI (n is 0).

In Equation 1, a trialkylaluminum of Formula XI is first contacted with an α-amino carboxylic acid, ester, or lactone of Formula XIIIa to form an (α-amino carboxylic acid, ester, or lactone):alkylaluminum complex of Formula XVIII. As illustrated in Equation 2, this complex is then reacted with an α-amino carboxylic acid, ester or lactone of Formula XIV to afford the dipeptide product of Formula XVI (n=0).

The dipeptide product of Formula XV (n is 0) can be further processed by treatment with a trialkylaluminum of Formula XI and an α-amino carboxylic acid, ester or lactone of Formula XIIIa (the same or different from the compound of Formula XIIIa in Scheme 11) to provide one or both of the tripeptide products of Formulae XV and XVI (n is 1 in each). This sequence is the same as that illustrated in Scheme 10 wherein the dipeptide product of Formula XV is now the reactant of Formula XIV wherein n is 1. The relative amounts of tripeptide products XV and XVI will be determined by the order of addition of the reactants XI, XIIIa, and XIV, and the particular identities of $R^{44}$, $R^{45}$, $R^{46}$, $R^{47}$, and $R^{48}$.

In a similar manner, the dipeptide product of Formula XVI (n is 0) can be further processed to tripeptides of Formulae XV and XVI (n is 1 in each), provided that at least one of $R^{44}$ and $R^{48}$ on the terminal nitrogen of XVI is H. The dipeptide of Formula XVI is treated with a trialkylaluminum and an α-amino carboxylic acid, ester or lactone of Formula XIIIa (the same or different from the compound of Formula XIIIa in Scheme 12). This process is also illustrated in Scheme 10 wherein the dipeptide product of Formula XVI is now the reactant of Formula XIV wherein n is 1 and $R^{48}$ is H. As in the process involving the dipeptide of Formula XV as the reactant, the relative amounts of tripeptide products XV and XVI is determined by the order of addition of the reactants XI, XIIIa, and XIV, and the particular identifies of $R^{44}$, $R^{45}$, $R^{46}$, $R^{47}$, and $R^{48}$.

The coupling procedure can continue to yield higher peptides simply by repeating the process illustrated in Scheme 10. That is, treatment of a peptide of Formula XIV containing (n+1) amino acid residues with a trialkylaluminum reagent of Formula XI and an α-amino carboxylic acid, ester or lactone of Formula XIIIa affords one or both peptides of Formulae XV and XVI containing (n+2) amino acid residues. In this manner, the present process allows for the convenient preparation of peptides with varying numbers of amino acid residues per molecule. Side products can form in this process from the reaction of the aluminum complex of Formula XV or XVI with itself rather than with XIIIa.

The process illustrated in Scheme 10 is particularly useful for the preparation of di- and polypeptides wherein the peptide residues are identical. For example, when the compound of Formula XIIIa in Scheme 10 is the same as the compound of Formula XIV the resulting dipeptide comprises two identical amino acid residues. In these cases, the dipeptide is a compound of Formulae XV and XVI. A convenient method of carrying out this process is to add the trialkylaluminum to a solution or suspension containing all of the α-amino carboxylic acid, ester, or lactone. The side product reaction of the aluminum complexes (XVII or XVIII) reacting with themselves also produces the desired product, hence, undesired side product formation is minimized.

The products of the present process invention are useful intermediates for the preparation of pharmaceuticals, the compounds of Formula I, and other agricultural chemicals.

The following Examples further illustrate the invention.

EXAMPLE 1

Ethyl 2-[4-chloro-2-fluoro-5-[(1-methylethoxy) phenyl]]hexahydro-1-oxo-3H-imidazo[5,1-c][1,4]oxazine-3-carboxylate Step A: 4-Chloro-2-fluoro-5-(1-methylethoxy)aniline A stirring mixture of 5-amino-2-chloro-4-fluorophenol (22.0 g, 136.19 mmol), 2-bromopropane (38.4 mL, 50.25 g, 408.57 mmol) and potassium carbonate (37.6 g, 273.0 mmol) was heated at reflux for 17 h. The reaction mixture was cooled and filtered. The filtrate was evaporated to dryness under reduced pressure. Flash chromatography yielded the title compound of Step A as a brown oil (17.2 g). $^1$H NMR (CDCl$_3$): δ7.02 (d, 1H), 6.44 (d, 1H) 4.38 (q, 1H), 3.81 (br s,2H), 1.33 (d,6H). IR (cm$^{-1}$): 3378.4, 3475.6.

Step B: N-[4-Chloro-2-fluoro-5-(1-methylethoxy)phenyl] morpholine-3-carboxamide

To a stirring solution of 4-chloro-2-fluoro-5-(1-methylethoxy)aniline (15.52 g, 76.26 mmol) in CH$_2$Cl$_2$ (100 mL), under nitrogen at 0° C. (ice-bath) was added dropwise trimethylaluminum (114.4 mL, 228.78 mmol). The mixture was then stirred overnight at room temperature. 3-Morpholinecarboxylic acid (10.0 g, 76.20 mmol) was added portionwise at room temperature. The resultant reaction mixture was stirred at room temperature for 2 days. 6N HCl was added dropwise to the reaction mixture at 0° C. (ice-bath). The solid formed was filtered off and suspended in water (100 mL). The suspension was basicified with 50% aqueous NaOH to pH 13. 400 mL of CH$_2$Cl$_2$ was added. The organic layer was separated, dried over MgSO$_4$ and the solvent was removed under vacuum to give the title compound of Step B as a white solid (10.5 g), m.p. 99°–101° C. $^1$H NMR: δ9.30 (br s,1H), 8.17 (d,1H), 7.14 (d,1H), 4.53 (q,1H), 3.96–3.61 (m,5H), 3.00–3.01 (m,2H), 1.37 (d,6H).

Step C: Ethyl 2-[4-chloro-2-fluoro-5-[(1-methylethoxy) phenyl]]hexahydro-1-oxo-3H-imidazo[5,1-c][1,4]oxazine-3-carboxylate The mixture of product of Step B (2.5 g, 7.89 mmol), ethyl bromofluoroacetate (2.9 g, 15.78 mmol) and potassium carbonate (2.2 g, 16.0 mmol) in acetonitrile (100 mL) was heated at reflux for 17 h. The reaction mixture was filtered. The filtrate was removed under reduced pressure. Flash chromatography yielded the title compound of Step C as a yellow oil (400 mg). $^1$H NMR (CDCl$_3$): δ7.24 (d,1H), 7.18 (d,1H), 4.99 (s,1H), 4.50–4.22 (m,4H), 3.95–3.88 (m,2H), 3.75–3.62 (m,2H), 3.06 (m,2H), 1.37 (d,6H), 1.25 (t,3H).

EXAMPLE 2

Ethyl 2-[4-chloro-2-fluoro-5-(1-methylethoxy) phenyl]octahydro-1-oxoimidazo[1,5-a]pyridine-3-carboxylate Step A: N-[4-Chloro-2-fluoro-5-(1-methylethoxy) phenyl]piperidine-2-carboxamide.

The product of Example 1, Step A (4.25 g, 26.37 mmol) was dissolved in CH$_2$Cl$_2$ (200 mL). A solution of 2.0M trimethylaluminum (52.75 mmol) was added dropwise under nitrogen at 0° C. The resultant mixture was stirred at room temperature overnight. Ethyl pipecolinate (4.15 g) was added dropwise to the mixture and the mixture was stirred for 2 days. To the reaction mixture 6N HCl (100 mL) was added dropwise at 0° C. 200 mL of H$_2$O was added, followed by the addition of 150 mL of methylene chloride. The aqueous layer was separated and basicified to pH 10 with 50% aqueous NaOH. 500 mL of CH$_2$Cl$_2$ was added. The organic layer was separated, dried over MgSO$_4$, filtered and evaporated to dryness under vacuum to give the title compound of Step A as a white solid, 4.7 g. m.p. 96°–98° C. $^1$H NMR (CDCl$_3$): δ9.25 (br s,1H), 8.17 (d,1H), 7.13 (d,1H) 4.58 (m,1H), 3.20 (M,1H), 3.10 (m,1H), 2.79 (m,1H), 2.00 (m,1H), 1.89 (m,2H), 1.60–1.40 (m,4H), 1.36 (d,6H).

Step B: Ethyl 2-[4-chloro-2-fluoro-5-(1-methylethoxy) phenyl]octahydro-1-oxoimidazo[1,5-a]pyridine-3-carboxylate A mixture of potassium carbonate (724 mg, 5.24 mmol), ethyl bromofluoroacetate (882 mg, 4.76 mmol) and the product of Step A (1.5 g, 4.76 mmol) in acetonitrile (50 mL) was heated at reflux overnight. 100 mL of H$_2$O and 200 mL of ethyl acetate were added to the mixture. The organic layer was separated, dried (MgSO$_4$), filtered, and evaporated under vacuum to dryness. Flash chromatography yielded the title compound of Step B as a white solid (400 mg) m.p. 83°–85° C. $^1$H NMR δ7.21 (d,1H), 7.18 (d,1H), 4.92 (s,1H), 4.50 (m,1H), 4.16–4.09 (m,2H), 3.29 (m,1H), 2.95 (m,1H), 2.50 (m,1H), 2.10 (m,1H), 1.96 (m,1H), 1.80–1.58 (m,2H), 1.37 (d,6H), 1.35 (t,3H).

EXAMPLE 3

2-[4-Chloro-2-fluoro-5-(1-methylethoxy)phenyl] hexahydro-1-oxo-3H-imidazo[5,1-c][1,4]oxazine-3-carboxylic acid A mixture of 1N NaOH (9.36 mmol, 9.4 mL) and the product of Example 1 (2.5 g, 6.24 mmol) in ethanol was stirred at room temperature for 40 minutes. The reaction mixture was evaporated under reduced pressure to remove most of the ethanol solvent. The remaining aqueous solution was acidified with concentrated hydrochloric acid to pH 2. Diethyl ether (200 mL) was added. The organic layer was separated, dried over MgSO$_4$, and evaporated to dryness under reduced pressure to give the title compound as a yellow-white solid (1.59 g), m.p. 59°–61° C. IR (nujol, cm$^{-1}$), C=O (1729.9), OH (3300–3500, broad). $^1$H NMR (CDCl$_3$, 400 MHz): δ7.20–7.18 (m,2H), 5.50 (br s,1H), 5.20 (s,1H), 4.88–4.45 (m,2H), 3.91–3.80 (m,2H), 3.74–3.72 (m,2H), 3.20–3.15 (m,1H), 1.37–1.24 (m,6H).

EXAMPLE 4

3-Methylbutyl 2-[4-chloro-2-fluoro-5-(1-methylethoxy)phenyl]hexahydro-1-oxo-3H-imidazo[5,1-c][1,4]oxazine-3-carboxylate A mixture of 1-bromo-3-methylbutane (0.14 mL, 1.2 mmol), $K_2CO_3$ (167 mg, 1.2 mmol), and the product of Example 3 (300 mg, 0.8 mmol) in dimethyl formamide (2 mL) was stirred under nitrogen at room temperature overnight. Flash chromatography of the reaction mixture provided the title compound as a clear oil (162 mg). IR (neat, $cm^{-1}$), C=O (1741.9). $^1$H NMR (CDCl$_3$, 400 MHz): δ7.20–7.18 (m,2H), 5.00 (s,1H), 4.53–4.52 (m,1H), 4.36–4.29 (d,1H), 4.23–4.19 (m,2H), 3.93–3.83 (m,2H), 3.74–3.64 (br,2H), 3.15–3.12 (m,2H), 1.60–1.43 (m,3H), 1.39–1.36 (t,6H), 0.89–0.86 (t, 6H)

EXAMPLE 5

Ethyl 2-(4-ethyl-7-fluoro-3,4-dihydro-3-oxo-2H-1,4-benzoxazin-6-yl)hexahydro-3-oxo-1H-[1,2,4]triazolo[1,2-a]pyridazine-1-carboxylate Step A: Hexahydropyridazine dihydroiodide To a solution of 5% rhodium on alumina powder (3.0 g) in ethyl acetate (125 mL), diethyl 1,2,3,6-tetrahydropyrazine-1,2-carboxylate (30.00 g, 31.6 mmol) was added under nitrogen. The mixture was pressurized with hydrogen (2.75×10$^5$ Pa) and shaken on a Parr hydrogenator for 20 h. Chloroform (100 mL) was added to the reaction mixture and then the mixture was filtered through a Celite® bed. The filtrate was evaporated under reduced pressure to obtain a clear oil (28.1 g). Without further purification, 10.0 g (43.4 mmol) of the crude product was dissolved in chloroform (150 mL). Trimethylsilyl iodide (17.3 g, 24.3 mmol) was added dropwise under nitrogen. The resultant reaction mixture was gradually heated to 60° C. and kept at 60° C. for 4 h. The reaction mixture was then allowed to cool to room temperature and treated with methanol (5.5 g) over a 10 minute period. The reaction mixture was then evaporated under reduced pressure to dryness to give the title compound of Step A as a thick yellow oil (8.3 g). IR (neat, $cm^{-1}$) N—H (3180). $^1$H NMR (CDCl$_3$, 400 MHz): δ7.20–6.8 (br,2H), 3.39 (br,4H), 1.94 (br,4H).

Step B: N-(4-ethyl-6-fluoro-3,4-dihydro-3-oxo-2H-1,4-benzoxazin-7-yl)-tetrahydro-1(2H)-pyridazinecarboxamide To a stirring solution of the crude product of Example 5, Step A (1.80 g, 8.46 mmol) in methylene chloride (100 mL) was added triethylamine (3.0 g) dropwise under nitrogen at room temperature. Then, the mixture was stirred for 5 minutes. A solution of 4-ethyl-6-fluoro-3,4-dihydro-3-oxo-2H-1,4-benzoxazin-7-isocyanate (2.0 g, 8.46 mmol) in methylene chloride (20 mL) was added dropwise to the reaction mixture at 5° C. The resultant mixture was allowed to stir at ambient temperature overnight. Evaporation of the solvent under reduced pressure followed by flash chromatography gave the title compound of Step B as a white solid (1.3 g), m.p. 66°–68° C. IR (nujol, $cm^{-1}$) N—H 3238, 3397), C=O (1650, 1681). $^1$H NMR (DMSO-d$_6$, 300 MHz): δ8.80 (br,1H), 7.92–7.90 (d,1H), 7.20–7.18 (d,1H), 5.25–5.00 (m,1H), 4.62 (br,2H), 3.90–3.80 (m,2H), 3.55–3.40 (br,1H), 2.90–2.81(br,2H), 2.70–2.69 (br,1H), 1.57–1.52 (br,4H), 1.19–1.51 (br,4H).

Step C: Ethyl 2-(4-ethyl-6-fluoro-3,4-dihydro-3-oxo-2H-1,4-benzoxazin-7-yl) hexahydro-3-oxo-1H-[1,2,4]triazolo[1,2-a]pyridazine-1-carboxylate Using the procedure of Example 2, Step B and employing 1.9 g (10.23 mmol) of ethyl bromofluoroacetate, potassium carbonate (1.41 g, 10.23 mmol) and 1.0 g, (3.41 mmol) of the product of Example 5, Step B, the title compound was obtained as a white solid (410 mg), m.p. 59°–61° C. IR (nujol, $cm^{-1}$), C=O (1725.6). $^1$H NMR (CDCl$_3$, 300 MHz), δ7.45–7.42 (d,1H), 6.78–6.74 (d,1H), 5.02 (s,1H), 4.58 (s,2H), 4.19–4.16 (m,2H), 4.04–3.96 (m,3H), 3.06–3.05 (m,1H), 3.03–3.02 (m,2H), 1.88–187 (m,1H), 1.65–1.60 (m,4H), 1.32–1.21 (m,6H).

EXAMPLE 6

Ethyl 2-[4-chloro-2-fluoro-5-[(2-propynyl)oxy]phenyl]octahydro-1-oxoimidazo[1,5-a]pyridine-3-carboxylate Step A: 4-Chloro-2-fluoro-5-[(2-propynyl)oxy]aniline Using the procedure of Example 1, Step A and employing 50.0 g (252.45 mmol) of 3-amino-6-chloro-4-fluorophenol hydrochloride, 80% propargyl bromide (60.07 g, 504.9 mmol), and potassium carbonate (69.8 g, 504.9 mmol) in acetonitrile (200 mL), the title compound was obtained as a yellow solid (16.2 g), m.p. 62°–64° C. IR (nujol, era-1), $NH_2$ (3298.0), triple bond (2117.6). $^1$H NMR was consistent with the structure.

Step B: N-[(4-chloro-2-fluoro-5-[(2-propynyl)oxy]phenyl]-2-piperidine-carboxamide Using the procedure of Example 1, Step B and employing 11.82 g of ethyl pipecolinate, 2M trimethylaluminum solution in hexane (75.2 mL, 150.3 mmol), and 15.0 g (75.2 mmol) of the product of Example 6, Step A, the title compound was obtained as a tan solid (15.0 g), m.p. 112°–114° C. IR (nujol, cm-1),C=O (1696.9), NH (3237.4, 3307.9), triple bond (2125.6). $^1$H NMR (CDCl$_3$): δ9.25 (br,1H), 8.35–8.34 (d,1H), 7.16–7.14 (d,1H), 4.77 (s,2H), 3.42–39 (m,1H), 3.15–3.09 (m,1H), 2.81–2.75 (m,1H), 2.09–1.98 (m,1H), 1.80–1.40 (m,6H). Step C: Ethyl 2-[4-chloro-2-fluoro-5-[(2-propynyl)oxy]phenyl]octahydro-1-oxoimidazo[1,5-a]pyridine-3-carboxylate Using the procedure of Example 1, Step C and employing 13.62 g (73.62 mmol) of ethyl bromofluoroacetate, 10.18 g (73.62 mmol) of potassium carbonate, and 12.0 g (36.81 mmol) of the product of Example 6, Step B, the title compound was obtained as a white solid (4.24 g, upper R$_f$ product) and a yellow oil (6.2 g, lower R$_f$ product). Upper R$_f$ product: m.p. 72°–75° C. IR (nujol, $cm^{-1}$), C=O (1742.8), triple bond (2115.3). $^1$H NMR (CDCl$_3$, 400 MHz), δ7.35–7.33 (d,1H), 7.18–7.15 (d,1H), 4.91 (br s,1H), 4.75–4.74 (br s,2H), 4.20–4.09 (m,2H), 3.30–3.20 (d,1H), 2.98–2.90 (d,1H), 2.58 (s,1H), 2.55–2.43 (m,1H), 2.19–2.12 (m,1H), 1.98–1.89 (m,1H), 1.80–50 (m,3H), 1.40–1.31 (m,1H), 1.15–1.11 (t,3H). Lower R$_f$ product: IR (neat, cm-1), C=O (1736.6), triple bond (2115.5). $^1$H NMR (CDCl$_3$, 400 MHz), δ7.36–7.34 (d,1H), 7.22–7.19 (d,1H), 5.09 (s,1H), 4.75–4.74 (br s,1H), 4.22–4.21 (m,2H), 4.20–4.12 (m,1H), 3.60–3.53 (m,1H), 3.10–2.98 (m,1H), 2.75–2.65 (m,1H), 2.57 (s,1H), 2.15–2.00 (m,1H), 1.80–1.60 (m,3H), 1.50–1.40 (m,1H), 1.70–1.24 (t,3H).

EXAMPLE 7

2-[4-Chloro-2-fluoro-5-[(2-propynyl)oxy]phenyl]octahydro-1-oxoimidazol-[1,5-a]pyridine-3-carboxylic acid Using the procedure of Example 3 and employing 4.9 g (15.03 mmol) of the lower R$_f$ product of Example 6 and 1N NaOH (22.5 mL), the title compound was obtained as a white solid (4.13 g), m.p. 159°–161° C. IR (nujol, $cm^{-1}$), C=O (1722.5). $^1$H NMR spectrum was consistent with structure.

EXAMPLE 8

N-Butyl-2-[4-chloro-2-fluoro-5-[[(2-propynyl)oxy]phenyl]octahydro-1-oxoximidazol[1,5-a]pyridine-3-carboxamide A mixture of the product of Example 7 (400 mg, 1.34 mmol), N-butylamine (0.2 mL, 2.01 mmol), dicyclohexylcarbodiimide (457 mg, 2.22 mmol), and N,N4-dimethylaminopyridine (33.0 mg, 0.2 mmol) in methylene chloride (15 mL) under nitrogen was stirred at room temperature for about 72 h. The reaction mixture was then filtered and the solvent was evaporated under reduced pressure to produce a dry residue. Flash chromatography yielded the title compound as a white solid (142.0 mg), m.p. 136°–138° C. IR (nujol, cm$^{-1}$), C=O (1717.3), N—H (3301.0), triple bond (2120). $^1$H NMR (CDCl$_3$, 400 MHz), δ7.27–7.25 (d,1H), 7.22–7.19 (d,1H), 5.15–5.00 (br s,1H), 4.74–4.73 (br s,2H), 3.80–3.70 (br s,1H), 3.24–3.22 (m,2H), 3.18–3.09 (br s,1H), 2.98–2.89 (br1H), 2.58 (s,1H), 2.05–1.80 (br,2H), 1.73–1.70 (br,2H), 1.58–1.55 (br,3H), 1.48–1.46 (m,2H), 1.31–1.29 (m,2H), 0.92–0.88 (t,3H).

The following Tables illustrate the compounds of the invention that are produced by the processes of the invention.

The following abbreviations are used in the Tables which follow. All alkyl groups are the normal isomers unless indicated otherwise.

| | |
|---|---|
| t = tertiary | MeO = methoxy |
| s = secondary | Ph = phenyl |
| n = normal | CN = cyano |
| i = iso | Pr = propyl |
| Me = methyl | Et = ethyl |

TABLE 1

Compounds of Formula I wherein G = CH, W = O, Q = 2-F-4-Cl-5-(i-PrO)—Ph, R$^1$ = H, R$^2$ = CO$_2$Et

| A | B | A | B |
|---|---|---|---|
| CF$_3$ | CH$_3$ | CH$_2$CH$_3$ | n-butyl |
| CH$_2$OCH$_3$ | Cl(CH$_2$)$_4$ | Cl | CH$_2$CH=CHCH$_3$ |
| (CH$_2$)$_4$Cl | CH$_2$C≡CCH$_3$ | O(CH$_2$)$_3$CH$_3$ | CH$_2$CH$_3$ |
| SCH$_3$ | Cl(CH$_2$)$_4$ | | |
| —CHFCHFCH$_2$— | | —CH$_2$CH$_2$CH(CF$_3$)CH$_2$— | |
| —CH$_2$SCH$_2$CH$_2$— | | —CH$_2$CH$_2$S(O)$_2$CH$_2$CH$_2$— | |
| —CH$_2$N(CH$_3$)CH$_2$CH$_2$— | | —CH$_2$CH$_2$N[(CH$_2$)$_4$F]CH$_2$— | |
| —CH$_2$CHClCH$_2$CH$_2$— | | —CH$_2$C(Cl)=CHCH$_2$— | |
| —CH$_2$CH(C$_4$H$_9$)CH$_2$— | | —CH$_2$CH(F)CH$_2$— | |
| —CHClCH$_2$CH$_2$— | | | |

TABLE 2

Compounds of Formula I wherein Q = 4-ethyl-7-fluoro-3,4-dihydro-3-oxo-2H-1,4-benzoxazin-6-yl, R$^2$ = CO$_2$Me, R$^1$ = H

| A | B | G |
|---|---|---|
| CF$_3$ | CH$_3$ | CH |
| CF$_3$ | CH$_3$ | N |
| Et | n-butyl | CH |
| Et | n-butyl | N |
| O(CH$_2$)$_3$CH$_3$ | CH$_2$CH$_3$ | CH |
| (CH$_2$)$_3$CH$_3$ | (CH$_2$)$_4$Cl | CH |
| SCH$_2$CH$_2$CH$_3$ | CH$_2$CH=CHCH$_3$ | N |
| Et | n-butyl | C(CH$_3$) |
| CF$_3$ | CH$_3$ | C(C$_4$H$_9$) |
| —CH$_2$SCH$_2$CH$_2$— | | CH |
| —CH$_2$SCH$_2$CH$_2$— | | N |
| —CH$_2$CHFCHFCH$_2$— | | CH |
| —CH$_2$CHFCHFCH$_2$— | | N |
| —CH$_2$S(O)$_2$CH$_2$CH$_2$— | | CH |
| —CH$_2$S(O)$_2$CH$_2$— | | N |
| —CH$_2$N[(CH$_2$)$_4$F]CH$_2$CH$_2$— | | CH |
| —CH$_2$N[(CH$_2$)$_4$F]CH$_2$CH$_2$— | | N |
| —CH$_2$CH(CF$_3$)CH$_2$— | | CH |
| —CH$_2$CH(C$_2$H$_4$Cl)CH$_2$— | | CH |
| —CH$_2$CH(C$_2$H$_4$Cl)CH$_2$— | | N |
| —CH$_2$CH$_2$CHFCH$_2$— | | CH |
| —CH$_2$CHClCH$_2$CH$_2$— | | CH |

TABLE 3

Compounds of Formula I wherein W = O, R$^1$ = H, G = CH, A-B = —CH$_2$OCH$_2$CH$_2$—, Q = 2-F-4-Cl-5-(i-PrO)—Ph, R$^2$ =

| | | | |
|---|---|---|---|
| CCl$_3$ | CH$_2$O(2-Cl—Ph) | C(O)N(CH$_3$)(CH$_2$)$_3$CH$_3$ | C(O)N(Et)(4-Cl—Ph) |
| SO$_2$C$_3$H$_7$ | C(O)NHC$_3$H$_7$ | CH$_2$C(O)CH$_2$CH=CHCH$_3$ | C(O)NH(CH$_2$)$_5$CH$_3$ |
| CH$_2$CN | CH$_2$C(O)NH$_2$ | CH$_2$CH$_2$CO$_2$CH$_2$CH=CHCH$_3$ | C(O)CH$_2$CH$_2$CH$_2$ Cl |
| CH$_2$CH$_2$F | SO$_2$NHC$_2$H$_5$ | C(O)NH(4-OCH$_3$-3-Cl—Ph) | SO$_2$N(CH$_3$)(CH$_2$)$_5$CH$_3$ |
| CH$_2$CHCl$_2$ | C(O)(4-NO$_2$—Ph) | CH$_2$CH$_2$C(O)CH$_2$CH=CH$_2$ | CH$_2$CH$_2$CN |
| CF$_3$ | C(O)NHC$_6$H$_{11}$ | CN | |

TABLE 4

Compounds of Formula I wherein W = S, R$^1$ = H, G = N, A-B = —CH$_2$CH$_2$CH$_2$CH$_2$—, Q = 2-Cl-4-Cl-5-(HC≡CCH$_2$O)-phenyl, R$^2$ =

| | | | |
|---|---|---|---|
| CH$_2$CH$_2$O(CH$_2$)$_2$CH(CH$_3$)$_2$ | CO$_2$Me | CF$_3$ | CO$_2$(n-butyl) | CO$_2$(n-hexyl) |
| CO$_2$(4-NO$_2$-2-CH$_3$—Ph) | CH$_2$CH$_3$ | CN | CO$_2$(i-Pr) | CO$_2$CH$_2$CH=CHCH$_3$ |
| SO$_2$N(CH$_3$)[CH$_2$CH(Et)$_2$] | | | C(O)(4-F-Ph) | |

TABLE 5

Compounds of Formula I wherein W = S, $R^1$ = H, G = CH, A-B = —CH$_2$CH$_2$CH$_2$—, Q = 5,7-dichloro-2,3-dihydrobenzofuran-4-yl, $R^2$ =

| CO$_2$(n-pentyl) | C(O)NH$_2$ | C(O)NHCH$_2$CH$_2$CH(CH$_3$)$_2$ | C(O)N(CH$_3$)C$_6$H$_5$ |
|---|---|---|---|

TABLE 6

Compounds of Formula I wherein W = O, Q = 2-F-4-Cl-5-(i-PrO)—Ph, $R^1$ and $R^2$ are taken together to form =CHCO$_2$Et.

| G | A | B | G | A | B |
|---|---|---|---|---|---|
| N | CF$_3$CH$_2$ | CH(CH$_3$)$_2$ | CH | CH$_2$CH$_3$ | n-butyl |
| CH | CF$_3$CH$_2$ | CH(CH$_3$)$_2$ | N | S(CH$_2$)$_3$CH$_3$ | (CH$_2$)$_4$Cl |
| N | CH$_2$CH$_3$ | n-butyl | CH | S(CH$_2$)$_3$CH$_3$ | (CH$_2$)$_4$Cl |
| N | —CH$_2$OCH$_2$CH$_2$— | | N | —CH$_2$CH$_2$CH$_2$— | |
| CH | —CH$_2$OCH$_2$CH$_2$— | | CH | —CH$_2$CH=CHCH$_2$— | |
| N | —CH$_2$CH$_2$CH$_2$CH$_2$— | | CH | —CH$_2$S(O)$_2$CH$_2$CH$_2$— | |
| CH | —CH$_2$CH$_2$CH$_2$CH$_2$— | | H | —CH$_2$CHClCHClCH$_2$— | |
| CH | —CH$_2$N(CH$_3$)CH$_2$CH$_2$ | | | | |

TABLE 7

Compounds of Formula I wherein W = O, Q = 2-F-4-Cl—Ph, G = CH, $R^1$ and $R^2$ are taken together to form =C(CH$_3$)CON(C$_2$H$_5$)(2-Cl-4-MeO—Ph)

| A | B | A | B |
|---|---|---|---|
| CF$_3$ | Et | CH$_2$C≡CCH$_3$ | Cl(CH$_2$)$_4$ |
| i-Pr | CH$_2$Cl=CCH$_3$ | OCH$_2$CH$_2$CH$_3$ | n-propyl |
| —CH$_2$OCH$_2$CH$_2$— | | —CH$_2$CH(CH$_3$)CH$_2$— | |
| —CH$_2$CH$_2$CH$_2$CH$_2$— | | —CH$_2$CH(F)CH$_2$— | |
| —CH$_2$N(C$_3$H$_7$)CH$_2$CH$_2$— | | —CH$_2$S(O)$_2$CH$_2$CH$_2$— | |
| —CH$_2$CH$_2$CH$_2$— | | —CH$_2$CH(Cl)CH$_2$CH$_2$— | |
| —CH$_2$SCH$_2$CH$_2$— | | | |

TABLE 8

Compounds of Formula I wherein W = S, Q = 5,7-dichloro-2,3-dihydrobenzofuran-4-yl, G = CH, $R^1$ and $R^2$ are taken together to form =C(Et)CO$_2$C$_2$H$_5$

| A | B | A | B | A | B |
|---|---|---|---|---|---|
| CH$_2$CH$_2$Cl | i-Pr | CH$_2$CH$_2$S | CH$_3$ | CH$_2$CH$_2$CH=CH$_2$ | CH$_2$CH$_3$ |
| CH$_2$C≡CCH$_3$ | i-butyl | CH$_2$CF$_2$CF$_3$ | CH$_2$CF$_2$CF$_3$ | | |
| —CH$_2$OCH$_2$CH$_2$— | | —CH$_2$CH$_2$CH$_2$— | | —CH$_2$N(n-butyl)CH$_2$CH$_2$— | |
| —CH$_2$CH$_2$CH$_2$— | | —CH$_2$CHFCH$_2$— | | —CH$_2$CH(C$_2$H$_5$)CH$_2$— | |

TABLE 9

Compounds of Formula I wherein G = CH, $R^2$ = CO$_2$C$_2$H$_5$, Q = 4-Cl-2-F-5-(i-PrO)—Ph, A-B = —CH$_2$CH$_2$CH$_2$CH$_2$—,

| $R^1$ | W | $R^1$ | W | $R^1$ | W | $R^1$ | W | $R^1$ | W |
|---|---|---|---|---|---|---|---|---|---|
| CH$_3$ | O | CH$_3$ | S | F | O | F | S | Cl | O |
| Cl(CH$_2$)$_4$ | O | Cl(CH$_2$)$_4$ | S | n-butyl | O | n-butyl | S | Cl | S |

TABLE 10

Compounds of Formula I wherein G = CH, W = O, $R^2$ = C(O)N(Et)(4-NO$_2$—Ph), A-B = —CH$_2$OCH$_2$CH$_2$—, Q = 4-ethyl-7-fluoro-3,4-dihydro-3-oxo-2H-1,4-benzoxazin-6-yl, $R^1$ =

| F | Cl | Cl(CH$_2$)$_4$ | Br | CH$_3$ |
|---|---|---|---|---|

TABLE

Compounds of Formula I wherein W = O, $R^1$ = H, $R^2$ =—$CO_2Et$, A-B = —$CH_2OCH_2CH_2$—, Q = 2-$R^{11}$-4-$R^{13}$-5-$R^{12}$-Ph.

| $R^{11}$ | $R^{12}$ | $R^{13}$ | $R^{11}$ | $R^{12}$ | $R^{13}$ |
|---|---|---|---|---|---|
| F | $CH_3$ | Cl | F | C(O)N(Me)Et | Cl |
| F | n—$C_5H_{11}$ | Cl | F | $NO_2$ | Cl |
| F | Br | Cl | F | C(O)H | Cl |
| F | $CH(CH_3)C_2H_5$ | Cl | F | OH | Cl |
| F | $OC_3H_7$ | Cl | F | $N(CH_3(n-C_6H_{11})$ | Cl |
| F | $OCH[—(CH_2)_5—]$ | Cl | F | $NHSO_2NH(n-BUTYL)$ | Cl |
| F | $SO_2CH_2CH_2CH_3$ | Cl | F | 2-F—Ph | Cl |
| F | $C(O)CH_2CH(Cl)CH_3$ | Cl | F | 4-Me—O—Ph | Cl |
| F | $CO_2CH_2(4-Cl-2-F—Ph)$ | Cl | F | $CO_2N=C[—(CH_2)_5—]$ | Cl |
| F | $CH_2CH(Cl)CO_2CH_2C\equiv CCH_3$ | Cl | F | $C(CH_3)=N—OC_3H_7$ | Cl |
| F | $NHSO_2CH_2CH_2CH(CH_3)_2$ | $SCH_3$ | F | $NO_2$ | $OCHF_2$ |
| F | $CH=C(CH_3)CO_2Et$ | CN | F | $S(O)_2CH_2CH_2CH(CH_3)_2$ | $NO_2$ |
| F | $NHSO_2CH_3$ | $CH_2CH_2Cl$ | Cl | $OCH_2C\equiv CCH_2OCH_3$ | Cl |
| Cl | $CO_2(n-C_8H_{17})$ | Cl | Cl | $OCH_2Si(CH_3)_3$ | Cl |
| Cl | Cn | Cl | Cl | SH | Cl |
| Cl | $C(O)N(—CH_2CH_2OCH_2CH_2—)$ | Cl | Cl | $NHSO_2CH_2CH_2CH_3$ | Cl |
| Cl | $O[4-CH_2CH(—OCH_2CH_2O—)—Ph]$ | Cl | Br | $NH_2$ | Cl |
| Br | $CO_2CH_2CH(CH_3)_2$ | Cl | Br | $NH_2$ | Cl |
| Br | $OCH_2CH_2CO_2(n-propyl)$ | Cl | Br | Cl | $OCH_3$ |
| Br | $CH=C(Cl)CO_2CH_2SCH_2C\equiv CH$ | Cl | Br | $CF_3$ | Et |
| Br | $C(O)S(CH_2)_4CH_3$ | CN | Br | $CH_2SO_2CH_3$ | $NO_2$ |
| Br | $CH_3$ | $NO_2$ | Br | $NO_2$ | $NO_2$ |

TABLE 12

Compounds of Formula I wherein W = O, $R^1$ = H, $R^2$=$CO_2Me$, A–B =—$CH_2CH_2CH_2$—, Q = (structure with $R^{11}$, $R^{14}$, $R^{15}$, $R^{16}$)

| $R^{11}$ | $R^{14}$ | $R^{15}$ | $R^{16}$ |
|---|---|---|---|
| F | $CH_3$ | $CH_2CH_3$ | $CH_3$ |
| F | H | $CH_3$ | $CH_2CH_3$ |
| F | Cl | CN | $CH_2CH(CH_3)_2$ |
| F | $CH(CH_3)_2$ | cyclopropyl | $CH_2CHClCH_2CH(CH_3)_2$ |
| F | F | H | $CH_2CH_2OCH_2CH_3$ |
| F | n-propyl | $CH_2OH$ | $CH(CH_3)CO_2CH_3$ |
| F | H | H | n-hexyl |
| F | $CH_3$ | $C(O)N(CH_3)Et$ | $CH(CH_3)C\equiv CCH_2CH_3$ |
| F | $CH_3$ | H | $n-C_6H_{13}$ |
| Cl | H | H | $CH(CH_3)CN$ |
| Cl | $CH_3$ | $C\equiv CH$ | $CH_2CH_2CH=CHCH_3$ |
| Br | H | H | Me |
| Br | n-propyl | n-propyl | $CH_2C\equiv CCH(CH_3)_2$ |
| F | Cl | Cl | $CH_2CH_2OCH(CH_3)_2$ |
| F | H | H | $CH_2CH$—$CH_2$ (epoxide) |

TABLE 13

Compounds of Formula I wherein: W = S, $R^1$ = H, $R^2$ = $CH_2CH_2Cl$, A = $CH_2CH(CH_3)_2$, B = $CH_2CH_2CH_3$, G = CH, Q = (structure with $R^{11}$, $R^{13}$, $R^{14}$, $R^{15}$)

| $R^{13}$ | $R^{14}$ | $R^{15}$ | $R^{11}$ |
|---|---|---|---|
| Cl | H | H | F |
| Cl | i-Pr | Et | F |
| Cl | Me | 2-Cl—Ph | F |
| Cl | Et | $n-C_6H_{11}$ | F |
| Me | n-butyl | $CH_2CH=CHCH_3$ | F |
| Et | n-Pr | cyclopentyl | Cl |
| $Cl(CH_2)_4$ | Me | cyclopentyl | Cl |
| H | n-butyl | Ph | Cl |
| Br | H | Me | Cl |
| F | Me | Me | Br |
| F | Et | i-Pr | Br |
| n-butyl | H | H | Br |
| i-Pr | Me | 4-CN—Ph | I |
| Cl | Et | i-Pr | I |
| Cl | Et | 3-$NO_2$—Ph | I |

TABLE 14

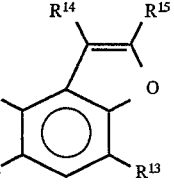

Compounds of Formula I wherein
W = O, $R^1$ = H, $R^2$ = $CONH_2$,
A–B = —$CH_2CH_2CH_2CH_2$—, Q =

| $R^{11}$ | $R^{13}$ | $R^{14}$ | $R^{15}$ | $R^{11}$ | $R^{13}$ | $R^{14}$ | $R^{15}$ |
|---|---|---|---|---|---|---|---|
| F | Cl | Me | $CH_2CH_2CH_3$ | F | $OCH_3$ | Et | $CH_2CH_2Cl$ |
| F | $NO_2$ | H | H | Cl | $OCHF_2$ | Me | Me |
| Cl | Cl | n-Pr | $CO_2Et$ | Cl | Br | H | H |

TABLE 15

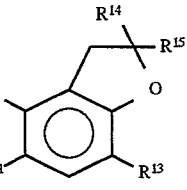

Compounds of Formula I wherein:
W = S, R = H, $R^2$ = $CO_2$n-butyl,
A–B = —$CH_2CH_2CH_2CH_2$—, Q =

| $R^{11}$ | $R^{13}$ | $R^{14}$ | $R^{15}$ | $R^{11}$ | $R^{13}$ | $R^{14}$ | $R^{15}$ |
|---|---|---|---|---|---|---|---|
| Br | $OCH_3$ | H | Me | Cl | $SCH_3$ | n-Pr | Et |
| F | Cl | $CH_3$ | $CO_2CH_2CH(CH_3)_2$ | Cl | Cl | $CH_3$ | Cl≡CH |

TABLE 16

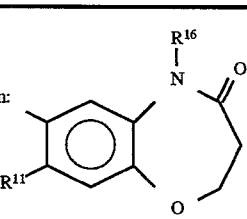

Compounds of Formula I wherein:
W = O,
$R^2$ = $CONHCH_2CH(CH_3)_2$,
$R^1$ = Me, A = $CH_2CF_2CF_3$,
B = ethyl, G = N, Q =

| $R^{11}$ | $R^{16}$ | $R^{11}$ | $R^{16}$ |
|---|---|---|---|
| F | $CH_2CH(CH_3)_2$ | F | $CH(CH_3)CN$ |
| F | $CH(CH_3)(CO_2CH_3)$ | F | $CH_2CH_2C≡CCH_2CH_3$ |
| F | $CH_2CH(CH_3)CH_2CH_3$ | F | $(CH_2)_4Cl$ |
| F | n-$C_6H_{13}$ | F | H |
| Cl | $CH_2CH_2OCH_2CH_2CH_3$ | Cl | $CH_2CH=CHCH_2CH_3$ |
| Cl | H | Cl | $CH_3$ |
| Br | Et | Br | n-butyl |
| Br | i-Pr | I | $CH_2C≡CH$ |
| I | $CH(CH_3)C≡CCH_3$ | I | H |

TABLE 17

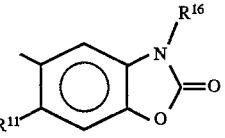

Compounds of Formula I wherein:
W = O, G = CH,
A = $CH_2C≡CCH_3$, B = $CH_3$,
$R^1$ and $R^2$ are taken together
to form =$C(C_2H_5)CO_2Et$, Q =

| $R^{11}$ | $R^{16}$ | $R^{11}$ | $R^{16}$ |
|---|---|---|---|
| F | H | F | Me |
| F | n-butyl | F | $CH_2CH=CHCH_3$ |
| Cl | H | Cl | $(CH_2)_4Cl$ |
| Cl | $CH_2CH(CH_2CH_3)C_2H_5$ | Br | H |
| Br | $CH(CH_3)CN$ | I | $CH_2CF_3$ |
| I | $CH_2CH_2OCH_2CH(CH_3)_2$ | | |

TABLE 18

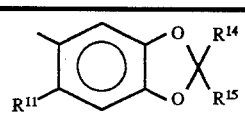

Compounds of Formula I
wherein: W = O, $R^1$ = H,
$R^2$ = $CO_2$(i-Pr), G = CH, Q =
A–B = —$CH_2CH_2CH_2CH_2$—

| $R^{11}$ | $R^{14}$ | $R^{15}$ | $R^{11}$ | $R^{14}$ | $R^{15}$ |
|---|---|---|---|---|---|
| F | Me | cyclopropyl | F | Et | $(CH_2)_4Cl$ |
| F | H | $C(O)CH_2CH_3$ | Cl | H | $CH_2CN$ |
| Cl | i-Pr | $CH_2CO_2$(n-butyl) | Br | Et | C≡CH |

Formulation/Utility of Compounds of Formula I

The compounds of Formula I are useful as herbicides in agriculture. To carry out this utility, any of the compounds of Formula I can generally be used in formulation with an agriculturally suitable carrier comprising a liquid or solid diluent or an organic solvent. Use formulations include dusts, granules, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

|  | Weight Percent | | |
| --- | --- | --- | --- |
|  | Active Ingredient | Diluent | Surfactant |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et at., *Handbook of Insecticide Dust Diluents and Carriers*, 2nd Ed., Dorland Books, Caldwell, N.J. Typical liquid diluents and solvents are described in Marsden, *Solvents Guide*, 2nd Ed., Interscience, N.Y., 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth, etc.

Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., *Pesticide Formulations*, Washington, D.C., (1988), pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, (1963), pp 8–57 and following, and WO 91/13546. Pellets can be prepared as described in U.S. Pat. No. 4,172,714. Water-dispersible and water-soluble granules can also be prepared as taught in DE 3,246,493.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, (1961), pp 81–96; and Hance et at., *Weed Control Handbook*, 8th Ed., Blackwell Scientific Publications, Oxford, (1989).

In the following Examples, all percentages are by weight and all formulations are worked up in conventional ways. Compound 1 refers to the compound listed in Index Table A hereinafter.

EXAMPLE A

| High Strength Concentrate | |
| --- | --- |
| Compound 1 | 98.5% |
| silica aerogel | 0.5% |
| synthetic amorphous fine silica | 1.0%. |

EXAMPLE B

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE C

| Granule | |
| --- | --- |
| Compound 1 | 10.0% |
| attapulgite granules (low volative matter, 0.71/0.30 mm; U.S.S. No. 25–50 sieves) | 90.0%. |

EXAMPLE D

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Tests results indicate that the compounds of Formula I are highly active preemergent and/or postemergent herbicides and/or plant growth regulants. Many of them have utility for broad-spectrum pre- and/or postemergence weed control in areas where complete control of all vegetation is desired such as around fuel storage tanks, industrial storage areas, parking lots, drive-in theaters, around billboards and highway and railroad structures. Some of the compounds are useful for the control of selected grass and broadleaf weeds such as morningglory, cocklebur, velvetleaf, giant foxtail, barnyardgrass and lambsquarters, with tolerance to important agronomic crops which include but are not limited to wheat, corn, soybeans and rice. Those skilled in the art will appreciate that not all compounds are equally effective against all weeds. Alternatively, the subject compounds are useful to modify plant growth.

Compounds of Formula I can be used alone or in combination with other commercial herbicides, insecticides or fungicides. A mixture of one or more of the following herbicides with a compound of Formula I may be particularly useful for weed control. Examples of other herbicides with which compounds of this invention can be formulated are: acetochlor, acifluoffen, acrolein, 2-propenal, alachlor, ametryn, amidosulfuron, ammonium sulfamate, amitrole, anilofos, asulam, atrazine, barban, benerin, bensulfuron methyl, bensulide, bentazon, benzofluor, benzoylprop, bifenox, bromacil, bromoxynil, bromoxynil heptanoate, bromoxynil octanoate, butachlor, buthidazole, butralin, butylate, cacodylic acid, 2-chloro-N,N-di-2-propenylacetamide, 2-chloroallyl diethyldithiocarbamate, chloramben, chlorbromuron, chloridazon, chlorimuron ethyl, chlormethoxynil, chlornitrofen, chloroxuron, chlorpropham, chlorsulfuron, chlortoluron, cinmethylin, cinosulfuron, clethodim, clomazone, cloproxydim, clopyralid, calcium salt of methylarsonic acid, cyanazine, cycloate, cycluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichlobenil, dichlorprop, diclofop, diethatyl, difenzoquat, diflufenican, dimepiperate, dinitramine, dinoseb, diphenamid, dipropetryn, diquat, diuron, 2-methyl-4,6-dinitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fenuron, salt of fenuron and trichloroacetic acid, flamprop, fluazifop, fiuazifop-P, fluchloralin, flumesulam, flumipropyn, fluometuron, fluorochloridone, fluorodifen, fluoroglycofen, flupoxam, fluridone, fluroxypyr, fluzasulfuron, fomesafen, fosamine, glyphosate, haloxyfop, hexaflurate, hexazinone, imazamethabenz, imazapyr, imazaquin, imazamethabenz methyl, imazethapyr, imazosulfuron, ioxynil, isopropalin, isoproturon, isouron, isoxaben, karbutilate, lactofen, lenacil, linuron, metobenzuron, metsulfuron methyl, methylarsonic acid, monoammonium salt of methylarsonic acid, (4-chloro-2-methylphenoxy)acetic acid, S,S'-dimethyl-2-(difluoromethyl)-4-(2-methylpropyl)-6-(trifluoromethyl)-3,5-pyridinedicarbothioate, mecoprop, mefenacet, mefluidide, methalpropalin, methabenzthiazuron, metham, methazole, methoxuron, metolachlor, metribuzin, 1,2-dihydropyridazine-3,6-dione, molinate, monolinuron, monuron, monuron salt and trichloroacetic acid, monosodium salt of methylarsonic acid, napropamide, naptalam, neburon, nicosulfuron, nitralin, nitrofen, nitrofluorfen, norea, norflurazon, oryzalin, oxadiazon, oxyfluorfen, paraquat, pebulate, pendimethalin, perfluidone, phenmedipham, picloram, 5-[2-chloro-4-(trifluoromethyl) phenoxy]-2-nitroacetophenone oxime-O-acetic acid methyl ester, pretilachlor, primisulfuron, procyazine, profluralin, prometon, prometryn, pronamide, propachlor, propanil, propazine, propham, prosulfalin, prynachlor, pyrazolate, pyrazon, pyrazosulfuron ethyl, quinchlorac, quizalofop ethyl, rimsulfuron, secbumeton, sethoxydim, siduron, simazine, 1-(α,α-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, tri-allate, trialkoxydim, triasulfuron, tribenuron methyl, triclopyr, tridiphane, trifluralin, trimeturon, (2,4-dichlorophenoxy)acetic acid, 4-(2,4-dichlorophenoxy)butanoic acid, vernolate, and xylachlor.

In certain instances, combinations with other herbicides having a similiar spectrum of control but a different mode of action will be particularly advantageous for resistance management.

A herbicidally effective amount of the compounds of Formula I is determined by a number of factors. These factors include: formulation selected, method of application, amount and type of vegetation present, growing conditions, etc. In general, a herbicidally effective amount of a compound(s) of Formula I is applied at rates from about 0.01 to 20 kg/ha with a preferred rate range of 0.02 to 10 kg/ha. One skilled in the art can easily determine application rates necessary for the desired level of weed control.

The following Tests demonstrate the control efficacy of the compounds of Formula I against specific weeds. The weed control afforded by the compounds is not limited, however, to these species. See Index Tables A–J for compound descriptions. The following footnotes are used in the Tables below:

[a] single diastereomer, mixture of enantiomers, upper $R_f$ product
[b] single diastereomer, mixture of enantiomers, lower $R_f$ product
[c] mixture of diastereomers
[d] $^1$H NMR data for oils given in Index Table J
[e] racemic mixture
[f] single diastereomer "Upper $R_f$" and "lower $R_f$" refer to relative values using silica gel thin layer chromatography. "Config." refers to the configuration at the indicated chiral center(s).

INDEX TABLE A

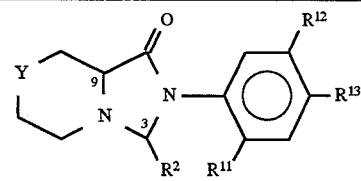

| Cmpd No. | Y | $R^2$ | $R^{11}$ | $R^{12}$ | $R^{13}$ | m.p. (°C.)[d] | Comments |
|---|---|---|---|---|---|---|---|
| 1 | $CH_2$ | $CO_2Et$ | F | H | Cl | 113–114 | a |
| 2 | $CH_2$ | $CO_2Et$ | F | H | Cl | oil | b |
| 3 | $CH_2$ | $CO_2Et$ | F | H | F | 100–101 | 1 isomer, 9S config. |
| 4 | $CH_2$ | $CO_2Et$ | F | H | F | oil | 1 isomer, 9R config. |
| 5 | $CH_2$ | $CO_2H$ | F | H | Cl | 170–172 | a |
| 6 | $CH_2$ | $CO_2Et$ | F | O-iPr | Cl | 83–85 | a |
| 7 | $CH_2$ | $CO_2Et$ | Cl | O-iPr | Cl | oil | b |
| 9 | $CH_2$ | $CO_2Et$ | Cl | $OCH_2C\equiv CH$ | Cl | 320(dec) | c |
| 10 | $CH_2$ | $CO_2Et$ | Cl | $OCH_2C\equiv CH$ | Cl | 120–121 | a |
| 11 | $CH_2$ | $CO_2Et$ | Cl | $OCH_2C\equiv CH$ | Cl | 121–122 | b |
| 12 | $CH_2$ | $CO_2Et$ | Cl | H | Cl | oil | c |
| 14 | $CH_2$ | $CO_2Me$ | Cl | H | Cl | oil | c |

INDEX TABLE A-continued

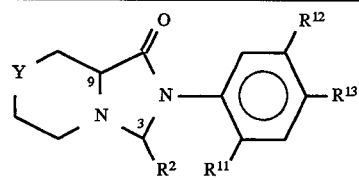

| Cmpd No. | Y | $R^2$ | $R^{11}$ | $R^{12}$ | $R^{13}$ | m.p. (°C.)[d] | Comments |
|---|---|---|---|---|---|---|---|
| 16 | $CH_2$ | $CO_2Et$ | Cl | $CO_2Me$ | Cl | oil | c |
| 17 | $CH_2$ | $CO_2Et$ | H | OMe | Cl | oil | c |
| 18 | $CH_2$ | $CO_2Et$ | Cl | O-iBu | Cl | oil | a |
| 19 | $CH_2$ | $CO_2Et$ | Cl | O-iBu | Cl | oil | b |
| 20 | $CH_2$ | $CO_2Et$ | Cl | O-iPr | Cl | oil | b |
| 21 | $CH_2$ | $CO_2Et$ | Cl | O-iPr | Cl | oil | a |
| 22 | O | $CO_2Et$ | F | O-iPr | Cl | oil | b |
| 23 | $CH_2$ | $CH_2OH$ | Cl | O-iPr | Cl | oil | a |
| 30 | $CH_2$ | $CO_2Et$ | F | O-iPr | Cl | oil | 3S, 9R config. |
| 31 | $CH_2$ | $CO_2Et$ | F | O-iPr | Cl | oil | 3R, 9R config. |
| 32 | $CH_2$ | $CO_2Et$ | F | O-iPr | Cl | oil | 3R, 9S config. |
| 33 | $CH_2$ | $CO_2Et$ | F | O-iPr | Cl | oil | 3S, config. |
| 36 | O | $CO_2Et$ | F | $OCH_2C\equiv CH$ | Cl | oil | a |
| 37 | O | $CO_2Et$ | F | $OCH_2C\equiv CH$ | Cl | oil | b |
| 38 | O | $CO_2Et$ | F | O-iBu | Cl | oil | a |
| 39 | O | $CO_2Et$ | F | O-iBu | Cl | oil | b |
| 40 | $CH_2$ | $CO_2Me$ | Cl | O-iPr | Cl | oil | a |
| 41 | $CH_2$ | $CO_2Me$ | Cl | O-iPr | Cl | oil | b |
| 42 | $CH_2$ | $CO_2(nBu)$ | Cl | O-iPr | Cl | oil | c |
| 43 | $CH_2$ | $CO_2(iPr)$ | Cl | O-iPr | Cl | oil | c |
| 44 | $CH_2$ | $CO_2H$ | F | O-iPr | Cl | 150–152 | a |
| 45 | $CH_2$ | $CO_2H$ | F | O-iPr | Cl | 136–138 | b |
| 46 | $CH_2$ | $CO_2(CH_2Ph)$ | F | O-iPr | Cl | 64–66 | b |
| 47 | $CH_2$ | $CO_2(CH_2Ph)$ | F | O-iPr | Cl | 99–101 | a |
| 48 | $CH_2$ | $CO_2(nBu)$ | F | O-iPr | Cl | oil | b |
| 49 | $CH_2$ | $CO_2(nBu)$ | F | O-iPr | Cl | oil | a |
| 50 | $CH_2$ | $CO_2(iBu)$ | F | O-iPr | Cl | oil | b |
| 51 | $CH_2$ | $CO_2(iBu)$ | F | O-iPr | Cl | oil | a |
| 52 | $CH_2$ | $CO_2(nPr)$ | F | O-iPr | Cl | oil | b |
| 53 | $CH_2$ | $CO_2(nPr)$ | F | O-iPr | Cl | 71–73 | a |
| 54 | $CH_2$ | $CO_2(iPr)$ | F | O-iPr | Cl | oil | b |
| 55 | $CH_2$ | $CO_2(iPr)$ | F | O-iPr | Cl | 107–109 | a |
| 56 | $CH_2$ | $CO_2Me$ | F | O-iPr | Cl | oil | b |
| 57 | $CH_2$ | $CO_2Me$ | F | O-iPr | Cl | 97–99 | a |
| 58 | $CH_2$ | $CO_2(CH_2)_2CH(Me)_2$ | F | O-iPr | Cl | oil | b |
| 59 | $CH_2$ | $CO_2(CH_2)_2CH(Me)_2$ | F | O-iPr | Cl | oil | a |
| 70 | O | COOH | F | O-iPr | Cl | 59–61 | a |
| 71 | O | COOH | F | O-iPr | Cl | 62–64 | b |
| 72 | O | $CO_2(CH_2)_2CH(Me)_2$ | F | O-iPr | Cl | oil | b |
| 75 | $CH_2$ | $CO_2(CH_2Ph)$ | F | $OCH_2C\equiv CH$ | Cl | oil | b |
| 76 | $CH_2$ | $CO_2(CH_2Ph)$ | F | $OCH_2C\equiv H$ | Cl | oil | a |
| 77 | $CH_2$ | $CO_2Me$ | F | $OCH_2C\equiv CH$ | Cl | oil | b |
| 78 | $CH_2$ | $CO_2(CH_2)CH(Me)_2$ | F | $OCH_2C\equiv CH$ | Cl | 103–105 | a |
| 79 | $CH_2$ | COOH | F | $OCH_2C\equiv CH$ | Cl | 162–164 | a |
| 80 | $CH_2$ | COOH | F | $OCH_2C\equiv CH$ | Cl | 159–161 | b |
| 81 | $CH_2$ | $CO_2(CH_2)_2CH(Me)_2$ | F | $OCH_2C\equiv CH$ | Cl | oil | b |
| 82 | $CH_2$ | $CO_2(nBu)$ | F | $OCH_2C\equiv CH$ | Cl | 65–67 | a |
| 83 | $CH_2$ | $CO_2(nBu)$ | F | $OCH_2C\equiv CH$ | Cl | 90–92 | b |
| 84 | $CH_2$ | $CO_2(iPr)$ | F | $OCH_2C\equiv CH$ | Cl | 76–78 | b |
| 85 | $CH_2$ | $C(=O)NH(n-Bu)$ | F | $OCH_2C\equiv CH$ | Cl | 136–138 | b |
| 86 | $CH_2$ | $CO_2(iPr)$ | F | $OCH_2C\equiv CH$ | Cl | oil | a |
| 87 | $CH_2$ | $C(=O)NHEt$ | F | $OCH_2C\equiv CH$ | Cl | 141–143 | b |
| 88 | O | $CO_2CH_2C\equiv CH$ | F | O-iPr | Cl | 92–97 | b |

INDEX TABLE A-continued

| Cmpd No. | Y | $R^2$ | $R^{11}$ | $R^{12}$ | $R^{13}$ | m.p. (°C.)$^d$ | Comments |
|---|---|---|---|---|---|---|---|
| 89 | O | $CO_2CH_2C\equiv H$ | F | $OCH_2C\equiv CH$ | Cl | oil | |
| 90 | O | $CO_2CH_2C\equiv CH$ | F | $OCH_2C\equiv CH$ | Cl | oil | b |
| 91 | O | $CO_2H$ | F | $OCH_2C\equiv CH$ | Cl | 66–68 | a |
| 92 | O | $CO_2H$ | F | $OCH_2C\equiv CH$ | Cl | 85–87 | b |
| 93 | $CH_2$ | $CO_2Et$ | Cl | CONHiPr | Cl | 60–63 | c |
| 94 | O | $CO_2Et$ | F | $OCH(Me)C\equiv CH$ | Cl | oil | b |
| 95 | O | $CO_2Et$ | F | O-iPr | Cl | oil | a |
| 97 | O | $CO_2Et$ | F | $OCH(Me)C\equiv CH$ | Cl | 132–134 | c |
| 98 | O | $CO_2Et$ | F | $OCH(Me)C\equiv CH$ | Cl | 95–97 | c |
| 99 | O | $CO_2(iPr)$ | F | $OCH(Me)C\equiv CH$ | Cl | 99–101 | b |
| 101 | O | $CO_2Et$ | F | $CO_2Me$ | Cl | 95–97 | a |
| 102 | O | $CO_2Et$ | F | $CO_2Me$ | Cl | 98–100 | b |

INDEX TABLE B

| Cmpd No. | $R^2$ | $R^{11}$ | $R^{12}$ | $R^{13}$ | m.p. (°C.)$^d$ | Comments |
|---|---|---|---|---|---|---|
| 24 | $CO_2Et$ | F | H | Cl | oil | 1 diastereomer, lower $R_f$ |
| 25 | $CO_2Et$ | F | H | Cl | oil | 1 diastereomer, upper $R_f$ |

INDEX TABLE D

| Cmpd No. | $R^2$ | m.p. (°C.)$^d$ | Stereochemistry |
|---|---|---|---|
| 26 | $CO_2Et$ | oil | 3S, 9S config. |
| 27 | $CO_2Et$ | oil | 3R, 9S config. |
| 28 | $CO_2Et$ | oil | 3S, 9R config. |
| 29 | $CO_2Et$ | oil | 3R, 9R config. |
| 60 | $CO_2H$ | 69–71 | a |
| 61 | $CO_2H$ | 99–101 | b |
| 62 | $CO_2(CH_2Ph)$ | oil | b |

INDEX TABLE C

| Cmpd No. | $R^2$ | $R^{12}$ | m.p. (°C.)$^d$ | Comments |
|---|---|---|---|---|
| 13 | $CO_2Et$ | H | 97–99 | 9R config., upper $R_f$ diastereomer |
| 8 | $CO_2Et$ | H | 133–135 | 9S config., lower $R_f$ diastereomer |
| 15 | $CO_2Et$ | $OCH_2C\equiv CH$ | 78–81 | c |

INDEX TABLE D-continued

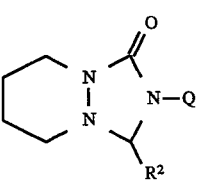

| Cmpd No. | R² | m.p. (°C.)ᵈ | Stereochemistry |
|---|---|---|---|
| 63 | CO₂(CH₂Ph) | oil | a |
| 64 | CO₂(nBu) | oil | a |
| 65 | CO₂(nBu) | oil | b |
| 66 | CO₂(CH₂)₂CH(Me)₂ | oil | a |
| 67 | CO₂CH₂CH(Me)₂ | oil | b |
| 68 | CO₂CH₂CH(Me)₂ | oil | a |
| 69 | CO₂CH(Me)₂ | oil | a |
| 73 | CO₂Me | oil | a |
| 74 | CO₂(CH₂)₂CH(Me)₂ | oil | b |

INDEX TABLE E

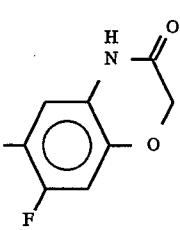

| Cmpd No. | R¹² | m.p. (°C.)ᵈ | Comments |
|---|---|---|---|
| 34 | OiPr | oil | a |
| 35 | OiPr | oil | b |
| 96 | OCH₂C≡CH | 130–132 | b |

INDEX TABLE F

| Cmpd No. | R² | Q | m.p. (°C.)ᵈ | Comments |
|---|---|---|---|---|
| 100 | CO₂Et | (structure) | 59–61 | e |
| 103 | CO₂Et | 4-chloro-2-fluoro-5-(2-propyloxy)phenyl | oil | e |
| 104 | CO₂Et | (structure) | 82–84 | e |

INDEX TABLE F-continued
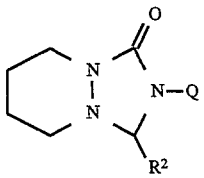
| Cmpd No. | R² | Q | m.p. (°C.)[d] | Comments |
|---|---|---|---|---|
| 105 | CO₂Et | 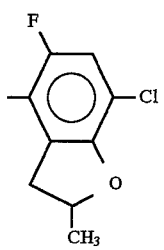 | 56–58 | c |
| 106 | CO₂Et | 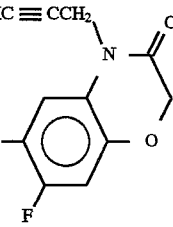 | 48–50 | e |
| 107 | CO₂Et | 4-chloro-2-fluoro-5-carboethoxy-phenyl | 121–123 | e |
| 108 | CO₂H | 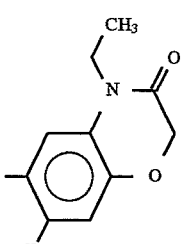 | 106–109 | e |
| 118 | CO₂Et | 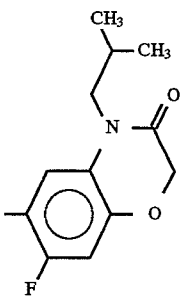 | 55–57 | e |

INDEX TABLE G

| Cmpd No. | O | m.p. (°C.)[d] | Comments |
|---|---|---|---|
| 111 | (structure: morpholine-N-N-C(=O)-N linked to fluorophenyl with N-ethyl acetamide and O-CH2 ring, CH(CO2Et)) | 137–139 | e |

INDEX TABLE H (General structure: bicyclic ring with A–B bridge, N, C(=O)–N–Q, and CH–CO2Et)

| Cmpd No. | A-B | O | m.p. (°C.)[d] | Comments |
|---|---|---|---|---|
| 109 | —CH₂OCH₂CH₂— | (N-ethyl, methyl-fluorophenyl, O-CH2-C(=O) ring) | 48–50 | a |
| 110 | —CH₂OCH₂CH₂— | (N-ethyl, methyl-fluorophenyl, O-CH2-C(=O) ring) | 59–61 | b |
| 116 | —CH₂OCH₂CH₂— | (N-isobutyl, methyl-fluorophenyl, O-CH2-C(=O) ring) | 79–81 | b |

INDEX TABLE H-continued
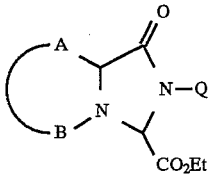
| Cmpd No. | A-B | Q | m.p. (°C.)[d] | Comments |
|---|---|---|---|---|
| 117 | —CH₂OCH₂CH₂— | 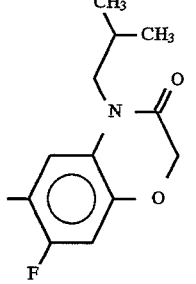 | 116–118 | a |
| 119 | —CH₂CH₂CH₂— | 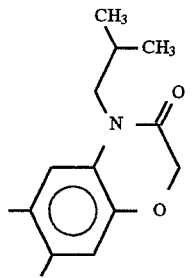 | 137–139 | b |
| 120 | —CH₂CH₂CH₂— | 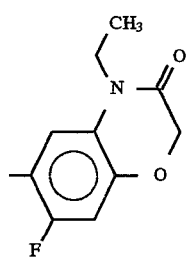 | 56–58 | a |
| 121 | —CH₂CH₂CH₂— | 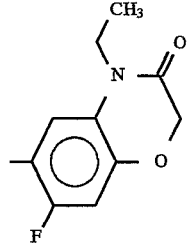 | 129–131 | b |
| 122 | —CH₂CH₂CH₂— |  | oil | a |

INDEX TABLE H-continued

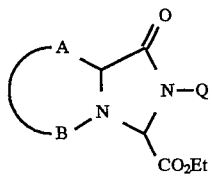

| Cmpd No. | A-B | Q | m.p. (°C.)[d] | Comments |
|---|---|---|---|---|
| 123 | —CH$_2$CH$_2$OCH$_2$— | 2-F-4-Cl—Ph | 58–60 | a |
| 124 | —CH$_2$CH$_2$OCH$_2$— | 2-F-4-Cl—Ph | 118–120 | b |

INDEX TABLE I

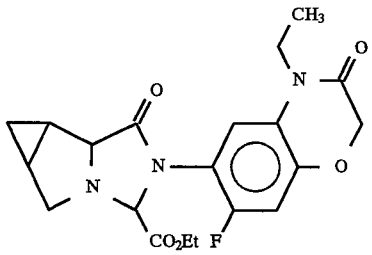

| Cmpd No. | m.p. (°C.)[d] | Comments |
|---|---|---|
| 112 | 181–183 | f |
| 113 | 50–52 | f |
| 114 | 56–58 | f |
| 115 | 52–54 | f |

TABLE J

Index

| Cmpd No. | $^1$H NMR Data[1] |
|---|---|
| 2 | 7.49–7.47 (m, 1H), 7.17–7.15 (m, 2H), 4.88 (s, 1H), 1.38–1.10, (t, 3H). |
| 4 | 5.11 (s, 1H), 4.22–4.20 (q, 2H), 1.28–1.24 (t, 3H). |
| 7 | 7.44 (s, 1H), 6.97 (s, 1H), 5.14 (s, 1H), 4.49–4.42 (m, 1H), 4.21–4.19 (m, 2H), 1.38–1.34 (m, 6H), 1.27–1.24 (t, 3H). |
| 12 | 5.19 (s, 1H), 4.98 (s, 1H), 4.30–4.02 (m, 2H), 1.23 (t, 3H), (t, 3H). |
| 14 | 5.19 (s, 1H), 4.99 (s, 1H), 4.30–4.15 (m, 4H), 1.25 (t, 3H), 1.08 (t, 3H). |
| 16 | 7.96–7.94 (d, 1H), 7.60–7.57 (d, 1H), 5.19 (s, 1H), 4.98 (s, 1H), 3.91 (s, 3H), 1.27 (t, 3H), 1.18 (t, 3H). |
| 17 | 5.19 (s, 1H), 4.98 (s, 1H), 4.31 4.12 (m, 4H), 3.90 (s, 3H), 1.35–1.29 (t, 3H), 1.19–1.11 (t, 3H). |
| 18 | 7.41 (s, 1H), 6.98 (s, 1H), 4.95 (s, 1H), 4.20–4.15 (m, 2H), 3.80–3.75 (m, 2H), 1.17–1.14 (t, 3H), 1.04–1.03 (d, 6H). |
| 19 | 7.44 (s, 1H), 6.92 (s, 1H), 5.14 (s, 1H), 4.21–4.15 (m, 2H), 3.80–3.75 (m, 2H), 1.28–1.25 (t, 3H), 1.04–1.03 (d, 6H). |
| 20 | 7.44 (s, 1H), 6.97 (s, 1H), 5.12 (s, 1H), 4.60–4.53 (m, 1H), 4.20–4.15 (m, 2H), 1.38–1.34 (dd, 6H), 1.27–1.24 (t, 3H). |
| 21 | 7.41 (s, 1H), 7.02 (s, 1H), 4.9 (s, 1H), 4.60–4.53 (m, 1H), 4.20–4.15 (m, 2H), 1.56–1.37 (dd, 6H), 1.17–1.13 (t, 3H). |
| 22 | 7.26–7.17 (dd, 2H), 5.00 (s, 1H), 1.39–1.35 (dd, 6H), 1.29–1.25 (t, 3H). |
| 23 | 9.40 (br, 1H), 7.40 (s, 1H), 7.28 (s, 1H), 1.39–1.38 (d, 6H). |
| 24 | 6.97–6.96 (d, 1H), 5.30–5.07 (m, 2H), 4.22–4.18 (m, 2H), 1.29–1.25 (m, 3H). |
| 25 | 6.93–6.92 (d, 1H), 5.11–5.05 (m, 1H), 4.99 (s, 1H), 4.22–4.11 (m, 2H), 1.56–1.54 (d, 3H), 1.80–1.63 (t, 3H). |

TABLE J-continued

Index

| Cmpd No. | $^1$H NMR Data[1] |
|---|---|
| 26 | 7.21–7.19 (d, 1H), 7.13–7.12 (d, 1H), 5.14 (s, 1H), 1.38–1.34 (dd, 6H), 1.30–1.26 (t, 3H). |
| 27 | 5.77 (s, 1H), 4.25–4.23 (q, 2H), 1.39–1.36 (dd, 6H), 1.29–1.26 (t, 3H). |
| 28 | 5.14 (s, 1H), 4.25–4.24 (q, 2H), 1.38–1.34 (dd, 6H), 1.30–1.26 (t, 3H). |
| 29 | 5.74 (s, 1H), 4.24–4.23 (q, 2H), 1.39–1.36 (dd, 6H), 1.2 (t, 3H). |
| 30 | 7.21–7.17 (dd, 2H), 5.11 (s, 1H), 4.24 4.22 (q, 2H), 1.3 (dd, 6H), 1.29–1.26 (t, 3H). |
| 31 | 7.20–7.17 (d, 1H), 7.16–7.14 (d, 1H), 5.11 (s, 1H), 4.25–4.23 (t, 2H), 1.38–1.35 (dd, 6H), 1.29–1.26 (t, 3H). |
| 32 | 7.20–7.17 (d, 1H), 7.16–7.14 (d, 1H), 5.09 (s, 1H), 1.38–1.35 (dd, 6H), 1.17 (t, 3H). |
| 33 | 7.20–7.18 (d, 1H), 7.16–7.19 (d, 1H), 5.10 (s, 1H), 4.24–4.22 (m, 2H), 1.38–1.36 (dd, 6H), 1.19–1.16 (t, 3H). |
| 34 | 5.01 (s, 1H), 4.09 (s, 1H), 1.38–1.34 (dd, 6H), 1.26–1.22 (q, 3H), 0.79–0.62 (m, 2H). |
| 35 | 5.79 (s, 1H), 1.39–1.37 (d, 6H), 1.29–1.25 (t, 3H). |
| 36 | 5.19 (br, s, 2H), 4.76–4.76 (s, 2H), 1.19–1.17 (t, 3H). |
| 37 | 4.99 (s, 1H), 4.76 (s, 2H), 1.27 (t, 3H). |
| 38 | 7.16–7.13 (dd, 2H), 5.20 (s, 1H), 1.21–1.18 (t, 3H), 1.05–1.03 (d, 6H). |
| 39 | 7.21–7.17 (dd, 2H), 4.99 (s, 1h), 1.30–1.26 (t, 3H), 1.05–1.03 (d, 6H). |
| 40 | 7.42 (s, 1H), 7.02 (s, 1H), 5.03–5.02 (br, s, 1H), 4.54–4.51 (m, 1H), 3.71 (s, 3H), 1.39–1.36 (dd, 6H). |
| 41 | 7.45 (s, 1H), 7.04 (s, 1H), 7.04 (s, 1H), 5.20 (s, 1H), 3.77 (s, 3H), 1.39–1.34 (dd, 6H). |
| 42 | 7.44 (s, 1H), 7.41 (s, 1H), 7. 00 (br, 2H), 5.19 (s, 1H), 4.99 (s, 1H), 1.38–1.34 (dd, 6H), 0.89–0.85 (dd, 6H). |
| 43 | 7.42 (s, 1H), 7.40 (s, 1H), 7.01 (br, 2H), 5.19 (s, 1H), 1.37–1.35 (dd, 6H), 1.32–1.29 (t, 3H), 1.20–1.92 (dd, 6H), 1.15–1.09 (t, 3H). |
| 48 | 7.19–7.18 (dd, 2H), 5.11 (s, 1H), 4.50–4.43 (m, 1H), 1.37–1.34 (dd, 6H), 0.91–0.87 (t, 3H). |
| 49 | 4.99 (s, 1H), 1.38–1.35 (dd, 6H), 0.86–0.84 (t, 3H). |
| 50 | 5.10 (s, 1H), 1.37–1.353 (dd, 6H), 0.89–0.88 (dd, 6H). |
| 51 | 7.19–7.17 (d, 1H), 7.15–7.12 (d, 1H), 4.99 (s, 1H), 1.41–1.35 (m, 9H), 0.84–0.82 (d, 6H). |
| 52 | 7.16–7.14 (dd, 2H), 5.79 (s, 1H), 1.39–1.36 (m, 8H), 0.92–0.88 (t, 3H). |
| 54 | 7.21–7.19 (d, 1H), 7.18–7.16 (d, 1H), 5.07 (s, 1H), 1.37 (dd, 6H), 1.26–1.21 (dd, 6H). |
| 56 | 7.21–7.19 (d, 1H), 7.18–7.17 (d, 1H), 5.12 (s, 1H), 3.78 1.38–1.35 (dd, 6H). |
| 58 | 5.10 (s, 1H), 1.37–1.35 (dd, 6H), 0.89–0.86 (dd, 6H). |
| 59 | 4.99 (s, 1H), 1.41–1.35 (m, 9H), 0.84–0.82 (d, 6H). |
| 62 | 5.22 (s, 1H), 5.21 (s, 2H), 4.39–4.30 (q, 2H), 1.33–1.29 |
| 63 | 5.21 (s, 1H), 5.20 (s, 2H), 4.39–4.25 (m, 2H), 1.33–1.29 |
| 64 | 5.12 (s, 1H), 4.55–4.41 (m, 1H), 4.14–4.12 (m, 3H), 1.38–1.34 (dd, 6H), 0.96–0.87 (t, 3H). |

TABLE J-continued

Index

| Cmpd No. | $^1$H NMR Data[1] |
|---|---|
| 65 | 5.79 (s, 1H), 4.17–4.16 (t, 2H), 1.39–1.36 (dd, 6H), 0.92–0.88 (t, 3H). |
| 66 | 5.11 (s, 1H), 1.38–1.34 (dd, 6H), 0.88–0.85 (dd, 6H). |
| 67 | 5.82 (s, 1H), 1.39–1.36 (dd, 6H), 0.91–0.89 (d, 6H). |
| 68 | 5.15 (s, 1h), 3.95–3.94 (q, 2H), 1.38–1.34 (dd, 6H), 0.88–0.86 (d, 6H). |
| 69 | 5.07 (s, 1h), 5.034.99 (q, 1H), 4.504.43 (q, 1H), 1.38–1.34 (dd, 6H), 1.25–1.24 (d, 3H), 1.19–1.17 (d, 3H). |
| 72 | 4.99 (s, 1H), 1.38–1.36 (t, 6H), 0.87–0.86 (t, 6H). |
| 73 | 5.15 (s, 1H), 3.77 (s, 3H), 1.38–1.35 (dd, 6H). |
| 74 | 5.07 (s, 1H), 4.21 (s, 1H), 1.39–1.36 (dd, 6H), 0.89–0.87 (d, 6h). |
| 75 | 5.18–5.16 (m, 3H), 4.624.61 (br, s, 2H), 2.51 (s, 1H). |
| 76 | 5.26–5.19 (m, 1H), 5.05 (s, 1H), 4.61 (s, 2H), 2.54 (s, 2H). |
| 77 | 5.12 (s, 1h), 4.75 (s, 2H), 3.78 (s, 3H), 2.58 (s, 1H). |
| 81 | 4.99 (s, 1H), 4.75 (s, 2H), 0.84–0.82 (dd, 6H). |
| 86 | 5.04–4.99 (m, 2h), 4.75 (s, 2H), 2.58 (s, 2H), 1.16–1.14 (dd, 6H). |
| 89 | 7.40–7.38 (d, 1H), 7.25–7.22 (d, 1H), 5.05 (s, 1H), 4.78–4.74 (m, 4H), 2.6 (s, 1H), 2.52 (s, 1H). |
| 90 | 5.04 (s, 1H), 4.77–4.76 (m, 4H), 2.60 (s, 1H), 2.52 (s, 1H). |
| 94 | 5.19 (s, 1H), 4.90 (q, 1H), 2.53 (s, 1H), 1.71–1.69 (d, 3H), 1.17–1.13 (t, 3H). |
| 95 | 5.19 (s, 1H), 4.55–4.44 (m, 1H), 4.25–4.15 (m, 2HO, 1.39–1.36 (dd, 6H), 1.20–1.16 (t, 3H). |
| 103 | (300 MHz): 5.12 (s, 1H), 4.60–4.52 (m, 1H), 1.39–1.36 (m, 7H), 1.24–1.20 (t, 3H). |
| 122 | 7.18–7.17 (d, 1H), 6.82–6.81 (d, 1H), 5.05 (s, 1H), 4.60 (s, 2H), 1.28–1.25 (m, 6H). |

[1]Unless indicated otherwise, spectra were obtained in CDCl$_3$ at 400 MHz. br = broad, s = singlet, d = doublet, dd = doublet of doublets, t = triplet, q = quartet, m = multiplet.

EXAMPLE 9

Preparation of (S)-2-amino-3-methylbutanamide hydrochloride

Anhydrous ammonia was bubbled through 150 mL of methylene chloride cooled to 0° C. (ice-bath) until the solution was saturated. To this mixture cooled to 5° C. and under N$_2$ was added dropwise trimethylaluminum (136.2 mL of a 2M solution in hexane, 272.4 mmol) available from Aldrich Chemical Co., (Milwaukee, Wis.). The resultant cloudly solution was allowed to warm to room temperature and stirred for 22 h. L-Valine (10.6 g, 90.79 mmol) was added portionwise and stirred for 18 h at room temperature. To this mixture, cooled to 0° C. (ice-water bath), was then added dropwise 190 mL of 6 N HCl until the pH was 2. The resultant mixture allowed to warm and stirred for 2 hours and then made basic (pH=11–12) with 50% aqueous NaOH. To the basic solution was added 100 mL of methylene chloride and 100 mL of H$_2$O. The organic layer was separated, dried over magnesium sulfate and evaporated under reduced pressure to dryness. The resultant residue was dissolved in 100 mL of methylene chloride and acidified with HCl gas. The solid that formed was filtered and dried under reduced pressure to give 6.8 g (49%) of the title compound, mp 258°–260° C. IR (Nujol, cm$^{-1}$), C=O (1686), N—H (3387, 3241). $^1$H NMR and $^{13}$C NMR (CDCl$_3$) consistent with title product. Analysis calculated for C$_5$H$_{13}$ClN$_2$O: C, 39.35; H, 8.59; N, 18.35; Cl, 23.23; Found: C, 39.82; H, 8.52; N, 18.40; Cl, 23.13. MS: m/e 117 (M$^+$-Cl). To 302.1 mg(1.98 mmol) of the title product in 25 mL of tetrahydrofuran under N$_2$ at 0° C. was added dropwise (R)-(–)-α-methoxy-α-(trifluoromethyl)phenylacetyl chloride (500.0 mg, 1.98 mmol, available from Aldrich Chemical Co., Milwaukee, Wis.). After stirring the mixture for an additional 15 min, 50 mL of water and 50 mL of ethyl acetate was added. The ethyl acetate layer was separated, dried over magnesium sulfate and evaporated under reduced pressure to a dry residue. The residue was chromatographed on a silica gel column, eluting with 50% ethyl acetate in hexane. The desired fractions were combined and evaporated under reduced pressure to yield 210 mg (68%) of (R)-(–)-α-methoxy-α-(trifluoromethyl)-phenylacetyl-(S)-2-amino-3-methylbutanamide as a white solid, mp 52°–54° C. $^1$H NMR (300 MHz, CDCl$_3$) δ7.56–7.53 (br,2H), 7.43–7.40 (m,3H), 7.32–7.30 (d,1H), 6.27–6.25 (br,1H), 5.60–5.50 (br,1H), 4.46–4.42 (m,1H), 4.48 (s,3H, OCH$_3$), 2.16–2.12 (m,1H), 0.95–0.93 (d,3H), 0.87–0.85 (d,3H); $^{19}$F NMR (CDCl$_3$) δ–69.41 (singlet). An authentic sample of (S)-2-amino-3-methylbutanamide hydrochloride purchased from Schweizerhall Chem. Co., South Plainfield, N.J. was derivatized in exactly the same manner as above. The mp, $^1$H NMR and $^{19}$F NMR spectra were identical to the derivatized product of the present example indicating that no detectable racemization occurred in the preparation of the title product.

EXAMPLE 10

Preparation of S-2-amino-4-methyl-N-[2-(4-pyridinyl)ethyl]pentanamide

To a stirring solution of 4-(2-aminoethyl) pyridine (15.2 g, 124.17 mmol), in anhydrous methylene chloride (100 mL) under N$_2$ at 0° C. (ice-water bath), was added dropwise, trimethylaluminum (186.26 mL of a 2M solution in hexane, 372.51 mmol). The resultant mixture was stirred under nitrogen at room temperature for 24 hours. L-leucine (16.29 g, 124.17 mmol, Sigma Chemical Co., St. Louis, Mo.) was then added portion wise through a solid addition funnel and the reaction mixture was allowed to stir at room temperature for 72 h. The reaction mixture was cooled to 0° C., treated with 6N hydrochloric acid until the pH of the mixture was 3 to 4, followed by the addition of 200 mL of water. After stirring for 0.5 h, the aqueous layer was separated and made basic (pH=9) with 50% aqueous NaOH. To this aqueous solution was added 400 mL of methylene chloride, the organic layer was separated, dried over magnesium sulfate and evaporated to dryness under vacuum. The residue was chromatographed on silica gel eluting with 2% methanol in methylene chloride to obtain 2.2 g (10%) of the title compound as a yellow oil. IR (neat, cm$^{-1}$), C=O (1658.2), N—H (3303.0). $^1$H NMR (400 MHz, CDCl$_3$): δ8.53–8.51 (d,2H), 7.58–7.49 (br,1H), 7.15–7.14 (d,2H), 3.56–3.53 (m,2H), 3.43–3.39 (d,1H), 1.91–1.89 (br,2H), 1.70–1.68 (m,2H), 1.38–1.26 (t,1H), 0.96–0.91 (dd,6H). Analysis calculated for C$_{13}$H$_{21}$N$_3$O·¼H$_2$O: C, 65.51; H, 9.03; N, 17.52; Found: C, 64.99; H, 8.96; N, 17.18.

EXAMPLE 11

Preparation of S-α-amino-N-[3-(dimethylamino)propyl]benzenpropanamide

To a stirring solution of 3-dimethylaminopropyl amine (10.0 g, 97.86 mmol), in anhydrous methylene chloride (100 mL) under N$_2$ at 0° C. (ice-water bath), was added dropwise, trimethylaluminum (146.79 mL of a 2M solution in hexane, 293.58 mmol). The resultant mixture was stirred under N$_2$ at room temperature for 24 hours. L-phenylalanine hydrochloride (22.48 g, 97.86 mmol, Aldrich Chemical Co., Milwaukee, Wis.) was then added portion wise through a solid addition funnel and the reaction mixture allowed to stir at room temperature for 72 h. The reaction mixture was cooled to 0° C., treated with 6N hydrochloric acid until the pH of the mixture was 2, followed by the addition of 200 mL of water. The aqueous layer was separated and made basic (pH=9) with 50% aqueous NaOH. To this aqueous solution was added 400 mL of methylene chloride, the organic layer was separated, dried over magnesium sulfate and evaporated to dryness under reduced pressure. The residue was chromatographed on silica gel eluting with 50% ethyl acetate in hexane. The desired fractions were combined and evaporated under reduced pressure to give 2.0 g (12%) the title compound as a yellow oil. IR (neat, cm$^{-1}$), C=O (1658), N—H (3299.9). $^1$H NMR (400 MHz, CDCl$_3$): δ7.86–7.85 (br,1H), 7.32–7.21 (m,5H), 3.80–3.78 (m,1H), 3.39–3.23 (m,3H), 2.25–2.24 (m,2H), 2.21–2.19 (s,6H), 1.80–1.79 (m,2H).

EXAMPLE 12

Preparation of (±)-2-amino-N-(2,4-dichlorophenyl)-4-hydroxybutanamide

To a stirring solution of 2,4-dichloroaniline (4.27 g, 26.37 mmol), in anhydrous methylene chloride (100 mL) under N$_2$ at 0° C. (ice-water bath), was added dropwise, trimethylaluminum (39.56 mL of a 2M solution in hexane, 79.11 mmol). The resultant mixture was stirred under N$_2$ at room temperature for 24 h. The mixture was cooled and (±)-α-amino-γ-butyrolactone hydrobromide (39.56 mL, 74.11 mmol, Aldrich Chemical Co., Milwaukee, Wis.) was then added portionwise and the reaction mixture then allowed to stir at room temperature for 48 h. The reaction mixture was cooled to 0° C., treated with 6N hydrochloric acid until the pH of the mixture was 2 to 3. The resultant solid was filtered and suspended in 100 mL of water. The suspension was made basic with 50% aqueous NaOH (pH=13) and 300 mL of methylene chloride was added. The organic layer was separated, dried over magnesium sulfate and evaporated under reduced pressure. The residue obtained was chromatographed on silica gel eluting with 50% ethyl acetate in hexane. The desired fractions were combined and evaporated under reduced pressure to give the title compound as a white solid (2.3 g, 36%), mp 89°–91° C. IR (Nujol, cm$^{-1}$), C=O (1658), N—H (3323.9), OH (3265.9). $^1$H NMR (400 MHz, CDCl$_3$) spectrum was consistent with the title product. Analysis calculated for C$_{10}$H$_{12}$Cl$_2$N$_2$O: C, 45.65; H, 4.60; N, 10.68; Cl, 26.90; Found: C, 45.69; H, 4.60; N, 10.53; Cl, 26.70.

EXAMPLE 13

Preparation of methyl N-L-phenylalanyl-L-valine

A solution of trimethylaluminum (136.2 mL of a 2M solution in hexane, 272.4 mmol) was added dropwise to a stirring suspension of L-phenylalanine (15.0 g, 90.79 mmol) in 150 mL of methylene chloride at 0° C. (ice-bath). The resultant clear solution was allowed to warm to room temperature and stirred for 23 h. A solution of the free base of L-valine methyl ester (15.22 g, 90.79 mmol) in 100 mL of methylene chloride was added dropwise and the resultant clear solution was stirred at room temperature for 72 h. The reaction mixture was then cooled to 0° C. and with stirring, 6N HCl was dropwise until the pH was 2. The mixture was stirred for an additional 0.5 h followed by addition of 40 mL of 50% aqueous NaOH until the pH was 13. To this mixture was added 800 mL of methylene chloride and 100 mL of water. The organic layer was separated, dried over magnesium sulfate and evaporated under reduced pressure to provide a residue which was chromatographed on silica gel using 5% methanol in methylene chloride as the eluting solvent. The desired fractions were collected and evaporated under reduced pressure to yield 5.0 g (34%) of the title product as a colorless oil. IR (neat, cm$^{-1}$), C=O (1665.8, 1742.0), N—H (3366.6). $^1$H NMR and $^{13}$C NMR (CDCl$_3$) spectra were both consistent with the title product. Analysis calculated for C$_{15}$H$_{22}$ClN$_2$O$_e$·¼H$_2$O: C, 56.41; H, 7.42; N, 8.77; Cl, 11.10; Found: C, 56.34; H, 7.65; N, 8.61; Cl, 10.62.

EXAMPLE 14

Preparation of ethyl N-L-phenylalanine-L-alanine

Using the procedure of Example 13, employing 10.0 g of L-phenylalanine (60.53 mmol) and 90.79 mL of 2.0M trimethylaluminum in hexane (181.6 mmol) and 9.29 g of the free base of L-alanine ethyl ester (60.53 mmol), and a similar isolation procedure provided 2.5 g (25%) of the title compound as a yellow oil. IR (neat, cm$^{-1}$), C=O (1665.4, 1738.5), N—H (3366.2). $^1$H NMR and $^{13}$C NMR (CDCl$_3$) spectra were both consistent with the title product.

EXAMPLE 15

Preparation of S-2-amino-N-(4-chloro-2-fluorophenyl)-3-methylbutanamide

To a mixture of 4-chloro-2-fluoroaniline (5.21 g, 35.83 mmol, Aldrich Chemical; Milwaukee, Wis.) and L-valine methylester hydrochloride (6.01 g, 35.83 mmol, Aldrich Chemical; Milwaukee, Wis.) in methylene chloride (100 mL) under N$_2$ at 0° C. (ice-water bath), was added dropwise trimethylaluminum (35.83 mL of a 2M soln, 71.66 mmol). The resultant mixture was stirred under N$_2$ at room temperature for 2 days. The reaction mixture was cooled to 0° C., treated with 6N hydrochloric acid (150 mL), until the foaming stopped. Methylene chloride (300 mL) and H$_2$O (400 mL) were added. The aqueous layer was separated and basicified with 50% NaOH to pH 10. Methylene chloride (500 mL) was added and the organic layer was separated, dried over magnesium sulfate, and evaporated under reduced pressure to dryness. The dried residue was chromatographed on silica gel using 30% ethyl acetate in hexane as the eluting solvent. The desired fractions were collected and evaporated under reduced pressure to yield 4.76 g (63%) of title compound as a white solid, mp 77°–79° C. IR (Nujol, cm$^{-1}$), C=O (1678), N—H (3379,3254). $^1$H NMR (400 MHz, CDCl$_3$): δ9.98 (br,1H), 8.40–8.38 (t,1H), 7.13–7.11 (m,2H), 3.41(br,1H), 2.48–2.40 (m, 1H), 1.48 (br,2H), 1.06–1.04 (d,3H), 0.88–0.86 (d,3H).

EXAMPLE 16

Preparation of R-2-amino-N-(4-chloro-2-fluorophenyl)-4-methylpentanamide

A solution of trimethylaluminum (35.8 mL of a 2M solution in hexane, 71.66 mmol) was added dropwise to a stirred suspension of D-leucine (4.70 g, 35.83 mmol, Aldrich Chemical; Milwaukee, Wis.) in 100 mL of methylene chloride under nitrogen, at 0° C. (ice-water bath). The resulting clear solution was stirred at room temperature overnight. To the solution was added 4-chloro-2-fluoroaniline (5.21 g, 35.83 mmol) portionwise via solid addition funnel and the mixture was stirred at room temperature for 2 days. To the reaction mixture 6N HCl (200 mL) was added until foaming stopped. Methylene chloride(400 mL) and water (200 mL) were added. The aqueous layer was separated and basicified with 50% NaOH to pH 10. Methylene chloride (400 mL) was added. The organic layer was separated, dried over magnesium sulfate, and evaporated to dryness under reduced pressure. The dried residue was chromatographed on silica gel using 30% ethyl acetate in hexane as eluting solvent. The desired fractions were collected and evaporated under reduced pressure to yield (3.61 g, 48%) of the title compound as a white solid, mp 75°–77° C. IR (Nujol, $cm^{-1}$), N—H (3382, 3251), C=O, (1680). $^1$H NMR (400 MHz, $CDCl_3$): δ9.99 (br,1H), 8.40–8.36 (t,1H), 7.13–7.10 (m,2H), 3.58–3.92 (m,1H ), 1.85–1.73 (m,2H), 1.56 (br,2H), 1.48–1.44 (t,1H), 1.01–0.97 (m,6H).

EXAMPLE 17

Preparation of R-2-amino-N-(4-chloro-2-fluorophenyl)-4-methylpentanamide

The title compound of Example 16 was also prepared in the following manner. To a mixture of 4-chloro-2-fluoroaniline(5.21 g, 35.83 mmol) and D-leucine (4.10 g, 35.83 mmol) in methylene chloride (100 mL), was added trimethylaluminum (35.8 mL of a 2M solution in hexane, 71.66 mmol) dropwise at 0° C. under nitrogen. The resultant brown solution was stirred at room temperature for 2 days. A similar workup as in Example 16 yielded the title compound (4.04 g, 55%) as a whim solid, mp 75°–77° C. Spectral data matched that of the compound prepared in Example 16.

By the general procedures described herein, or obvious modifications thereof, the compounds of Index Tables K–P can be prepared. In the Tables, the α-amino amide product, when chiral, is indicated by a wedge or hash bond at the chiral carbon, if not so indicated, the product is racemic. In Index Tables K–N, the designations R, R', R" and R"' are used to indicate the substituents on the aromatic ring as previously defined for $R^{43}$.

INDEX TABLE K

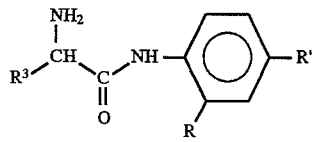

| Compound | R | R' | R" | R"' | mp (°C.) |
|---|---|---|---|---|---|
| 125 | Cl | H | F | H | 118–119 |
| 126 | F | H | F | H | 87–89 |
| 127 | Br | H | F | H | 115–117 |
| 128 | F | H | Cl | $OCH(CH_3)_2$ | 96–98 |
| 129 | F | H | Cl | $OCH_2C\equiv CH$ | 120–122 |
| 130 | Cl | H | Cl | H | 122–123 |
| 131 | Br | H | $CH_3$ | H | 65–67 |
| 132 | H | Cl | $OCH_3$ | H | 94–96 |

INDEX TABLE L

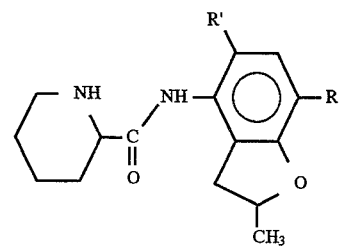

| Compound | R | R' | mp (°C.) |
|---|---|---|---|
| 133 | Cl | Cl | gum |
| 134 | Cl | F | 114–116 |

INDEX TABLE M

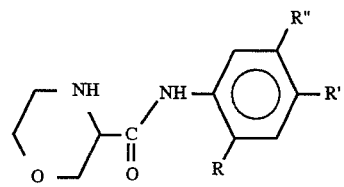

| Compound | R | R' | R" | mp (°C.) |
|---|---|---|---|---|
| 135 | F | Cl | $OCH_2C\equiv CH$ | 164–166 |
| 136 | F | Cl | $OCH_2CH(CH_3)_2$ | 119–121 |
| 137 | F | Cl | $OCH(CH_3)_2$ | 99–101 |

INDEX TABLE N

| Compound | R' | R | $R^3$ | mp (°C.) |
|---|---|---|---|---|
| 138 | F | H | $CH(CH_3)_2$ | oil |
| 139 | $CH_3$ | Br | $CH(CH_3)_2$ | 230–232 |
| 140 | I | H | $CH(CH_3)_2$ | 103–105 |
| 141 | CN | H | $CH(CH_3)_2$ | 66–68 |
| 142 | $CH_3$ | Br | $CH_3$ | 110–112 |
| 143 | Cl | F | $CH_2CH_2SO_2CH_3$ | 193–194 |
| 144 | Cl | F | $CH_2SH$ | 133–135 |

INDEX TABLE O
| Compound | α-amino-amide | mp (°C.) |
|---|---|---|
| 145 | 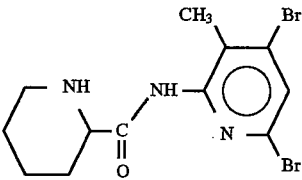 | 105–107 |
| 146 | 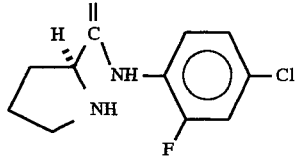 | 96–98 |
| 147 | 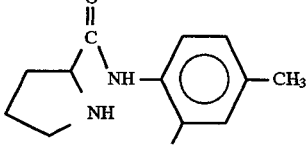 | 75–77 |
| 148 | 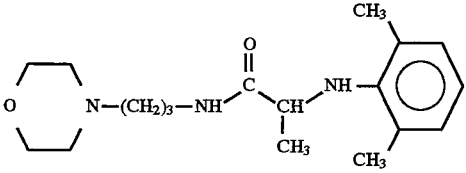 | oil |
| 149 | 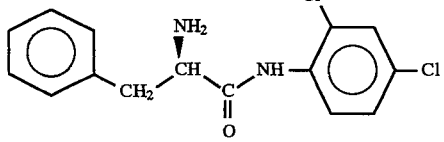 | oil |
| 150 | 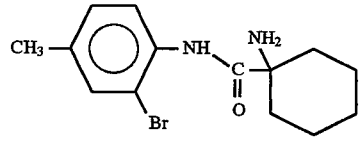 | 110–112 |
| 151 | 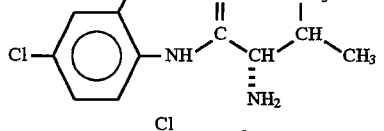 | 82–83 |
| 152 | 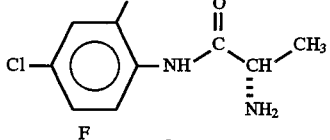 | 63–65 |
| 153 | 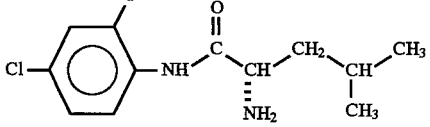 | 74–75 |
| 154 | 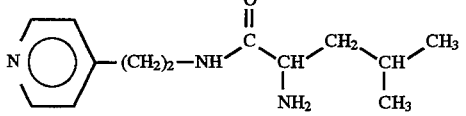 | oil |

INDEX TABLE O-continued

| Compound | α-amino-amide | mp (°C.) |
|---|---|---|
| 155 | Structure: 2,6-dichlorophenyl-NH-C(=O)-CH(NH-)-pyrrolidine with OH | 109–111 |
| 156 | Structure: 4-(propargyloxy)-2-chlorophenyl-NH-C(=O)-CH(NH-)-pyrrolidine with OH (CH$_2$C≡CH) | 139–141 |
| 157 | Structure: 2,6-dichlorophenyl-NH-C(=O)-CH(NH$_2$)-CH$_2$CH$_2$SCH$_3$ | 196–198 |
| 158 | Structure: (CH$_3$)$_2$CHCH$_2$-NH-C(=O)-CH(NH$_2$)-CH(CH$_3$)$_2$ | 140–142 |

TEST A

Seeds of barnyardgrass (*Echinochloa crus-galli*), cheatgrass (*Bromus secalinus*), cocklebur (*Xanthium pensylvanicum*), crabgrass (*Digitaria spp.*), giant foxtail (*Setaria faberi*), morningglory (*Ipomoea spp.*), sorghum (*Sorghum bicolor*), velvetleaf (*Abutilon theophrasti*), and wild oat (*Avena fatua*) were planted into a sandy loam soil and treated preemergence with test chemicals dissolved in a non-phytotoxic solvent. At the same time, these crop and weed species were also treated postemergence with test chemicals. Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table A, are based on a 0 to 10 scale where 0 is no effect and 10 is complete control. A dash (–) response means no test results.

TABLE A

| | COMPOUND 1 | COMPOUND 2 | | COMPOUND 1 | COMPOUND 2 |
|---|---|---|---|---|---|
| Rate 2000 g/ha | | | Rate 2000 g/ha | | |
| POST-EMERGENCE | | | PREEMERGENCE | | |
| | | | Barnyardgrass | 2 | 1 |
| Barnyardgrass | 1 | 2 | Cheatgrass | 2 | 2 |
| Cheatgrass | 1 | 1 | Cocklebur | 0 | 0 |
| Cocklebur | 3 | 3 | Crabgrass | 2 | 1 |
| Crabgrass | 1 | 3 | Giant foxtail | 9 | 7 |
| Gaint foxtail | 1 | 2 | Morningglory | 0 | 0 |

TABLE A-continued

| Morningglory | 2 | 7 | Sorghum | 1 | 1 |
|---|---|---|---|---|---|
| Sorghum | 1 | 2 | Velvetleaf | 10 | 6 |
| Velvetleaf | 4 | 4 | Wild oats | 1 | 0 |
| Wild oats | 1 | 1 | | | |

| Rate 1000 g/ha | COMPOUND 14 | Rate 1000 g/ha | COMPOUND 14 |
|---|---|---|---|
| POST-EMERGENCE | | PREEMERGENCE | |
| | | Barnyardgrass | 0 |
| Barnyardgrass | 1 | Cheatgrass | 0 |
| Cheatgrass | 0 | Cocklebur | 0 |
| Cocklebur | 0 | Crabgrass | 0 |
| Crabgrass | 1 | Giant foxtail | 0 |
| Giant foxtail | 1 | Morningglory | 0 |
| Morningglory | 1 | Sorghum | 0 |
| Sorghum | 1 | Velvetleaf | 0 |
| Velvetleaf | 2 | Wild oats | 0 |
| Wild oats | 0 | | |

TEST B

Seeds of barley (*Hordeum vulgare*), barnyardgrass (*Echinochloa crus-galli*), bedstraw (*Galium aparine*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria spp.*), downy brome (*Bromus tectorum*), giant foxtail (*Setaria faberi*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table B, are based on a scale of 0 to 10 where 0 is no effect and 10 is complete control. A dash (—) response means no test result.

TABLE B

| Rate 2000 g/ha | COMPOUND | | | | | | | | | | | | | | | | |
|---|---|---|---|---|---|---|---|---|---|---|---|---|---|---|---|---|---|
| | 1 | 3 | 4 | 5 | 6 | 10 | 11 | 12 | 13 | 17 | 18 | 19 | 20 | 21 | 22 | 23 | 40 | 41 |
| POSTEMERGENCE | | | | | | | | | | | | | | | | | | |
| Barley | 2 | 1 | 1 | 2 | 3 | 2 | 2 | 0 | 0 | 0 | 2 | 2 | 0 | 2 | 9 | 0 | 3 | 2 |
| Barnyardgrass | 1 | 1 | 1 | 1 | 9 | 6 | 1 | 2 | 0 | 0 | 3 | 2 | 2 | 4 | 9 | 0 | 4 | 3 |
| Bedstraw | 3 | 3 | 3 | 3 | 7 | 2 | 1 | 1 | 0 | 0 | 2 | 1 | 2 | 1 | 8 | 2 | 1 | 1 |
| Blackgrass | 1 | 2 | 2 | 2 | 6 | 3 | 1 | 1 | 0 | 0 | 2 | 0 | 2 | 1 | 4 | 0 | 1 | 1 |
| Cheatgrass | 0 | 1 | 1 | 1 | 3 | 1 | 0 | 0 | 0 | 0 | 1 | 0 | 0 | 1 | 5 | 0 | 2 | 3 |
| Chickweed | 4 | 3 | 1 | 1 | — | 2 | 0 | 0 | 0 | 0 | 0 | 0 | 0 | 1 | 4 | 0 | 0 | 0 |
| Cocklebur | 2 | 2 | 1 | 2 | 9 | 3 | 1 | 1 | 0 | 0 | 2 | 1 | 0 | 4 | 9 | 0 | 3 | 3 |
| Corn | 0 | 1 | 0 | 1 | 4 | 2 | 2 | 1 | 0 | 0 | 2 | 2 | 1 | 2 | 6 | 0 | 2 | 2 |
| Cotton | 9 | 3 | 4 | 9 | 9 | 10 | 4 | 6 | 0 | 0 | 8 | 4 | 8 | 9 | 10 | 8 | 9 | 9 |
| Crabgrass | 1 | 1 | 1 | 2 | 5 | 3 | 2 | 1 | 0 | 0 | 3 | 2 | 2 | 3 | 9 | 1 | 3 | 4 |
| Downy brome | — | — | — | — | — | — | — | — | — | — | — | — | — | — | — | — | — | — |
| Giant foxtail | 1 | 1 | 1 | 1 | 7 | 2 | 2 | 0 | 0 | 0 | 3 | — | 2 | 3 | 8 | 0 | 3 | 3 |
| Lambsquarter | 8 | 1 | 1 | — | 10 | 10 | 7 | 2 | — | 0 | 9 | 6 | 8 | 9 | 10 | 4 | 10 | 8 |
| Morningglory | 3 | 4 | 4 | 3 | 9 | 5 | 3 | 1 | 0 | 0 | 2 | 1 | 3 | 4 | 9 | 0 | 7 | 6 |
| Nutsedge | 0 | 10 | 1 | 0 | 2 | 2 | 0 | 0 | 0 | 0 | 0 | 0 | 0 | 0 | 5 | 0 | 2 | 1 |
| Rape | 2 | 1 | 2 | 1 | 8 | 2 | 3 | 1 | 0 | 4 | 2 | 2 | 0 | 2 | 9 | 2 | 2 | 1 |
| Rice | 2 | 1 | 0 | 3 | 6 | 5 | 3 | 1 | 0 | 0 | 1 | 2 | 2 | 3 | 9 | 0 | 3 | 3 |
| Sorghum | 1 | 1 | 0 | 0 | 6 | 2 | 2 | 1 | 0 | 0 | 2 | 4 | 3 | 4 | 8 | 2 | 3 | 3 |
| Soybean | 1 | 2 | 1 | 0 | 8 | 3 | 3 | 2 | 0 | 0 | 2 | 3 | 3 | 4 | 9 | 3 | 5 | 4 |
| Sugar beet | 6 | 2 | 2 | 2 | 10 | 9 | 8 | 1 | 0 | 3 | 6 | 2 | 0 | 5 | 10 | 2 | 8 | 9 |
| Velvetleaf | 5 | 3 | 2 | 4 | 9 | 7 | 1 | 2 | 0 | 0 | 2 | 2 | 2 | 3 | 9 | 0 | 9 | 2 |
| Wheat | 2 | 2 | 2 | 1 | 3 | 2 | 2 | 0 | 0 | 0 | 1 | 1 | 0 | 1 | 8 | 0 | 1 | 1 |
| Wild buckwheat | 5 | 1 | 2 | 5 | 10 | 3 | 1 | 2 | 0 | 0 | 2 | 2 | 2 | 2 | 10 | 2 | 6 | 7 |
| Wild oat | 2 | 1 | 1 | 1 | 4 | 1 | 1 | 0 | 0 | 0 | 1 | 1 | 0 | 2 | 8 | 0 | 2 | 1 |

| Rate 2000 g/ha | COMPOUND | | | | | | | | | | | | | | | | |
|---|---|---|---|---|---|---|---|---|---|---|---|---|---|---|---|---|---|
| | 1 | 3 | 4 | 5 | 6 | 10 | 11 | 12 | 13 | 17 | 18 | 19 | 20 | 21 | 22 | 23 | 40 | 41 |
| PREEMERGENCE | | | | | | | | | | | | | | | | | | |
| Barley | 0 | 0 | 0 | 0 | 0 | 0 | 0 | 0 | 0 | 0 | 0 | 0 | 0 | 0 | 3 | 0 | 0 | 0 |
| Barnyardgrass | 0 | 0 | 0 | 0 | 9 | 5 | 4 | 0 | 0 | 0 | 0 | 0 | 0 | 2 | 9 | 0 | 4 | 0 |
| Bedstraw | 3 | 0 | 0 | 0 | 9 | 4 | 0 | 0 | 0 | — | 0 | 0 | 0 | 2 | 10 | 0 | 2 | 0 |
| Blackgrass | 1 | 3 | 0 | 0 | 8 | 1 | 0 | 0 | 0 | 0 | 0 | 0 | 4 | 2 | 7 | 1 | 1 | 0 |
| Cheatgrass | 0 | 0 | 0 | 0 | 7 | 2 | 0 | 2 | 0 | 0 | 0 | 0 | 5 | 6 | 3 | 0 | 3 | 3 |
| Chickweed | 1 | 0 | 0 | 4 | 0 | 0 | 6 | 0 | 0 | 0 | 0 | 0 | 0 | 0 | 7 | 0 | 1 | 0 |
| Cocklebur | 0 | 0 | 0 | 0 | 1 | 0 | 0 | 0 | 0 | 0 | 0 | 0 | 0 | 0 | 4 | 0 | 0 | 0 |
| Corn | 0 | 0 | 0 | 0 | 1 | 2 | 0 | 0 | 0 | 0 | 0 | 0 | 0 | 0 | 6 | 0 | 0 | 0 |
| Cotton | 1 | 0 | 0 | 0 | 0 | 0 | 0 | 0 | 0 | 0 | 0 | 0 | 0 | 0 | 1 | 0 | 3 | 0 |
| Crabgrass | 2 | 0 | 0 | 0 | 7 | 7 | 2 | 0 | 0 | 0 | 0 | 0 | 2 | 4 | 10 | 1 | 8 | 2 |
| Downy brome | — | — | — | — | — | — | — | — | — | — | — | — | — | — | — | — | — | — |
| Giant foxtail | 3 | 0 | 0 | 0 | 9 | 7 | 9 | 0 | 0 | 0 | 0 | 0 | 0 | — | 9 | 0 | 7 | 4 |
| Lambsquarter | 10 | 0 | 0 | 3 | 10 | 10 | 10 | 0 | 0 | 0 | 0 | 0 | 10 | 10 | 10 | 0 | 10 | 10 |
| Morningglory | 0 | 0 | 0 | 0 | 2 | 0 | 3 | 0 | 0 | 0 | 0 | 0 | 0 | 0 | 6 | 0 | 3 | 0 |
| Nutsedge | 0 | 4 | 0 | — | 0 | 0 | 0 | 0 | 0 | 0 | 0 | 0 | 0 | 0 | 10 | — | 0 | 0 |
| Rape | 4 | 0 | 0 | 0 | 10 | 1 | 0 | 0 | 0 | 0 | 0 | 0 | 0 | 0 | 10 | 0 | 2 | 0 |
| Rice | 0 | 0 | 0 | 0 | 5 | 3 | 4 | 0 | 0 | 0 | 0 | 0 | 0 | 1 | 7 | 0 | 3 | 2 |
| Sorghum | 2 | 0 | 0 | 0 | 3 | 0 | 0 | 0 | 0 | 0 | 0 | 0 | 0 | 0 | 3 | 0 | 3 | 0 |
| Soybean | 0 | 0 | 0 | 0 | 4 | 0 | 0 | 0 | 0 | 0 | 0 | 0 | 0 | 0 | 6 | 0 | 4 | 0 |
| Sugar beet | 4 | 0 | 0 | 0 | 7 | 8 | 2 | 0 | 0 | 0 | 0 | 0 | 2 | 9 | 10 | 0 | 3 | 3 |
| Velvetleaf | 3 | 0 | 0 | 1 | 10 | 6 | 0 | 0 | 0 | 0 | 0 | 0 | 0 | 2 | 10 | 0 | 6 | 2 |
| Wheat | 0 | 0 | 0 | 0 | 1 | 2 | 2 | 0 | 0 | 0 | 0 | 0 | 0 | 0 | 7 | 0 | 0 | 0 |
| Wild buckwheat | 8 | 0 | 1 | 2 | 10 | 3 | 9 | 0 | 0 | 0 | 0 | 0 | 0 | 0 | 7 | 0 | 5 | 0 |
| Wild oat | 0 | 0 | 0 | 0 | 4 | 4 | 0 | 0 | 0 | 0 | 0 | 0 | 0 | 0 | 7 | 0 | 0 | 0 |

| Rate 1000 g/ha | COMPOUND | | | | | | | | | | | | | | | | |
|---|---|---|---|---|---|---|---|---|---|---|---|---|---|---|---|---|---|
| | 7 | 15 | 16 | 26 | 27 | 28 | 29 | 30 | 31 | 32 | 33 | 34 | 35 | 36 | 38 | 39 | 42 |
| POSTEMERGENCE | | | | | | | | | | | | | | | | | |
| Barley | 4 | 0 | 2 | 1 | 2 | 4 | 3 | 5 | 6 | 7 | 3 | 2 | 5 | 9 | 5 | 7 | 2 |

TABLE B-continued

| | | | | | | | | | | | | | | | | | |
|---|---|---|---|---|---|---|---|---|---|---|---|---|---|---|---|---|---|
| Barnyardgrass | 8 | 0 | 3 | 0 | 4 | 9 | 3 | 9 | 9 | 9 | 7 | 1 | 9 | 9 | 3 | 9 | 3 |
| Bedstraw | 5 | 0 | 3 | 1 | 2 | 8 | 5 | 6 | 6 | 9 | 7 | 3 | 8 | 8 | 4 | 7 | 1 |
| Blackgrass | 3 | 0 | 1 | 1 | 2 | 3 | 2 | 5 | 5 | 6 | 5 | 1 | 5 | 6 | 4 | 5 | 1 |
| Cheatgrass | 3 | 0 | 1 | 1 | 2 | 5 | 3 | 3 | 4 | 5 | 3 | 1 | 6 | 5 | 3 | 3 | 2 |
| Chickweed | — | 0 | 2 | 0 | 0 | 3 | 0 | 6 | 6 | 3 | 2 | — | — | 7 | 5 | 6 | 0 |
| Cocklebur | 8 | 0 | 4 | 0 | 1 | 7 | 7 | 7 | 8 | 8 | 5 | 0 | 9 | 7 | 6 | 8 | 3 |
| Corn | 3 | 0 | 3 | 0 | 2 | 4 | 3 | 4 | 6 | 7 | 5 | 0 | 6 | 3 | 4 | 3 | 2 |
| Cotton | 9 | 0 | 8 | 2 | 10 | 10 | 9 | 10 | 10 | 10 | 10 | 0 | 10 | 9 | 9 | 10 | 8 |
| Crabgrass | 3 | 0 | 3 | 2 | 4 | 7 | 3 | 8 | 9 | 8 | 4 | 2 | 8 | 9 | 5 | 4 | 2 |
| Downy brome | — | — | — | — | — | — | — | — | — | — | — | — | — | — | — | — | — |
| Giant foxtail | 5 | 0 | 3 | 0 | 3 | 6 | 2 | 6 | 7 | 9 | 7 | 1 | 8 | 8 | 4 | 6 | 2 |
| Lambsquarter | 9 | 0 | 7 | 3 | 7 | 9 | 9 | 9 | 10 | 10 | 10 | 2 | 10 | 10 | 9 | 10 | 8 |
| Morningglory | 8 | 0 | 6 | 0 | 2 | 7 | 9 | 8 | 8 | 8 | 8 | 1 | 9 | 8 | 8 | 9 | 4 |
| Nutsedge | 0 | 0 | 2 | 4 | 6 | 3 | 3 | 6 | 7 | 5 | 4 | 0 | 3 | 1 | 1 | 1 | 0 |
| Rape | 7 | 0 | 1 | 0 | 2 | 6 | 3 | 6 | 7 | 8 | 6 | 0 | 10 | 8 | 5 | 8 | 2 |
| Rice | 4 | 0 | 3 | 2 | 3 | 6 | 4 | 7 | 9 | 8 | 8 | 2 | 9 | 8 | 3 | 4 | 1 |
| Sorghum | 5 | 0 | 5 | 0 | 4 | 5 | 3 | 5 | 6 | 7 | 6 | 1 | 6 | 8 | 4 | 3 | 2 |
| Soybean | 5 | 0 | 5 | 2 | 4 | 9 | 2 | 7 | 8 | 7 | 5 | 2 | 9 | 9 | 3 | 9 | 2 |
| Sugar beet | 9 | 0 | 7 | 1 | 7 | 10 | 8 | 10 | 9 | 9 | 9 | 0 | 10 | 10 | 9 | 10 | 4 |
| Velvetleaf | 10 | 0 | 6 | 0 | 7 | 10 | 7 | 8 | 10 | 10 | 10 | 1 | 10 | 8 | 10 | 3 | 3 |
| Wheat | 2 | 0 | 2 | 0 | 0 | 3 | 2 | 6 | 7 | 6 | 5 | 0 | 6 | 7 | 5 | 5 | 1 |
| Wild buckwheat | 9 | 0 | 4 | 1 | 2 | 10 | 6 | 8 | 10 | 8 | 8 | 2 | 10 | 10 | 10 | 10 | 3 |
| Wild oat | 3 | 0 | 2 | 1 | 1 | 4 | 1 | 7 | 8 | 6 | 5 | 0 | 7 | 7 | 5 | 5 | 2 |

| | COMPOUND | | | | | | | | | | | | | | | |
|---|---|---|---|---|---|---|---|---|---|---|---|---|---|---|---|---|
| Rate 1000 g/ha | 43 | 44 | 45 | 46 | 47 | 48 | 49 | 50 | 51 | 52 | 53 | 54 | 55 | 56 | 57 | 58 |
| POSTEMERGENCE | | | | | | | | | | | | | | | | |
| Barley | 2 | 2 | 3 | 2 | 4 | 3 | 4 | 3 | 4 | 4 | 4 | 3 | 3 | 2 | 4 | 3 |
| Barnyardgrass | 3 | 3 | 4 | 6 | 8 | 8 | 9 | 8 | 8 | 8 | 9 | 9 | 8 | 8 | 8 | 9 |
| Bedstraw | 1 | 6 | 3 | 3 | 9 | 8 | 9 | 7 | 7 | 8 | 7 | 6 | 8 | 6 | 7 | 6 |
| Blackgrass | 1 | 2 | 3 | 2 | 4 | 2 | 3 | 3 | 5 | 4 | 6 | 3 | 4 | 3 | 4 | 3 |
| Cheatgrass | 3 | 1 | 2 | 1 | 6 | 2 | 7 | 2 | 9 | 1 | — | 3 | — | — | 3 | — |
| Chickweed | 1 | 3 | 3 | 2 | 3 | 3 | 3 | 3 | 3 | 3 | 6 | 5 | 3 | 4 | 3 | 3 |
| Cocklebur | 3 | 6 | 5 | 5 | 7 | 8 | 7 | 7 | 9 | 8 | 4 | 8 | 6 | 6 | 5 | 6 |
| Corn | 2 | 2 | 3 | 2 | 5 | 4 | 6 | 4 | 6 | 4 | 6 | 5 | 5 | 4 | 6 | 5 |
| Cotton | 9 | 9 | 8 | 10 | 8 | 9 | 10 | 10 | 9 | 9 | 10 | 10 | 10 | 10 | 9 | 10 |
| Crabgrass | 3 | 4 | 4 | 4 | 5 | 7 | 5 | 7 | 6 | 7 | 8 | 7 | 7 | 7 | 7 | 7 |
| Downy brome | — | — | — | — | — | — | — | — | — | — | — | — | — | — | — | — |
| Giant foxtail | 3 | 4 | 3 | 6 | 8 | 7 | 8 | 7 | 8 | 8 | 9 | 8 | 8 | 8 | 8 | 7 |
| Lambsquarter | 8 | 9 | 9 | 9 | 10 | 10 | 10 | 9 | 10 | 10 | 10 | 10 | 9 | 10 | 10 | 10 |
| Morningglory | 5 | 8 | 8 | 8 | 8 | 8 | 9 | 6 | 9 | 9 | 9 | 9 | 9 | 9 | 9 | 8 |
| Nutsedge | 0 | 2 | 1 | 3 | 4 | 3 | 4 | 4 | 2 | 4 | 5 | 6 | 2 | 2 | 3 | 2 |
| Rape | 3 | 4 | 6 | 6 | 8 | 8 | 7 | 6 | 6 | 8 | 6 | 6 | 7 | 6 | 7 | 4 |
| Rice | 2 | 6 | 5 | 7 | 5 | 6 | 8 | 7 | 8 | 7 | 8 | 8 | 7 | 7 | 6 | 6 |
| Sorghum | 2 | 4 | 3 | 3 | 7 | 5 | 6 | 7 | 6 | 5 | 6 | 6 | 5 | 4 | 6 | 5 |
| Soybean | 3 | 3 | 3 | 3 | 5 | 4 | 8 | 7 | 6 | 5 | 7 | 7 | 7 | 6 | 5 | 7 |
| Sugar beet | 6 | 9 | 7 | 8 | 10 | 10 | 10 | 10 | 9 | 9 | 10 | 10 | 7 | 9 | 10 | 9 |
| Velvetleaf | 5 | 6 | 5 | 7 | 10 | 6 | 8 | 10 | 10 | 10 | 8 | 10 | 9 | 7 | 10 | 10 |
| Wheat | 1 | 2 | 2 | 3 | 3 | 2 | 5 | 3 | 3 | 3 | 5 | 4 | 4 | 3 | 3 | 4 |
| Wild buckwheat | 2 | 10 | 8 | 8 | 10 | 10 | 10 | 10 | 5 | 10 | 10 | 10 | 10 | 10 | 10 | 10 |
| Wild oat | 1 | 2 | 3 | 3 | 5 | 3 | 6 | 1 | 4 | 5 | 4 | 5 | 3 | 5 | 5 | 5 |

| | COMPOUND | | | | | | | | | | | | | | | |
|---|---|---|---|---|---|---|---|---|---|---|---|---|---|---|---|---|
| Rate 1000 g/ha | 59 | 60 | 61 | 63 | 64 | 65 | 66 | 70 | 71 | 72 | 73 | 74 | 75 | 76 | 77 | 78 |
| POSTEMERGENCE | | | | | | | | | | | | | | | | |
| Barley | 5 | 1 | 1 | 2 | 2 | 0 | 3 | 2 | 9 | 2 | 2 | 0 | 7 | 8 | 6 | 7 |
| Barnyardgrass | 9 | 2 | 2 | 2 | 3 | 2 | 1 | 1 | 10 | 7 | 1 | 0 | 9 | 9 | 9 | 9 |
| Bedstraw | 8 | 2 | 2 | 3 | 4 | 0 | 3 | 5 | 10 | 3 | 4 | 0 | 7 | 6 | 6 | 7 |
| Blackgrass | 6 | 1 | 1 | 1 | 1 | 0 | 1 | 3 | 6 | 3 | 1 | 0 | 4 | 7 | 6 | 7 |
| Cheatgrass | — | 1 | 1 | 0 | 0 | 0 | — | 2 | 9 | 3 | 1 | 0 | 7 | 9 | 8 | 8 |
| Chickweed | 3 | 2 | 1 | 0 | 1 | 0 | 0 | 2 | 8 | 2 | 2 | 0 | 6 | 10 | 6 | 6 |
| Cocklebur | 9 | 2 | 1 | 1 | 3 | 0 | 3 | 2 | 8 | 2 | 2 | 0 | 7 | 9 | 6 | 7 |
| Corn | 6 | 0 | 0 | 1 | 2 | 0 | 0 | 3 | 8 | 2 | 1 | 0 | 7 | 8 | 5 | 6 |
| Cotton | 9 | 2 | 6 | 4 | 1 | 1 | 0 | 10 | 10 | 8 | 9 | 1 | 10 | 10 | 10 | 10 |
| Crabgrass | 8 | 1 | 2 | — | 2 | 0 | 2 | 2 | 9 | 2 | 2 | 0 | 9 | 9 | 8 | 8 |
| Downy brome | — | — | — | — | — | — | — | — | — | — | — | — | — | — | — | — |
| Giant foxtail | 8 | 3 | 2 | 2 | 2 | 0 | 1 | 2 | 9 | 4 | 1 | 0 | 8 | 9 | 8 | 9 |
| Lambsquarter | 9 | 8 | — | — | — | — | — | 10 | 10 | — | — | 0 | — | — | — | — |
| Morningglory | 10 | 6 | 3 | 2 | 7 | 1 | 4 | 4 | 9 | 6 | 2 | 0 | 8 | 8 | 6 | 7 |
| Nutsedge | 5 | 0 | 2 | 0 | 0 | 0 | 1 | — | 7 | 1 | 0 | 0 | 5 | 4 | 3 | 4 |
| Rape | 7 | 4 | 1 | 4 | 5 | 0 | 1 | 4 | 9 | 4 | 6 | 0 | 9 | 9 | 8 | 9 |
| Rice | 8 | 2 | 3 | 3 | 3 | 1 | 2 | 3 | 9 | 4 | 2 | 0 | 8 | 9 | 9 | 9 |
| Sorghum | 6 | 3 | 2 | 2 | 3 | 2 | 4 | 2 | 9 | 3 | 2 | 0 | 5 | 7 | 6 | 9 |

TABLE B-continued

| | | | | | | | | | | | | | | | | |
|---|---|---|---|---|---|---|---|---|---|---|---|---|---|---|---|---|
| Soybean | 7 | 2 | 2 | 3 | 4 | 2 | 3 | 2 | 8 | 3 | 2 | 0 | 3 | 6 | 7 | 5 |
| Sugar beet | 9 | 8 | 7 | 6 | 8 | 0 | 6 | 6 | 10 | 4 | 8 | 0 | 10 | 10 | 9 | 10 |
| Velvetleaf | 10 | 0 | 2 | 2 | 3 | 0 | 1 | 1 | 10 | 2 | 1 | 0 | 8 | 7 | 7 | 10 |
| Wheat | 4 | 2 | 2 | 1 | 1 | 0 | 0 | 2 | 9 | 1 | 2 | 0 | 6 | 7 | 6 | 6 |
| Wild buckwheat | 10 | 4 | 2 | 4 | 2 | 0 | 2 | 4 | 10 | 4 | 2 | 0 | 10 | 10 | 10 | 10 |
| Wild oat | 4 | 1 | 1 | 2 | 1 | 0 | 1 | 2 | 9 | 2 | 0 | 0 | 7 | 8 | 7 | 9 |

| | COMPOUND | | | | | | | | | | | | | | | |
|---|---|---|---|---|---|---|---|---|---|---|---|---|---|---|---|---|
| Rate 1000 g/ha | 79 | 80 | 81 | 82 | 83 | 84 | 85 | 86 | 87 | 88 | 90 | 91 | 92 | 97 | 98 | 100 |
| POSTEMERGENCE | | | | | | | | | | | | | | | | |
| Barley | 4 | 3 | 5 | 7 | 7 | 7 | 3 | 7 | 3 | 3 | 5 | 3 | 10 | 5 | 5 | 3 |
| Barnyardgrass | 8 | 9 | 9 | 9 | 9 | 9 | 4 | 9 | 1 | 3 | 3 | 5 | 10 | 9 | 5 | 4 |
| Bedstraw | 7 | 3 | 4 | 7 | 5 | 5 | 3 | 8 | 3 | 5 | 3 | 7 | 10 | 9 | 10 | 9 |
| Blackgrass | 3 | 4 | 6 | 6 | 4 | 5 | 3 | 7 | 2 | 2 | 3 | 4 | 9 | 6 | 4 | 5 |
| Cheatgrass | 3 | 3 | 5 | 8 | 3 | 7 | 3 | 8 | 2 | 2 | 2 | 3 | 10 | 4 | 2 | 5 |
| Chickweed | 5 | 4 | 6 | 8 | 5 | 6 | 3 | 8 | 3 | 3 | 4 | 4 | 10 | 6 | 4 | 4 |
| Cocklebur | 6 | 5 | 6 | 8 | 6 | 6 | 2 | 7 | 2 | 5 | 4 | 8 | 9 | 6 | 7 | 4 |
| Corn | 3 | 3 | 6 | 5 | 5 | 8 | 1 | 6 | 1 | 3 | 2 | 3 | 9 | 3 | 3 | 5 |
| Cotton | 9 | 10 | 9 | 10 | 10 | 10 | 7 | 10 | 8 | 9 | 10 | 10 | 10 | 10 | 9 | 10 |
| Crabgrass | 5 | 4 | 8 | 9 | 8 | 8 | 1 | 8 | 2 | 3 | 3 | 7 | 9 | 4 | 6 | 6 |
| Downy brome | — | — | — | — | — | — | — | — | — | — | — | — | — | — | — | — |
| Giant foxtail | 6 | 8 | 8 | 9 | 8 | 9 | 1 | 9 | 4 | 3 | 4 | 7 | 9 | 7 | 8 | 5 |
| Lambsquarter | 10 | 9 | 10 | 10 | 10 | 10 | 8 | 10 | 7 | — | 9 | 9 | 10 | 9 | 10 | 7 |
| Morningglory | 9 | 8 | 10 | 10 | 8 | 9 | 4 | 9 | 6 | 5 | 7 | 9 | 10 | 8 | 10 | 8 |
| Nutsedge | 4 | 2 | 4 | 4 | 3 | 3 | 2 | 5 | 0 | 2 | 2 | 4 | 4 | 3 | — | 5 |
| Rape | 6 | 6 | 7 | 9 | 8 | 6 | 4 | 9 | 3 | 3 | 2 | 2 | 10 | 8 | 7 | 6 |
| Rice | 5 | 7 | 8 | 9 | 7 | 8 | 3 | 9 | 3 | 4 | 7 | 5 | 9 | 9 | 9 | 8 |
| Sorghum | 2 | 3 | 7 | 8 | 6 | 8 | 2 | 8 | 2 | 3 | 3 | 4 | 9 | 3 | 5 | 4 |
| Soybean | 2 | 4 | 3 | 7 | 4 | 3 | 3 | 9 | 2 | 3 | 5 | 9 | 8 | 7 | 8 | 8 |
| Sugar beet | 9 | 8 | 10 | 10 | 10 | 9 | 4 | 9 | 5 | 6 | 10 | 10 | 10 | 10 | 10 | 6 |
| Velvetleaf | 9 | 3 | 10 | 10 | 10 | 10 | 3 | 10 | 2 | 4 | 9 | 10 | 10 | 10 | 5 | 6 |
| Wheat | 6 | 3 | 6 | 7 | 6 | 8 | 3 | 7 | 2 | 2 | 2 | 4 | 8 | 7 | 5 | 2 |
| Wild buckwheat | 10 | 10 | 10 | 10 | 10 | 10 | 5 | 10 | 3 | 8 | 10 | 10 | 10 | 9 | 10 | 9 |
| Wild oat | 8 | 5 | 8 | 8 | 7 | 8 | 3 | 8 | 2 | 2 | 1 | 2 | 10 | 6 | 7 | 3 |

| | COMPOUND | | | | | | | | | | | | | | | |
|---|---|---|---|---|---|---|---|---|---|---|---|---|---|---|---|---|
| Rate 1000 g/ha | 7 | 15 | 16 | 26 | 27 | 28 | 29 | 30 | 31 | 32 | 33 | 34 | 35 | 36 | 38 | 39 | 42 |
| PREEMERGENCE | | | | | | | | | | | | | | | | | |
| Barley | 1 | 0 | 0 | 0 | 0 | 1 | 0 | 2 | 3 | 6 | 4 | 0 | 1 | 1 | 2 | 0 | 0 |
| Bardyardgrass | 7 | 0 | 0 | 0 | 0 | 7 | 6 | 8 | 9 | 9 | 8 | 0 | 9 | 9 | 8 | 7 | 0 |
| Bedstraw | 1 | 0 | 0 | 0 | 3 | 10 | 2 | 8 | 8 | 6 | 6 | 0 | 10 | 10 | 3 | 4 | 0 |
| Blackgrass | 4 | 0 | 0 | 0 | 0 | 3 | 1 | 6 | 6 | 4 | 3 | 0 | 7 | 8 | 5 | 6 | 0 |
| Cheatgrass | 3 | 0 | 0 | 0 | 0 | 6 | 2 | 5 | 7 | 6 | 5 | 0 | 5 | 4 | 3 | 3 | 0 |
| Chickweed | 0 | 0 | 0 | 4 | 0 | 0 | 1 | 1 | 7 | 2 | 0 | 0 | 4 | 9 | 4 | 3 | 3 |
| Cocklebur | 0 | 0 | 0 | 0 | 0 | 1 | 0 | 2 | 9 | 3 | 3 | 0 | 2 | 10 | 3 | 3 | 0 |
| Corn | 0 | 0 | 0 | 0 | 0 | 2 | 0 | 3 | 6 | 5 | 3 | 0 | 6 | 7 | 1 | 3 | 0 |
| Cotton | 0 | 0 | 0 | 0 | 0 | 2 | 0 | 1 | 2 | 1 | 1 | 0 | 8 | 2 | 2 | 0 | 0 |
| Crabgrass | 7 | 0 | 0 | 0 | 0 | 8 | 5 | 9 | 9 | 9 | 9 | 2 | 9 | 9 | 7 | 9 | 0 |
| Downy brome | — | — | — | — | — | — | — | — | — | — | — | — | — | — | — | — | — |
| Giant foxtail | 8 | 0 | 0 | 0 | 0 | 6 | 4 | 7 | 9 | 8 | 5 | 2 | 9 | 9 | 7 | 8 | 0 |
| Lambsquarter | 9 | 0 | 7 | 0 | 4 | 10 | 9 | 10 | 10 | 10 | 10 | 0 | 10 | 10 | 10 | 10 | 9 |
| Morningglory | 3 | 0 | 0 | 0 | 0 | 6 | 2 | 2 | 10 | 10 | 2 | 0 | 9 | 10 | 4 | 4 | 0 |
| Nutsedge | 0 | 0 | 0 | 0 | 0 | 2 | 7 | 0 | 1 | 7 | 0 | 0 | 0 | 4 | 2 | 4 | 0 |
| Rape | 6 | 0 | 0 | 0 | 0 | 9 | 0 | 9 | 10 | 10 | 8 | 1 | 10 | 10 | 3 | 3 | 0 |
| Rice | 4 | 0 | 0 | 0 | 0 | 3 | 3 | 7 | 8 | 9 | 4 | 0 | 6 | 6 | 2 | 5 | 0 |
| Sorghum | 0 | 0 | 0 | 0 | 0 | 1 | 0 | 1 | 2 | 2 | 0 | 0 | 3 | 3 | 1 | 2 | 0 |
| Soybean | 0 | 0 | 0 | 0 | 0 | 7 | 0 | 6 | 6 | 5 | 6 | 0 | 8 | 5 | 0 | 1 | 0 |
| Sugar beet | 6 | 0 | 0 | 0 | 0 | 9 | 8 | 10 | 10 | 10 | 9 | 1 | 10 | 10 | 5 | 10 | 0 |
| Velvetleaf | 10 | 0 | 0 | 0 | 1 | 10 | 8 | 10 | 10 | 9 | 10 | 0 | 10 | 10 | 10 | 8 | 0 |
| Wheat | 3 | 0 | 0 | 0 | 0 | 6 | 0 | 6 | 5 | 6 | 5 | 0 | 2 | 6 | 2 | 0 | 0 |
| Wild buckwheat | 10 | 0 | 2 | 0 | 0 | 10 | 6 | 10 | 10 | 10 | 10 | 0 | 10 | 9 | 9 | 9 | 0 |
| Wild oat | 2 | 0 | 0 | 0 | 0 | 4 | 1 | 6 | 6 | 6 | 5 | 0 | 6 | 7 | 4 | 5 | 0 |

| | COMPOUND | | | | | | | | | | | | | | | |
|---|---|---|---|---|---|---|---|---|---|---|---|---|---|---|---|---|
| Rate 1000 g/ha | 43 | 44 | 45 | 46 | 47 | 48 | 49 | 50 | 51 | 52 | 53 | 54 | 55 | 56 | 57 | 58 |
| PREEMERGENCE | | | | | | | | | | | | | | | | |
| Barley | 0 | 0 | 0 | 2 | 2 | 1 | 0 | 0 | 1 | 1 | 1 | 1 | 1 | 2 | 2 | 1 |
| Bardyardgrass | 0 | 6 | 5 | 7 | 8 | 8 | 9 | 8 | 9 | 8 | 8 | 9 | 8 | 9 | 9 | 9 |
| Bedstraw | 0 | 0 | 0 | 7 | 6 | 2 | 8 | 9 | 7 | 9 | 9 | 5 | 9 | 6 | 9 | 9 |
| Blackgrass | 0 | 0 | 2 | 5 | 5 | 3 | 6 | 7 | 4 | 7 | 6 | 7 | 6 | 6 | 4 | 6 |

TABLE B-continued

| | | | | | | | | | | | | | | | | |
|---|---|---|---|---|---|---|---|---|---|---|---|---|---|---|---|---|
| Cheatgrass | 3 | 2 | 3 | 3 | 3 | 4 | 5 | 7 | 7 | 6 | 7 | 6 | 5 | 6 | 8 | 3 |
| Chickweed | 0 | 0 | 0 | 0 | 1 | 1 | 2 | 0 | 3 | 2 | 5 | 6 | 3 | 1 | 3 | 5 |
| Cocklebur | 0 | 2 | 3 | 1 | 0 | 2 | 6 | 8 | 0 | 5 | 2 | 6 | 0 | 4 | 5 | 4 |
| Corn | 0 | 2 | 3 | 0 | 3 | 3 | 4 | 5 | 4 | 5 | 4 | 5 | 3 | 6 | 4 | 3 |
| Cotton | 0 | 1 | 1 | 1 | 2 | 0 | 3 | 2 | 1 | 4 | 2 | 2 | 3 | 1 | 2 | 6 |
| Crabgrass | 3 | 7 | 6 | 5 | 9 | 9 | 10 | 9 | 9 | 9 | 9 | 9 | 9 | 9 | 10 | 9 |
| Downy brome | — | — | — | — | — | — | — | — | — | — | — | — | — | — | — | — |
| Giant foxtail | 0 | 5 | 3 | 5 | 9 | 8 | 10 | 10 | 9 | 10 | 9 | 9 | 10 | 9 | 9 | 9 |
| Lambsquarter | 10 | 9 | 10 | 10 | 10 | 9 | 10 | 10 | 9 | 9 | 10 | 10 | 10 | 10 | 10 | 10 |
| Morningglory | 0 | 2 | 2 | 1 | — | 2 | 8 | 7 | 3 | 4 | 2 | 6 | 1 | 3 | 6 | 7 |
| Nutsedge | 0 | 0 | 0 | 0 | 0 | 0 | 3 | — | 4 | 0 | 3 | 0 | 0 | 0 | 0 | 10 |
| Rape | 0 | 2 | 0 | 6 | 10 | 9 | 10 | 9 | 8 | 10 | 9 | 9 | 9 | 8 | 9 | 9 |
| Rice | 0 | 2 | 2 | 3 | 5 | 3 | 6 | 5 | 4 | 6 | 2 | 5 | 4 | 5 | 4 | 4 |
| Sorghum | 0 | 4 | 2 | 2 | 2 | 3 | 2 | 2 | 3 | 0 | 0 | 1 | 2 | 2 | 2 | 3 |
| Soybean | 0 | 6 | 4 | 1 | 5 | 2 | 8 | 6 | 6 | 7 | 6 | 4 | 8 | 2 | 8 | 6 |
| Sugar beet | 0 | 6 | 7 | 10 | 10 | 9 | 10 | 10 | 10 | 10 | 10 | 10 | 10 | 10 | 10 | 10 |
| Velvetleaf | 0 | 8 | 9 | — | 4 | 9 | 9 | 9 | 10 | 9 | 10 | 10 | 10 | 9 | 10 | 10 |
| Wheat | 0 | 0 | 0 | 3 | 4 | 2 | 3 | 3 | 3 | 4 | 3 | 2 | 5 | 6 | 6 | 6 |
| Wild buckwheat | 0 | 0 | 4 | 9 | 10 | 10 | 8 | 9 | 10 | 10 | 10 | 10 | 10 | 9 | 10 | 10 |
| Wild oat | 2 | 0 | 0 | 3 | 6 | 3 | 6 | 4 | 6 | 6 | 5 | 3 | 6 | 6 | 5 | 6 |

| | COMPOUND | | | | | | | | | | | | | | | |
|---|---|---|---|---|---|---|---|---|---|---|---|---|---|---|---|---|
| Rate 1000 g/ha | 59 | 60 | 61 | 63 | 64 | 65 | 66 | 70 | 71 | 72 | 73 | 74 | 75 | 76 | 77 | 78 |
| PREEMERGENCE | | | | | | | | | | | | | | | | |
| Barley | 2 | 0 | 0 | 0 | 0 | 0 | 0 | 0 | 8 | 0 | 0 | 0 | 5 | 5 | 4 | 2 |
| Bardyardgrass | 9 | 0 | 0 | 0 | 0 | 0 | 0 | 3 | 10 | 4 | 0 | 0 | 9 | 7 | 8 | 9 |
| Bedstraw | 5 | 4 | 0 | 4 | 4 | 0 | — | 9 | 10 | 10 | 10 | 0 | 10 | 10 | 10 | 8 |
| Blackgrass | 6 | 0 | 0 | 0 | 0 | 0 | 0 | 1 | 8 | 1 | 1 | 0 | 5 | 6 | 4 | 5 |
| Cheatgrass | 7 | 0 | 2 | 0 | 0 | 0 | 0 | 2 | 7 | 3 | 3 | 0 | 7 | 5 | 4 | 5 |
| Chickweed | 5 | 0 | 0 | 0 | 0 | 0 | 0 | 2 | 10 | 0 | 10 | 0 | 8 | 10 | 8 | 8 |
| Cocklebur | 4 | 0 | 0 | 0 | 0 | 0 | 0 | 0 | 7 | 0 | 0 | 0 | 3 | 7 | 0 | 6 |
| Corn | 3 | 0 | 0 | 0 | 0 | 0 | 0 | 2 | 8 | 0 | 0 | 0 | 4 | 0 | 2 | 1 |
| Cotton | 3 | 0 | 0 | 0 | 0 | 0 | 0 | 0 | 8 | 0 | 0 | 0 | 2 | 7 | 0 | 0 |
| Crabgrass | 9 | 0 | 0 | 0 | 0 | 0 | 0 | 9 | 10 | 9 | 1 | 0 | 9 | 10 | 9 | 10 |
| Downy brome | — | — | — | — | — | — | — | — | — | — | — | — | — | — | — | — |
| Giant foxtail | 9 | 0 | 0 | 0 | 0 | 0 | 0 | 3 | 10 | 4 | 0 | 0 | 10 | 9 | 9 | 9 |
| Lambsquarter | 10 | 3 | 0 | 6 | 0 | 0 | 0 | 10 | 10 | — | 7 | 0 | 10 | 10 | 10 | 10 |
| Morningglory | 10 | 0 | 0 | 0 | 2 | 0 | 0 | 1 | 9 | 1 | 3 | 0 | — | 5 | 7 | 8 |
| Nutsedge | 0 | 0 | 0 | 0 | 0 | 0 | 0 | 3 | 6 | 3 | 2 | 0 | 4 | 4 | 4 | 2 |
| Rape | 9 | 0 | 0 | 2 | 3 | 0 | 0 | 2 | 10 | 1 | 1 | 0 | 10 | 10 | 9 | 10 |
| Rice | 4 | 0 | 0 | 2 | 0 | 0 | 0 | 1 | 9 | 2 | 0 | 0 | 8 | 5 | 3 | 3 |
| Sorghum | 3 | 0 | 0 | 0 | 0 | 0 | 0 | 0 | 7 | 1 | 0 | 0 | 2 | 3 | 0 | 2 |
| Soybean | 5 | 0 | 0 | 0 | 0 | 0 | 0 | 0 | 9 | 0 | 0 | 0 | 8 | 6 | 4 | 6 |
| Sugar beet | 10 | 0 | 0 | 2 | 4 | 0 | 0 | 6 | 10 | 9 | 0 | 0 | 10 | 10 | 10 | 10 |
| Velvetleaf | 9 | 0 | 2 | 0 | 0 | 0 | 0 | 10 | 10 | 8 | 4 | 0 | 10 | 10 | 10 | 10 |
| Wheat | 3 | 0 | 0 | 0 | 0 | 0 | 0 | 2 | 7 | 2 | 0 | 0 | 6 | 6 | 6 | 5 |
| Wild buckwheat | 10 | 0 | 0 | — | 0 | 0 | 0 | 4 | 10 | — | 0 | 0 | 9 | 10 | 10 | 9 |
| Wild oat | 6 | 0 | 0 | 0 | 0 | 0 | 0 | 2 | 7 | 2 | 2 | 0 | 6 | 6 | 6 | 6 |

| | COMPOUND | | | | | | | | | | | | | | | |
|---|---|---|---|---|---|---|---|---|---|---|---|---|---|---|---|---|
| Rate 1000 g/ha | 79 | 80 | 81 | 82 | 83 | 84 | 85 | 86 | 87 | 88 | 90 | 91 | 92 | 97 | 98 | 100 |
| PREEMERGENCE | | | | | | | | | | | | | | | | |
| Barley | 1 | 1 | 1 | 4 | 3 | 7 | 1 | 2 | 0 | 0 | 2 | 2 | 7 | 6 | 7 | 9 |
| Bardyardgrass | 5 | 4 | 9 | 8 | 9 | 8 | 0 | 9 | 4 | 8 | 8 | 7 | 9 | 8 | 9 | 10 |
| Bedstraw | 5 | 10 | 10 | 10 | 8 | 10 | 5 | 8 | 0 | 10 | 3 | 4 | 10 | 10 | 10 | 10 |
| Blackgrass | 2 | 2 | 5 | 4 | 4 | 4 | 1 | 3 | 1 | 2 | 3 | 1 | 6 | 5 | 6 | 9 |
| Cheatgrass | 3 | 4 | 3 | 3 | 3 | 2 | 1 | 4 | 2 | 2 | 3 | 1 | 9 | 3 | 3 | 10 |
| Chickweed | 7 | 7 | 10 | 9 | 8 | 8 | 5 | 9 | 3 | 4 | 6 | 3 | 10 | 9 | 8 | 10 |
| Cocklebur | 0 | 0 | 6 | 9 | 3 | 5 | 3 | 7 | 4 | 3 | 0 | 6 | 10 | 2 | 3 | 10 |
| Corn | 0 | 0 | 2 | 2 | 0 | 2 | 0 | 2 | 1 | 0 | 2 | 5 | 9 | 5 | 6 | 10 |
| Cotton | 0 | 0 | 1 | 1 | 2 | 4 | 0 | 7 | 2 | 3 | 0 | 0 | 10 | 1 | 0 | 10 |
| Crabgrass | 8 | 6 | 10 | 10 | 10 | 10 | 7 | 9 | 3 | 9 | 7 | 6 | 10 | 8 | 9 | 10 |
| Downy brome | — | — | — | — | — | — | — | — | — | — | — | — | — | — | — | — |
| Giant foxtail | 6 | 6 | 8 | 9 | 9 | 8 | 4 | 9 | 3 | 10 | 6 | 6 | 9 | 6 | 8 | 10 |
| Lambsquarter | 10 | 10 | 10 | 10 | 10 | 10 | 10 | 10 | 10 | 8 | 9 | 9 | 10 | 10 | 10 | 10 |
| Morningglory | 9 | 2 | 9 | 10 | 6 | 9 | 3 | 9 | 4 | 2 | 3 | 4 | 10 | 10 | 2 | 10 |
| Nutsedge | 3 | 3 | 3 | 2 | 0 | 3 | 2 | 3 | 3 | 3 | 3 | 2 | 7 | 0 | 0 | 10 |
| Rape | 2 | 6 | 10 | 10 | 9 | 9 | 3 | 10 | 0 | 1 | 2 | 2 | 10 | 6 | 7 | 10 |
| Rice | 0 | 0 | 2 | 3 | 4 | 3 | 0 | 5 | 2 | 5 | 2 | 2 | 9 | 9 | 8 | 10 |
| Sorghum | 0 | 0 | 2 | 2 | 1 | 2 | 0 | 3 | 0 | 0 | 1 | 4 | 4 | 4 | 4 | 10 |
| Soybean | 1 | 1 | 6 | 3 | 3 | 6 | 0 | 6 | 2 | 0 | 2 | 2 | 9 | 6 | 2 | 8 |
| Sugar beet | 8 | 7 | 10 | 10 | 10 | 10 | 6 | 10 | 2 | 8 | 10 | 8 | 10 | 10 | 9 | 10 |
| Velvetleaf | 9 | 9 | 10 | 10 | 10 | 10 | 7 | 10 | 7 | 10 | 9 | 9 | 10 | 8 | 10 | 10 |

TABLE B-continued

| | | | | | | | | | | | | | | | |
|---|---|---|---|---|---|---|---|---|---|---|---|---|---|---|---|
| Wheat | 2 | 4 | 8 | 6 | 3 | 9 | 3 | 4 | 0 | 0 | 4 | 3 | 9 | 7 | 8 | 10 |
| Wild buckwheat | 9 | 2 | 10 | 10 | 10 | 10 | 9 | 10 | 6 | 9 | 9 | 9 | 10 | 10 | 9 | 10 |
| Wild oat | 2 | 2 | 4 | 6 | 3 | 8 | 4 | 5 | 0 | 0 | 6 | 3 | 8 | 7 | 7 | 10 |

| Rate 0.08 g/ha | COMPOUND 6 | Rate 0.08 g/ha | COMPOUND 6 |
|---|---|---|---|
| POSTEMERGENCE | | PREEMERGENCE | |
| Barley | 2 | Barley | 0 |
| Barnyardgrass | 2 | Barnyardgrass | 0 |
| Bedstraw | 2 | Bedstraw | 0 |
| Blackgrass | 2 | Blackgrass | 0 |
| Cheatgrass | 1 | Cheatgrass | 0 |
| Chickweed | 1 | Chickweed | 0 |
| Cocklebur | 5 | Cocklebur | 0 |
| Corn | 1 | Corn | 0 |
| Cotton | 7 | Cotton | 0 |
| Crabgrass | 2 | Crabgrass | 0 |
| Downy brome | — | Downy brome | — |
| Giant foxtail | 4 | Giant foxtail | 0 |
| Lambsquarter | 6 | Lambsquarter | — |
| Morningglory | 2 | Morningglory | 0 |
| Nutsedge | 1 | Nutsedge | 0 |
| Rape | 6 | Rape | 0 |
| Rice | 2 | Rice | 0 |
| Sorghum | 2 | Sorghum | 0 |
| Soybean | 3 | Soybean | 0 |
| Sugar beet | 6 | Sugar beet | 0 |
| Velvetleaf | 4 | Velvetleaf | 0 |
| Wheat | 1 | Wheat | 0 |
| Wild buckwheat | 2 | Wild buckwheat | 0 |
| Wild oat | 0 | Wild oat | 0 |

| Rate 0.02 g/ha | COMPOUND 6 | Rate 0.02 g/ha | COMPOUND 6 |
|---|---|---|---|
| POSTEMERGENCE | | PREEMERGENCE | |
| Barley | 1 | Barley | 0 |
| Barnyardgrass | 0 | Barnyardgrass | 0 |
| Bedstraw | 1 | Bedstraw | 0 |
| Blackgrass | 0 | Blackgrass | 0 |
| Cheatgrass | 0 | Cheatgrass | 0 |
| Chickweed | 0 | Chickweed | 0 |
| Cocklebur | 2 | Cocklebur | 0 |
| Corn | 1 | Corn | 0 |
| Cotton | 8 | Cotton | 0 |
| Crabgrass | 1 | Crabgrass | 0 |
| Downy brome | — | Downy brome | — |
| Giant foxtail | 1 | Giant foxtail | 0 |
| Lambsquarter | 4 | Lambsquarter | 0 |
| Morningglory | 1 | Morningglory | 0 |
| Nutsedge | 1 | Nutsedge | 0 |
| Rape | 0 | Rape | 0 |
| Rice | 2 | Rice | 0 |
| Sorghum | 1 | Sorghum | 0 |
| Soybean | 1 | Soybean | 0 |
| Sugar beet | 2 | Sugar beet | 0 |
| Velvetleaf | 1 | Velvetleaf | 0 |
| Wheat | 1 | Wheat | 0 |
| Wild buckwheat | 1 | Wild buckwheat | 0 |
| Wild oat | 0 | Wild oat | 0 |

| | COMPOUND | | | | | | | | | | | | | | |
|---|---|---|---|---|---|---|---|---|---|---|---|---|---|---|---|
| Rate 400 g/ha | 1 | 3 | 4 | 5 | 6 | 10 | 11 | 12 | 13 | 17 | 18 | 19 | 20 | 21 | 22 | 23 |
| POSTEMERGENCE | | | | | | | | | | | | | | | | |
| Barley | 0 | 0 | 0 | 1 | 2 | 2 | 2 | 0 | 0 | 0 | 0 | 1 | 0 | 2 | 4 | 0 |
| Barnyardgrass | 0 | 0 | 0 | 1 | 3 | 1 | 1 | 0 | 0 | 0 | 1 | 1 | 1 | 4 | — | 0 |
| Bedstraw | 2 | 0 | 1 | 2 | 6 | 1 | 1 | 0 | 0 | 0 | 1 | 1 | 0 | 1 | 5 | 0 |
| Blackgrass | 0 | 1 | 0 | 1 | 3 | 1 | 1 | 0 | 0 | 0 | 1 | 0 | 0 | 1 | 2 | 0 |
| Cheatgrass | 0 | 0 | 0 | 1 | 3 | 1 | 0 | 0 | 0 | 0 | 0 | 0 | 0 | 1 | 2 | 0 |
| Chickweed | 1 | 0 | 0 | 0 | — | 0 | 0 | 0 | 0 | 0 | 0 | 0 | 0 | 1 | 4 | 0 |
| Cocklebur | 2 | 0 | 0 | 1 | 7 | 2 | 1 | 0 | 0 | 0 | 0 | 0 | 0 | 3 | 6 | 0 |
| Corn | 0 | 0 | 0 | 1 | 3 | 1 | 1 | 0 | 0 | 0 | 1 | 0 | 0 | 2 | — | 0 |
| Cotton | 8 | 1 | 1 | 8 | 9 | 9 | 9 | 0 | 0 | 0 | 0 | 0 | 1 | 9 | — | 0 |

TABLE B-continued

| | | | | | | | | | | | | | | | | |
|---|---|---|---|---|---|---|---|---|---|---|---|---|---|---|---|---|
| Crabgrass | 1 | 1 | 0 | 0 | 3 | 2 | 2 | 0 | 0 | 0 | 1 | 1 | 0 | 3 | 6 | 0 |
| Downy brome | — | — | — | — | — | — | — | — | — | — | — | — | — | — | — | — |
| Giant foxtail | 0 | 1 | 0 | 1 | 4 | 1 | 2 | 0 | 0 | 0 | 1 | — | 0 | 3 | 5 | 0 |
| Lambsquarter | 4 | — | 0 | — | 5 | 6 | 6 | 0 | — | 0 | 1 | 0 | 5 | 8 | 9 | 1 |
| Morningglory | 2 | 0 | 0 | 2 | 6 | 4 | 2 | 0 | 0 | 0 | 0 | 0 | 0 | 4 | 8 | 0 |
| Nutsedge | 0 | 0 | 0 | 0 | 1 | 0 | 0 | 0 | 0 | 0 | 0 | 0 | 0 | 0 | 2 | 0 |
| Rape | 0 | 1 | 0 | 1 | 7 | 1 | 1 | 0 | 0 | 2 | 0 | 0 | 0 | 2 | 5 | 0 |
| Rice | 0 | 0 | 0 | 2 | 4 | 2 | 2 | 0 | 0 | 0 | 0 | 1 | 0 | 3 | 4 | 0 |
| Sorghum | 0 | 0 | 0 | 0 | 4 | 2 | 2 | 0 | 0 | 0 | 0 | 1 | 1 | 4 | — | 0 |
| Soybean | 0 | 0 | 0 | 0 | 5 | 3 | 3 | 0 | 0 | 0 | 0 | 0 | 1 | 4 | — | 0 |
| Sugar beet | 2 | 0 | 0 | 1 | 9 | 6 | 6 | 0 | 0 | 2 | 0 | 0 | 0 | 4 | 9 | 0 |
| Velvetleaf | 1 | 0 | 0 | 2 | 8 | 3 | 2 | 0 | 0 | 0 | 0 | 0 | 0 | — | 7 | 0 |
| Wheat | 0 | 0 | 1 | 0 | 2 | 2 | 2 | 0 | 0 | 0 | 0 | 0 | 0 | 0 | 5 | 0 |
| Wild buckwheat | 0 | 1 | 1 | 3 | 6 | 1 | 1 | 0 | 0 | 0 | 0 | 2 | 2 | 2 | 9 | 0 |
| Wild oat | 0 | 0 | 0 | 0 | 2 | 1 | 1 | 0 | 0 | 0 | 0 | 0 | 0 | 0 | 4 | 0 |

| | COMPOUND | | | | | | | | | | |
|---|---|---|---|---|---|---|---|---|---|---|---|
| Rate 400 g/ha | 24 | 37 | 40 | 41 | 101 | 102 | 103 | 104 | 106 | 108 | 109 |
| POSTEMERGENCE | | | | | | | | | | | |
| Barley | 2 | 5 | 2 | 1 | 4 | 4 | 2 | 1 | 3 | — | 0 |
| Barnyardgrass | 3 | 5 | 3 | 1 | 2 | 2 | 2 | 2 | 3 | 2 | 1 |
| Bedstraw | 3 | 8 | 1 | 1 | 8 | 5 | 1 | 0 | 5 | — | — |
| Blackgrass | 1 | 3 | 1 | 0 | 2 | 1 | 1 | 1 | 2 | — | 1 |
| Cheatgrass | 2 | 5 | 0 | 1 | — | — | — | — | — | — | — |
| Chickweed | 1 | 5 | 0 | 0 | 3 | 3 | 3 | 0 | 3 | — | 3 |
| Cocklebur | 6 | 8 | 2 | 1 | 4 | 5 | 1 | 1 | 7 | 6 | 4 |
| Corn | 2 | 4 | 2 | 1 | 1 | 1 | 1 | 1 | 3 | 3 | 1 |
| Cotton | 9 | 10 | 9 | 8 | 9 | 9 | 8 | 9 | 10 | 10 | 10 |
| Crabgrass | 4 | 7 | 3 | 3 | 3 | 2 | 2 | 3 | 6 | 2 | 2 |
| Downy brome | — | — | — | — | 0 | 3 | 0 | 0 | 2 | — | 0 |
| Giant foxtail | 3 | — | 2 | 2 | 4 | 2 | 2 | 2 | 4 | 2 | 2 |
| Lambsquarter | 4 | 10 | 7 | 5 | 3 | 3 | 1 | 3 | 3 | — | 3 |
| Morningglory | 8 | 9 | 2 | 1 | 6 | 4 | 1 | 2 | 9 | 10 | 7 |
| Nutsedge | 4 | 8 | 0 | 0 | 1 | 1 | — | — | 3 | — | 1 |
| Rape | 5 | 6 | 1 | 0 | 7 | 7 | 2 | 1 | 3 | — | 5 |
| Rice | 2 | 8 | 3 | 2 | 5 | 4 | 1 | 1 | 5 | 6 | 2 |
| Sorghum | 3 | 4 | 3 | 2 | 2 | 2 | 2 | 2 | 5 | 2 | 2 |
| Soybean | 4 | 7 | 3 | 2 | 5 | 5 | 3 | 4 | 7 | 6 | 3 |
| Sugar beet | 6 | 10 | 6 | 3 | 9 | 8 | 3 | 3 | 8 | — | 8 |
| Velvetleaf | 5 | 9 | 8 | 2 | 5 | 5 | 1 | 5 | 6 | 9 | 5 |
| Wheat | 2 | 7 | 1 | 1 | 4 | 4 | 2 | 2 | 3 | — | 2 |
| Wild buckwheat | 5 | 10 | 1 | 1 | 9 | 7 | 7 | 2 | 3 | — | 3 |
| Wild oat | 2 | 3 | 1 | 1 | 1 | 2 | 1 | 2 | 4 | — | 0 |

| | COMPOUND | | | | | | | | | | | | | | | |
|---|---|---|---|---|---|---|---|---|---|---|---|---|---|---|---|---|
| Rate 400 g/ha | 1 | 3 | 4 | 5 | 6 | 8 | 10 | 11 | 12 | 13 | 17 | 18 | 19 | 20 | 21 | 22 |
| PREEMERGENCE | | | | | | | | | | | | | | | | |
| Barley | 0 | 0 | 0 | 0 | 0 | 0 | 0 | 0 | 0 | 0 | 0 | 0 | 0 | 0 | 0 | 1 |
| Barnyardgrass | 0 | 0 | 0 | 0 | 2 | 0 | 0 | 0 | 0 | 0 | 0 | 0 | 0 | 0 | 0 | 7 |
| Bedstraw | 3 | 0 | 0 | 0 | 9 | 0 | 0 | 0 | 0 | 0 | 0 | 0 | 0 | 0 | 0 | 6 |
| Blackgrass | — | 0 | 0 | 0 | 3 | 0 | 0 | 0 | 0 | 0 | 0 | 0 | 0 | 2 | 0 | 2 |
| Cheatgrass | 0 | 0 | 0 | 0 | 0 | 0 | 0 | 0 | 0 | 0 | 0 | 0 | 0 | 4 | 0 | 3 |
| Chickweed | 2 | 0 | 0 | 0 | 0 | 0 | 0 | 0 | 0 | 0 | 0 | 0 | 0 | 0 | 0 | 4 |
| Cocklebur | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 1 |
| Cotton | 0 | 0 | 0 | 0 | 0 | 0 | 0 | 0 | 0 | 0 | 0 | 0 | 0 | 0 | 0 | 0 |
| Crabgrass | 1 | 0 | 0 | 0 | 4 | 0 | 0 | 0 | 0 | 0 | 0 | 0 | 0 | 0 | 0 | 7 |
| Downy brome | — | — | — | — | — | — | — | — | — | — | — | — | — | — | — | — |
| Giant foxtail | 0 | 0 | 0 | 0 | 3 | 0 | 0 | 6 | 0 | 0 | 0 | 0 | 0 | 0 | 0 | 6 |
| Lambsquarter | 0 | 0 | 0 | 0 | 8 | 0 | 10 | 0 | 0 | 0 | 0 | 0 | 0 | 6 | 9 | 7 |
| Morningglory | 0 | 0 | 0 | 0 | 0 | 0 | 0 | 0 | — | 0 | 0 | 0 | 0 | 0 | 0 | 1 |
| Nutsedge | 0 | 0 | 0 | 0 | 0 | 0 | 0 | 0 | 0 | 0 | 0 | 0 | 0 | 0 | — | 0 |
| Rape | 0 | 0 | 0 | 0 | 2 | 0 | 0 | 0 | 0 | 0 | 0 | 0 | 0 | 0 | 0 | 2 |
| Rice | 0 | 0 | 0 | 0 | 0 | 0 | 2 | 0 | 0 | 0 | 0 | 0 | 0 | 0 | 0 | 2 |
| Sorghum | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 |
| Sugar beet | 2 | 0 | 0 | 0 | 3 | 0 | 1 | 0 | 0 | 0 | 0 | 0 | 0 | 2 | 0 | 9 |
| Velvetleaf | 1 | 0 | 0 | 0 | 10 | 0 | 0 | 0 | 0 | 0 | 0 | 0 | — | 0 | 0 | 6 |
| Wheat | 0 | 0 | 0 | 0 | 0 | 0 | 0 | 0 | 0 | 0 | 0 | 0 | 0 | 0 | 0 | 4 |
| Wild buckwheat | 0 | 0 | 0 | 0 | 10 | 0 | 0 | 0 | 0 | 0 | 0 | 0 | 0 | 0 | 0 | 6 |
| Wild oat | 0 | 0 | 0 | 0 | 0 | 0 | 0 | 0 | 0 | 0 | 0 | 0 | 0 | 0 | 0 | 3 |

TABLE B-continued

| Rate 400 g/ha | COMPOUND | | | | | | | | | | | | |
|---|---|---|---|---|---|---|---|---|---|---|---|---|---|
| | 23 | 24 | 37 | 40 | 41 | 95 | 101 | 102 | 103 | 104 | 106 | 108 | 109 |
| PREEMERGENCE | | | | | | | | | | | | | |
| Barley | 0 | 0 | 1 | 0 | 0 | 0 | 0 | 1 | 0 | 0 | 9 | 0 | 0 |
| Barnyardgrass | 0 | 0 | 8 | 0 | 0 | 0 | 0 | 0 | 7 | 0 | 9 | 3 | 1 |
| Bedstraw | 0 | 0 | 2 | 0 | 0 | 0 | 0 | 9 | 8 | 0 | 10 | — | — |
| Blackgrass | 0 | 0 | 3 | 0 | 0 | 0 | 1 | 2 | 5 | 0 | 8 | 1 | 2 |
| Cheatgrass | 0 | 0 | 4 | 0 | 0 | 0 | — | — | — | — | — | — | — |
| Chickweed | 0 | 0 | 10 | 0 | 0 | 0 | 0 | 2 | 4 | 0 | 10 | 1 | 0 |
| Cocklebur | 0 | 2 | 1 | 0 | 0 | 0 | 0 | 0 | 0 | 0 | 10 | 4 | 0 |
| Corn | 0 | 0 | 3 | 0 | 0 | 0 | 0 | 0 | 0 | 0 | 9 | 2 | 0 |
| Cotton | 0 | 0 | 4 | 2 | 0 | 0 | 0 | 0 | 0 | 1 | 9 | 1 | 0 |
| Crabgrass | 1 | 0 | 9 | 7 | 0 | 0 | 2 | 2 | 4 | 0 | 10 | 1 | 0 |
| Downy brome | — | — | — | — | — | — | 3 | 2 | 3 | 0 | 8 | 3 | 0 |
| Giant foxtail | 0 | 0 | 5 | 2 | 2 | 0 | 1 | 0 | 3 | 0 | 9 | 4 | 0 |
| Lambsquarter | 0 | 9 | 10 | 3 | 8 | 3 | 5 | 3 | 10 | 1 | 10 | 1 | 2 |
| Morningglory | 0 | 2 | 9 | 0 | 0 | 0 | 0 | 1 | 0 | 0 | 10 | 3 | 1 |
| Nutsedge | 0 | — | 2 | 0 | 0 | 0 | 0 | — | 0 | 0 | 9 | 2 | 0 |
| Rape | 0 | 0 | 3 | 0 | 0 | 0 | 6 | 2 | 7 | 4 | 10 | 2 | 2 |
| Rice | 0 | 0 | 5 | 0 | 0 | 0 | 4 | 0 | 6 | 0 | 9 | 6 | 4 |
| Sorghum | 0 | 0 | 2 | 0 | 0 | 0 | 0 | 0 | 4 | 0 | 9 | 1 | 0 |
| Soybean | 0 | 0 | 0 | 2 | 0 | 0 | 3 | 0 | 4 | 0 | 9 | 2 | 0 |
| Sugar beet | 0 | 6 | 10 | 0 | 0 | 2 | 3 | 5 | 6 | 2 | 10 | 8 | 1 |
| Velvetleaf | 0 | 5 | 10 | 3 | 2 | 0 | 0 | 0 | 0 | 0 | 10 | 9 | 0 |
| Wheat | 0 | 0 | 5 | 0 | 0 | 0 | 0 | 0 | 0 | 0 | 10 | 0 | 2 |
| Wild buckwheat | 0 | 0 | 10 | 0 | 0 | 0 | 2 | 2 | — | 3 | 10 | 6 | 2 |
| Wild oat | 0 | 0 | 6 | 0 | 0 | 0 | 0 | 0 | 2 | 0 | 9 | 0 | 0 |

| Rate 200 g/ha | COMPOUND | | | | | | | | | | | | | | | | |
|---|---|---|---|---|---|---|---|---|---|---|---|---|---|---|---|---|---|
| | 7 | 9 | 15 | 16 | 26 | 27 | 28 | 29 | 30 | 31 | 32 | 33 | 34 | 35 | 36 | 38 | 39 | 42 |
| POSTEMERGENCE | | | | | | | | | | | | | | | | | | |
| Barley | 2 | 0 | 0 | 0 | 0 | 1 | 4 | 2 | 3 | 4 | 4 | 3 | 1 | 5 | 5 | 4 | 5 | 2 |
| Barnyardgrass | 3 | 2 | 0 | — | 0 | 2 | 3 | 2 | 3 | 7 | 7 | 3 | 0 | 7 | 4 | 2 | 4 | 2 |
| Bedstraw | 3 | 1 | 0 | 2 | 0 | 2 | 6 | 2 | 4 | 6 | 6 | 6 | 0 | 7 | 5 | 3 | 4 | 1 |
| Blackgrass | 2 | 0 | 0 | 1 | 0 | 1 | 3 | 1 | 3 | 2 | 3 | 2 | 0 | 4 | 4 | 3 | 3 | 0 |
| Cheatgrass | 2 | 0 | 0 | 0 | 0 | 1 | 3 | 1 | 2 | 2 | 3 | 3 | 0 | 5 | 3 | 1 | 2 | 0 |
| Chickweed | — | 0 | 0 | 0 | 0 | 0 | 3 | 0 | 3 | 3 | 3 | 2 | 0 | 4 | 5 | 4 | 4 | 0 |
| Cocklebur | 5 | 1 | 0 | 3 | 0 | 1 | 4 | 2 | 4 | 6 | 5 | 4 | 0 | 7 | 6 | 3 | 7 | 2 |
| Corn | 2 | 2 | 0 | — | 0 | 2 | 3 | 3 | 3 | 3 | 3 | 3 | 0 | 3 | 2 | 3 | 3 | 1 |
| Cotton | 9 | 9 | 0 | — | 0 | 5 | 9 | 9 | 10 | 9 | 10 | 10 | 0 | 10 | 9 | 8 | 9 | 5 |
| Crabgrass | 3 | 2 | 0 | 3 | 0 | 4 | 5 | 2 | 4 | 6 | 5 | 5 | 0 | 5 | 2 | 2 | 2 | 1 |
| Downy brome | — | — | — | — | — | — | — | — | — | — | — | — | — | — | — | — | — | — |
| Giant foxtail | 3 | 1 | 0 | 3 | 0 | 2 | 3 | 2 | 4 | 5 | 6 | 6 | 0 | 5 | 3 | 2 | 3 | 1 |
| Lambsquarter | 8 | 1 | — | 2 | 0 | 6 | 10 | 7 | 7 | 9 | 9 | 8 | 0 | 10 | 9 | 8 | 8 | — |
| Morningglory | 4 | 1 | 0 | 4 | 0 | 1 | 4 | 3 | 6 | 7 | 8 | 8 | 0 | 9 | 8 | 7 | 9 | 1 |
| Nutsedge | 0 | 0 | 0 | 0 | 0 | 4 | 2 | 1 | 3 | 4 | 3 | 5 | 0 | 3 | 0 | 0 | 0 | — |
| Rape | 2 | 0 | 0 | 0 | 0 | 1 | 5 | 1 | 6 | 4 | 3 | 3 | 0 | 8 | 4 | 4 | 5 | 1 |
| Rice | 4 | 2 | 0 | 3 | 0 | 3 | 4 | 2 | 4 | 7 | 4 | 4 | 0 | 7 | 3 | 3 | 4 | 2 |
| Sorghum | 4 | 2 | 0 | — | 0 | 3 | 4 | 2 | 5 | 5 | 5 | 5 | 0 | 6 | 3 | 2 | 3 | 2 |
| Soybean | 3 | 0 | 0 | — | 0 | 3 | 5 | 2 | 4 | 5 | 5 | 4 | 0 | 9 | 7 | 3 | 6 | 1 |
| Sugar beet | 9 | 4 | 0 | 4 | 0 | 3 | 10 | 2 | 7 | 8 | 9 | 2 | 0 | 10 | 9 | 9 | 9 | 2 |
| Velvetleaf | 8 | 2 | 0 | 5 | 0 | 4 | 9 | 7 | 6 | 8 | 10 | 6 | 0 | 10 | 6 | 2 | 3 | 3 |
| Wheat | 2 | 1 | 0 | 0 | 0 | 0 | 2 | 1 | 2 | 4 | 2 | 2 | 0 | 4 | 6 | 4 | 4 | 0 |
| Wild buckwheat | 7 | 2 | 0 | 2 | 0 | 1 | 8 | 1 | 5 | 4 | 4 | 4 | 0 | 10 | 6 | 7 | 9 | 1 |
| Wild oat | 3 | 1 | 0 | 0 | 0 | 0 | 2 | 0 | 2 | 2 | 1 | 1 | 0 | 4 | 5 | 3 | 3 | 1 |

| Rate 200 g/ha | COMPOUND | | | | | | | | | | | | | | | | |
|---|---|---|---|---|---|---|---|---|---|---|---|---|---|---|---|---|---|
| | 43 | 44 | 45 | 46 | 47 | 48 | 49 | 50 | 51 | 52 | 53 | 54 | 55 | 56 | 57 | 58 | 59 | 60 |
| POSTEMERGENCE | | | | | | | | | | | | | | | | | | |
| Barley | 1 | 3 | 2 | 2 | 3 | 2 | 3 | 2 | 3 | 2 | 2 | 2 | 2 | 2 | 3 | 2 | 3 | 0 |
| Barnyardgrass | 2 | 2 | 1 | 3 | 3 | 3 | 3 | 4 | 3 | 4 | 3 | 2 | 2 | 3 | 4 | 3 | 3 | 0 |
| Bedstraw | 1 | 2 | 2 | 2 | 5 | 3 | 3 | 3 | 6 | 4 | 4 | 3 | 4 | 5 | 2 | 2 | 4 | 0 |
| Blackgrass | 1 | 1 | 1 | 1 | 2 | 1 | 3 | 2 | 2 | 1 | 3 | 2 | 3 | 3 | 2 | 2 | 2 | 0 |
| Cheatgrass | 1 | 1 | 1 | 0 | 0 | 1 | 2 | 1 | — | — | 1 | — | — | 2 | 2 | — | — | 0 |
| Chickweed | 0 | 0 | 1 | 1 | 2 | 2 | 2 | 2 | 3 | 2 | 3 | 2 | 2 | 2 | 1 | 2 | 2 | 0 |
| Cocklebur | 1 | 4 | 3 | 3 | 3 | 5 | 4 | 5 | 3 | 4 | 4 | 2 | 3 | 3 | 3 | 6 | 3 | 0 |
| Corn | 1 | 2 | 1 | 1 | 3 | 3 | 3 | 3 | 3 | 4 | 2 | 3 | 2 | 2 | 3 | 3 | 2 | 0 |
| Cotton | 5 | 9 | 8 | 9 | 8 | 9 | 9 | 10 | 9 | 10 | 9 | 9 | 9 | 10 | 9 | 9 | 9 | 0 |
| Crabgrass | 1 | 2 | — | 1 | 3 | 3 | 3 | 3 | 5 | 5 | 3 | 3 | 3 | 3 | 2 | 4 | 2 | 0 |
| Downy brome | — | — | — | — | — | — | — | — | — | — | — | — | — | — | — | — | — | — |

TABLE B-continued

| | | | | | | | | | | | | | | | | | |
|---|---|---|---|---|---|---|---|---|---|---|---|---|---|---|---|---|---|
| Giant foxtail | 1 | 2 | 2 | 3 | 3 | 2 | 3 | 3 | 3 | 3 | 4 | 3 | 2 | 3 | 2 | 3 | 3 | 0 |
| Lambsquarter | 3 | 4 | — | — | 5 | 6 | 7 | — | 8 | 5 | 6 | 3 | 7 | 7 | 8 | 7 | 7 | 0 |
| Morningglory | 3 | 6 | 6 | 5 | 4 | 7 | 7 | 5 | 2 | 4 | 6 | 3 | 6 | 5 | 4 | 7 | 5 | 0 |
| Nutsedge | 0 | 1 | 0 | 0 | 2 | 1 | 2 | 2 | 1 | 2 | 3 | 2 | 1 | 1 | 1 | 2 | 2 | 0 |
| Rape | 2 | 3 | 2 | 2 | 3 | 2 | 3 | 2 | 3 | 2 | 1 | 2 | 4 | 5 | 2 | 3 | 1 | 0 |
| Rice | 2 | 3 | 2 | 2 | 3 | 3 | 4 | 4 | 6 | 5 | 6 | 3 | 3 | 4 | 3 | 4 | 2 | 0 |
| Sorghum | 3 | 3 | 3 | 3 | 3 | 3 | 3 | 5 | 3 | 4 | 3 | 3 | 4 | 4 | 4 | 4 | 3 | 0 |
| Soybean | 0 | 3 | 3 | 3 | 2 | 2 | 2 | 4 | 3 | 5 | 2 | 5 | 3 | 3 | 3 | 6 | 3 | 0 |
| Sugar beet | 1 | 4 | 6 | 2 | 5 | 6 | 5 | 7 | 7 | 8 | 5 | 9 | 6 | 8 | 3 | 5 | 6 | 0 |
| Velvetleaf | 3 | 4 | 2 | 5 | 6 | 5 | 8 | 5 | 5 | 5 | 7 | 7 | 6 | 7 | 6 | 3 | 4 | 0 |
| Wheat | 1 | 0 | 2 | 1 | 1 | 0 | 1 | 1 | 1 | 1 | 2 | 1 | 1 | 2 | 2 | 2 | 1 | 0 |
| Wild buckwheat | 1 | 3 | 2 | 1 | 4 | 3 | 3 | 5 | 4 | 2 | 3 | 4 | 4 | 6 | 4 | 2 | 1 | 1 |
| Wild oat | 2 | 1 | 1 | 2 | 2 | 1 | 2 | 1 | 2 | 2 | 2 | 3 | 3 | 2 | 2 | 2 | 2 | 0 |

| | COMPOUND | | | | | | | | | | | | | | | |
|---|---|---|---|---|---|---|---|---|---|---|---|---|---|---|---|---|
| Rate 200 g/ha | 61 | 63 | 64 | 65 | 66 | 70 | 71 | 72 | 73 | 74 | 75 | 76 | 77 | 78 | 79 | 80 | 81 |
| POSTEMERGENCE | | | | | | | | | | | | | | | | | |
| Barley | 0 | 0 | 1 | 0 | 0 | 2 | 4 | 1 | 2 | 0 | 3 | 4 | 3 | 1 | 3 | 3 | 3 |
| Barnyardgrass | 0 | 0 | 0 | 0 | 1 | 1 | 8 | 0 | 0 | 0 | 3 | 6 | 3 | 7 | 1 | 0 | 6 |
| Bedstraw | 1 | 0 | 2 | 0 | 0 | 2 | 7 | 2 | 1 | 0 | 5 | 5 | 3 | 3 | 1 | 1 | 3 |
| Blackgrass | 1 | 0 | 1 | 0 | 0 | 2 | 3 | 1 | 1 | 0 | 2 | 3 | 2 | 3 | 2 | 2 | 2 |
| Cheatgrass | 0 | 0 | — | 0 | 0 | 0 | 2 | 1 | 0 | 0 | 3 | 3 | 2 | 4 | 1 | 2 | 2 |
| Chickweed | 0 | 0 | 0 | 0 | 0 | 1 | 3 | 1 | 0 | 0 | 3 | 3 | 2 | 2 | 2 | 2 | 2 |
| Cocklebur | 0 | 0 | 0 | 0 | 0 | 2 | 4 | 0 | 1 | 0 | 3 | 7 | 5 | 6 | 2 | 2 | 6 |
| Corn | 0 | 0 | 0 | 0 | 0 | 1 | 2 | 0 | 0 | 0 | 3 | 3 | 2 | 2 | 2 | 1 | 2 |
| Cotton | 0 | 0 | 0 | 0 | 0 | 9 | 10 | 7 | 2 | 0 | 9 | 10 | 6 | 9 | 9 | 9 | 9 |
| Crabgrass | 0 | 0 | 0 | 0 | 1 | 1 | 8 | 0 | 1 | 0 | 5 | 6 | 3 | 8 | 2 | 1 | 2 |
| Downy brome | — | — | — | — | — | — | — | — | — | — | — | — | — | — | — | — | — |
| Giant foxtail | 0 | 0 | 0 | 0 | 1 | 2 | 7 | 1 | 0 | 0 | 2 | 5 | 3 | 7 | 1 | 2 | 3 |
| Lambsquarter | 4 | — | 2 | 0 | 1 | — | 9 | 0 | — | 0 | 9 | 10 | 8 | — | — | — | — |
| Morningglory | 2 | 2 | 0 | 0 | 1 | 3 | 8 | 2 | 2 | 0 | 3 | 8 | 6 | 8 | 7 | 6 | 7 |
| Nutsedge | 0 | 0 | 0 | 0 | 0 | 1 | 3 | 1 | 0 | 0 | 1 | 2 | 2 | 3 | 2 | 1 | 1 |
| Rape | 0 | 0 | 0 | 0 | 0 | 2 | 6 | 1 | 1 | 0 | 3 | 5 | 1 | 3 | 4 | 2 | 3 |
| Rice | 0 | 0 | 0 | 0 | 0 | 2 | 6 | 2 | 2 | 0 | 3 | 4 | 3 | 7 | 2 | 2 | 2 |
| Sorghum | 0 | 0 | 0 | 0 | 1 | 2 | 6 | 0 | 1 | 0 | 3 | 3 | 4 | 4 | 2 | 2 | 4 |
| Soybean | 0 | 0 | 0 | 0 | 1 | 2 | 7 | 2 | 1 | 0 | 3 | 3 | 3 | 3 | 2 | 1 | 2 |
| Sugar beet | 6 | 0 | 3 | 0 | 0 | 3 | 9 | 2 | 3 | 0 | 7 | 8 | 4 | 9 | 3 | 4 | 5 |
| Velvetleaf | 0 | 0 | 0 | 0 | 1 | 3 | 8 | 1 | 1 | 0 | 7 | 7 | 4 | 10 | 2 | 2 | 5 |
| Wheat | 0 | 0 | 1 | 0 | 0 | 1 | 5 | 2 | 0 | 0 | 3 | 2 | 3 | 2 | 3 | 2 | 3 |
| Wild buckwheat | 1 | 0 | 1 | 0 | 0 | 2 | 6 | 0 | 1 | 0 | 10 | 8 | 6 | 10 | 2 | 2 | 7 |
| Wild oat | 0 | 0 | 1 | 0 | 0 | 0 | 5 | 1 | 0 | 0 | 3 | 3 | 1 | 4 | 3 | 2 | 3 |

| | COMPOUND | | | | | | | | | | | | | | | |
|---|---|---|---|---|---|---|---|---|---|---|---|---|---|---|---|---|
| Rate 200 g/ha | 82 | 83 | 84 | 85 | 86 | 87 | 88 | 90 | 91 | 92 | 93 | 94 | 96 | 97 | 98 | 100 | 110 |
| POSTEMERGENCE | | | | | | | | | | | | | | | | | |
| Barley | 4 | 4 | 4 | 2 | 3 | 1 | 0 | 3 | 3 | 4 | 0 | 8 | 4 | 2 | 4 | 2 | 0 |
| Barnyardgrass | 7 | 2 | 1 | 0 | 3 | 0 | 1 | 2 | 2 | 6 | 0 | 10 | 7 | 2 | 3 | 3 | 2 |
| Bedstraw | 5 | 4 | 3 | 3 | 4 | 2 | 3 | 3 | 3 | 8 | 0 | 10 | 6 | 4 | 5 | 4 | — |
| Blackgrass | 3 | 3 | 2 | 2 | 3 | 1 | 0 | 2 | 3 | 4 | 1 | 8 | 4 | 2 | 2 | 1 | 2 |
| Cheatgrass | 3 | 3 | 3 | 1 | 3 | 1 | 0 | 3 | 2 | 4 | 0 | 9 | 4 | 2 | 1 | 1 | — |
| Chickweed | 4 | 4 | 3 | 3 | 6 | 1 | 2 | 2 | 2 | 6 | 0 | 7 | 6 | 3 | 3 | 2 | 2 |
| Cocklebur | 5 | 3 | 3 | 1 | 6 | 1 | 1 | 3 | 2 | 7 | 0 | 9 | 4 | 4 | 4 | 4 | 1 |
| Corn | 2 | 2 | 2 | 0 | 2 | 0 | 1 | 2 | 2 | 4 | 0 | 7 | 2 | 2 | 3 | 4 | 1 |
| Cotton | 9 | 9 | 9 | 3 | 10 | 4 | 9 | 10 | 9 | 9 | 0 | 10 | 10 | 9 | 9 | 9 | 6 |
| Crabgrass | 4 | 2 | 3 | 0 | 6 | 0 | 1 | 4 | 3 | 7 | 0 | 8 | 5 | 2 | 2 | 3 | 1 |
| Downy brome | — | — | — | — | — | — | — | — | — | — | — | — | — | — | — | — | 0 |
| Giant foxtail | 5 | 2 | 2 | 0 | 5 | 0 | 2 | 3 | 2 | 9 | 0 | 9 | 7 | 2 | 3 | 3 | 3 |
| Lambsquarter | — | — | 8 | 7 | 9 | — | 6 | 4 | 7 | 10 | 0 | 10 | 10 | 4 | 8 | 2 | 2 |
| Morningglory | 6 | 7 | 7 | 3 | 8 | 3 | 4 | 6 | 7 | 9 | 0 | 9 | 10 | 5 | 8 | 5 | 6 |
| Nutsedge | 3 | 2 | 3 | 1 | 4 | 1 | 1 | 2 | 3 | 4 | 0 | 7 | 3 | 1 | 2 | 2 | 1 |
| Rape | 5 | 4 | 3 | 2 | 5 | 3 | 3 | 1 | 1 | 6 | 0 | 9 | 9 | 3 | 2 | 3 | 2 |
| Rice | 5 | 3 | 3 | 1 | 5 | 1 | 2 | 3 | 3 | 8 | 0 | 10 | 6 | 4 | 4 | 7 | 2 |
| Sorghum | 3 | 3 | 3 | 1 | 4 | 0 | 3 | 2 | 4 | 3 | 1 | 9 | 3 | 2 | 3 | 3 | 1 |
| Soybean | 3 | 3 | 3 | 3 | 6 | 1 | 2 | 4 | 3 | 7 | 1 | 10 | 8 | 4 | 6 | 6 | 2 |
| Sugar beet | 8 | 4 | 6 | 3 | 7 | 2 | 4 | 6 | 3 | 9 | 0 | 10 | 10 | 4 | 6 | 6 | 6 |
| Velvetleaf | 7 | 2 | 4 | 1 | 6 | 1 | 1 | 7 | 5 | 9 | 0 | 10 | 10 | 4 | 5 | 4 | 3 |
| Wheat | 4 | 3 | 4 | 2 | 4 | 1 | 0 | 1 | 2 | 8 | 0 | 8 | 5 | 3 | 4 | 2 | 1 |
| Wild buckwheat | 10 | 7 | 3 | 4 | 4 | 1 | 4 | 2 | 2 | 10 | 0 | 10 | 10 | 2 | 4 | 5 | 2 |
| Wild oat | 3 | 4 | 3 | 3 | 3 | 2 | 0 | 2 | 1 | 6 | 0 | 9 | 3 | 2 | 3 | 1 | 0 |

TABLE B-continued

| Rate 200 g/ha | COMPOUND | | | | | | | | | | | | | | | | | |
|---|---|---|---|---|---|---|---|---|---|---|---|---|---|---|---|---|---|---|
| | 7 | 9 | 15 | 16 | 26 | 27 | 28 | 29 | 30 | 31 | 32 | 33 | 34 | 35 | 36 | 38 | 39 | 42 |
| PREEMERGENCE | | | | | | | | | | | | | | | | | | |
| Barley | 0 | 0 | 0 | 0 | 0 | 0 | 0 | 0 | 0 | 1 | 1 | 0 | 0 | 0 | 0 | 0 | 0 | 0 |
| Barnyardgrass | 0 | 0 | 0 | 0 | 0 | 0 | 4 | 1 | 5 | 3 | 4 | 0 | 0 | 6 | 8 | 0 | 1 | 0 |
| Bedstraw | 0 | 0 | 0 | 0 | 0 | — | 0 | 0 | 3 | 4 | 2 | — | 0 | 8 | 9 | 3 | 3 | 0 |
| Blackgrass | 2 | 0 | 0 | 0 | 0 | 0 | 1 | 0 | 2 | 3 | 4 | 1 | 0 | 3 | 3 | 3 | 1 | 0 |
| Cheatgrass | 0 | 0 | 0 | 0 | 0 | 0 | 1 | 0 | 1 | 0 | 2 | 1 | 0 | 2 | 3 | 2 | 2 | — |
| Chickweed | 0 | 0 | 0 | 0 | 0 | 0 | 0 | 0 | 0 | 1 | 0 | 0 | 0 | 2 | 7 | 3 | 3 | 0 |
| Cocklebur | 0 | 0 | 0 | 0 | 0 | 0 | 0 | 0 | 0 | 0 | 0 | 0 | 0 | 1 | 5 | 3 | 2 | 0 |
| Corn | 0 | 0 | 0 | 0 | 0 | 0 | 0 | 0 | 0 | 0 | 2 | 0 | 0 | 2 | 2 | 0 | 0 | 0 |
| Cotton | 0 | 0 | 0 | 0 | 0 | 0 | 0 | 0 | 0 | 0 | 1 | — | 0 | 0 | 2 | 0 | 0 | 0 |
| Crabgrass | 1 | 0 | 0 | 0 | 0 | 0 | 1 | 2 | 3 | 6 | 4 | 2 | — | 3 | 7 | 2 | 5 | 0 |
| Downy brome | — | — | — | — | — | — | — | — | — | — | — | — | — | — | — | — | — | — |
| Giant foxtail | 0 | 0 | 0 | 0 | 0 | 0 | 1 | 2 | 1 | 2 | 3 | 3 | 0 | 4 | 5 | 0 | 4 | 0 |
| Lambsquarter | 1 | 0 | 0 | 0 | 0 | 0 | 10 | 7 | 9 | 10 | 10 | 9 | 0 | 9 | 10 | 9 | 9 | 7 |
| Morningglory | 0 | 0 | 0 | 0 | 0 | 0 | 0 | 0 | 0 | 0 | 0 | 0 | 0 | 0 | 2 | 2 | 2 | 0 |
| Nutsedge | 0 | 0 | 0 | 0 | 0 | 0 | 0 | 0 | 0 | 0 | 0 | 0 | 0 | 0 | 4 | 2 | 3 | 0 |
| Rape | 2 | 0 | 0 | 0 | 0 | 0 | 2 | 0 | 0 | 8 | 5 | 5 | 0 | 10 | 2 | 0 | 0 | 0 |
| Rice | 0 | 0 | 0 | 0 | 0 | 0 | 1 | 1 | 3 | 3 | 3 | 2 | 0 | 2 | 2 | 0 | 0 | 0 |
| Sorghum | 0 | 0 | 0 | 0 | 0 | 0 | 0 | 0 | 0 | 0 | 1 | 0 | 0 | 0 | 2 | 0 | 0 | 0 |
| Soybean | 0 | 0 | 0 | 0 | 0 | 0 | 6 | 0 | 0 | 2 | 0 | 0 | 0 | 3 | 0 | 0 | 0 | 0 |
| Sugar beet | 2 | 0 | 0 | 0 | 0 | 0 | 6 | 0 | 5 | 6 | 5 | 3 | 1 | 10 | 8 | 2 | 4 | 0 |
| Velvetleaf | 7 | 0 | 0 | 0 | 0 | 0 | 9 | 0 | 9 | 10 | 6 | 4 | 0 | 9 | 5 | 0 | 2 | 0 |
| Wheat | 1 | 0 | 0 | 0 | 0 | 0 | 0 | 0 | 0 | 2 | 1 | 2 | 0 | 3 | 5 | 0 | 0 | 0 |
| Wild buckwheat | 0 | 0 | 0 | 0 | 0 | 0 | 9 | 0 | 4 | 9 | 8 | 3 | 0 | 7 | 3 | 2 | 0 | 0 |
| Wild oat | 0 | 0 | 0 | 0 | 0 | 0 | 0 | 0 | 0 | 1 | 1 | 0 | 0 | 2 | 4 | 3 | 3 | 0 |

| Rate 200 g/ha | COMPOUND | | | | | | | | | | | | | | | | | |
|---|---|---|---|---|---|---|---|---|---|---|---|---|---|---|---|---|---|---|
| | 43 | 44 | 45 | 46 | 47 | 48 | 49 | 50 | 51 | 52 | 53 | 54 | 55 | 56 | 57 | 58 | 59 | 60 |
| PREEMERGENCE | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 |
| Barnyardgrass | 0 | 2 | 0 | 0 | 0 | 2 | 3 | 2 | 4 | 2 | 6 | 2 | 3 | 3 | 4 | 2 | 0 | 0 |
| Bedstraw | 0 | 0 | 0 | 0 | 6 | 0 | 0 | 2 | 7 | 8 | 1 | 5 | 4 | 4 | 4 | 2 | — | 0 |
| Blackgrass | 0 | 0 | 0 | 0 | 0 | 1 | 1 | 0 | 2 | 1 | 0 | 1 | 2 | 1 | 1 | 0 | 0 | 0 |
| Cheatgrass | 0 | 0 | 2 | 0 | 2 | 0 | 0 | 0 | 2 | 0 | 3 | 0 | 1 | 0 | 0 | 0 | 0 | 0 |
| Chickweed | 0 | 0 | 1 | 0 | 0 | 0 | 0 | 0 | 0 | 0 | 0 | 0 | 1 | 0 | 0 | 0 | 0 | 0 |
| Cocklebur | 0 | 2 | 2 | 0 | 1 | 0 | 0 | 2 | 0 | 0 | 0 | 0 | 0 | 1 | 1 | 0 | 0 | 0 |
| Corn | 0 | 2 | 1 | 0 | 0 | 0 | 1 | 0 | 0 | 0 | 0 | 2 | 0 | 0 | 0 | 0 | 0 | 0 |
| Cotton | 0 | 1 | 1 | 0 | 0 | 0 | 0 | 0 | 0 | 0 | 0 | 0 | 0 | — | — | 0 | 0 | 0 |
| Crabgrass | 0 | 2 | 0 | 0 | 3 | 2 | 2 | 7 | 2 | 0 | 2 | 0 | 3 | 4 | 3 | 3 | 8 | 0 |
| Downy brome | — | — | — | — | — | — | — | — | — | — | — | — | — | — | — | — | — | — |
| Giant foxtail | 0 | 3 | 1 | 0 | 0 | 2 | 1 | 4 | 3 | 0 | 2 | 0 | 2 | 3 | 6 | 2 | 6 | 0 |
| Lambsquarter | 0 | 0 | 0 | 8 | 8 | 8 | 9 | 8 | 9 | 9 | 9 | 6 | 7 | 7 | 10 | 10 | 0 | 0 |
| Morningglory | 0 | 2 | 1 | 0 | 0 | 1 | 0 | 1 | 0 | 0 | 1 | 0 | 0 | 3 | 2 | 2 | 0 | 0 |
| Nutsedge | 0 | 0 | 0 | — | 0 | — | 2 | 0 | 0 | 0 | — | 0 | 0 | 0 | 0 | 0 | 0 | 0 |
| Rape | 0 | 0 | 0 | 0 | 2 | 0 | 0 | 0 | 2 | 2 | 0 | 3 | 2 | 0 | 2 | 0 | 2 | 0 |
| Rice | 0 | 2 | 0 | 0 | 3 | 1 | 0 | 0 | 2 | 2 | 0 | 0 | 2 | 2 | 2 | 0 | 1 | 0 |
| Sorghum | 0 | 2 | 0 | 0 | 0 | 0 | 0 | 0 | 2 | 0 | 0 | 0 | 0 | 0 | 0 | 0 | 0 | 0 |
| Soybean | 0 | 6 | 2 | 0 | 0 | 0 | 1 | 0 | 0 | 0 | 0 | 0 | 2 | 0 | 4 | 0 | 0 | 0 |
| Sugar beet | 0 | 0 | 0 | 4 | 8 | 9 | 6 | 4 | 6 | 6 | 9 | 6 | 6 | 6 | 6 | 4 | 3 | 0 |
| Velvetleaf | 0 | 1 | 3 | 0 | 4 | 0 | 9 | 5 | 7 | 5 | 2 | 6 | 4 | 4 | 9 | 6 | 6 | 0 |
| Wheat | 0 | 0 | 2 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | 0 | 0 | 3 | 2 | 0 | 0 | — | 3 | 3 | 3 | 0 | 3 | 0 |
| Wild oat | 0 | 0 | 0 | 0 | 1 | 0 | 1 | 1 | 0 | 1 | 1 | 0 | 1 | 2 | 1 | 0 | 0 | 0 |

| Rate 200 g/ha | COMPOUND | | | | | | | | | | | | | | | | |
|---|---|---|---|---|---|---|---|---|---|---|---|---|---|---|---|---|---|
| | 61 | 63 | 64 | 65 | 66 | 70 | 71 | 72 | 73 | 74 | 75 | 76 | 77 | 78 | 79 | 80 | 81 |
| PREEMERGENCE | | | | | | | | | | | | | | | | | |
| Barley | 0 | 0 | 0 | 0 | 0 | 0 | 1 | 0 | 0 | 0 | 0 | 0 | 0 | 1 | 0 | 0 | 1 |
| Barnyardgrass | 0 | 0 | 0 | 0 | 0 | 0 | 8 | 2 | 0 | 0 | 5 | 7 | 1 | 6 | 0 | 0 | 2 |
| Bedstraw | — | 0 | 3 | — | 4 | 0 | 10 | 10 | 10 | 0 | 0 | 2 | 3 | 7 | 2 | 10 | 10 |
| Blackgrass | 0 | 0 | 0 | 0 | 0 | 0 | 3 | 0 | 0 | 0 | 4 | 2 | 3 | 3 | 2 | 1 | 1 |
| Cheatgrass | 0 | 0 | 0 | 0 | 0 | 0 | 2 | 0 | 0 | 0 | 4 | 4 | 0 | 2 | 0 | 3 | 1 |
| Chickweed | 0 | 0 | 0 | 0 | 0 | 0 | 1 | 0 | 9 | 0 | 1 | 4 | 2 | 2 | 0 | — | 3 |
| Cocklebur | 0 | 0 | 0 | 0 | 0 | 0 | 0 | 0 | 0 | 0 | 0 | 2 | 0 | 4 | 0 | 0 | 2 |
| Corn | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 1 | 10 | 0 | 0 | 0 | 5 | 8 | 4 | 7 | 2 | 2 | 7 |
| Downy brome | — | — | — | — | — | — | — | — | — | — | — | — | — | — | — | — | — |

TABLE B-continued

| | | | | | | | | | | | | | | | | |
|---|---|---|---|---|---|---|---|---|---|---|---|---|---|---|---|---|
| Giant foxtail | 0 | 0 | 0 | 0 | 0 | 1 | 9 | 1 | 0 | 0 | 3 | 5 | 3 | 5 | 1 | 1 | 5 |
| Lambsquarter | 0 | 0 | 0 | 0 | 0 | 0 | 8 | 0 | 0 | 0 | 10 | 9 | 10 | 10 | 6 | 8 | 10 |
| Morningglory | 0 | 0 | 1 | 0 | 0 | 1 | 5 | 0 | 0 | 0 | 5 | 2 | 2 | 5 | 3 | — | 5 |
| Nutsedge | 0 | 0 | 0 | 0 | 0 | 0 | 2 | 1 | 0 | 0 | 2 | 2 | 3 | 3 | 2 | 3 | 0 |
| Rape | 0 | 0 | 0 | 0 | 0 | 0 | 8 | 0 | 0 | 0 | 2 | 3 | 2 | 8 | 0 | 0 | 5 |
| Rice | 0 | 0 | 0 | 0 | 0 | 0 | 6 | 0 | 0 | 0 | 0 | 3 | 1 | 1 | 0 | 0 | 0 |
| Sorghum | 0 | 0 | 0 | 0 | 0 | 0 | 1 | 0 | 0 | 0 | 0 | 0 | 0 | 2 | 0 | 0 | 0 |
| Soybean | 0 | 0 | 0 | 0 | 0 | 0 | 0 | 0 | 0 | 0 | 0 | 0 | 0 | 0 | 0 | 0 | 1 |
| Sugar beet | 0 | 0 | 3 | 0 | 0 | 0 | 10 | 2 | 0 | 0 | 7 | 9 | 7 | 9 | 0 | 1 | 8 |
| Velvetleaf | 0 | 0 | 0 | 0 | 0 | 0 | 10 | 0 | 2 | 0 | 7 | 9 | 10 | 9 | 1 | 3 | 10 |
| Wheat | 0 | 0 | 0 | 0 | 0 | 0 | 5 | 0 | 0 | 0 | 2 | 3 | 2 | 3 | 0 | 0 | 3 |
| Wild buckwheat | 0 | 0 | 0 | 0 | 0 | 0 | 6 | 0 | 0 | 0 | 2 | 9 | 9 | 9 | 0 | 0 | 1 |
| Wild oat | 0 | 0 | 0 | 0 | 0 | 0 | 5 | 0 | 0 | 0 | 3 | 1 | 2 | 2 | 0 | 0 | 2 |

| | COMPOUND | | | | | | | | | | | | | | |
|---|---|---|---|---|---|---|---|---|---|---|---|---|---|---|---|
| Rate 200 g/ha | 82 | 83 | 84 | 85 | 86 | 87 | 88 | 90 | 91 | 92 | 94 | 96 | 97 | 98 | 100 | 110 |
| PREEMERGENCE | | | | | | | | | | | | | | | | |
| Barley | 0 | 0 | 2 | 0 | 1 | 0 | 0 | 0 | 0 | 1 | 3 | 2 | 0 | 0 | 3 | 0 |
| Barnyardgrass | 5 | 4 | 4 | 0 | 5 | 0 | 1 | 0 | 0 | 7 | 9 | 8 | 5 | 2 | 8 | 0 |
| Bedstraw | 10 | 2 | 4 | 0 | 2 | 0 | 2 | 0 | 0 | 8 | 9 | 7 | 1 | 6 | 10 | — |
| Blackgrass | 2 | 1 | 1 | 0 | 1 | 1 | 0 | 0 | 0 | 3 | 8 | 3 | 2 | 0 | 7 | 0 |
| Cheatgrass | 2 | 0 | 1 | 0 | 2 | 0 | 0 | 0 | 0 | 6 | 7 | 2 | 1 | 0 | 9 | — |
| Chickweed | 6 | 1 | 5 | 0 | 4 | 0 | — | 0 | 0 | 9 | 9 | 6 | 9 | 4 | 9 | 0 |
| Cocklebur | 3 | 3 | 3 | 0 | 0 | 2 | 2 | 0 | 2 | 3 | 7 | 0 | 2 | 1 | 4 | 0 |
| Corn | 0 | 0 | 1 | 0 | 0 | 0 | 0 | 1 | 1 | 2 | 7 | 2 | 4 | 0 | 8 | 0 |
| Cotton | 1 | 0 | 4 | 0 | 3 | 0 | 1 | 0 | 0 | 0 | 9 | 0 | 0 | 0 | 9 | 0 |
| Crabgrass | 8 | 5 | 7 | 2 | 8 | 3 | 9 | 2 | 1 | 6 | 10 | 9 | 1 | 2 | 5 | 0 |
| Downy brome | — | — | — | — | — | — | — | — | — | — | — | — | — | — | — | 3 |
| Giant foxtail | 2 | 2 | 3 | 0 | 6 | 3 | 2 | 0 | 1 | 7 | 9 | 9 | 1 | 2 | 6 | 0 |
| Lambsquarter | 9 | 10 | 7 | 0 | 10 | 9 | — | 0 | 0 | 10 | 10 | 10 | 10 | 8 | 10 | 0 |
| Morningglory | 7 | 3 | 3 | 0 | 3 | 3 | 1 | 2 | 1 | 4 | 10 | 6 | 3 | 1 | 10 | 0 |
| Nutsedge | 0 | 0 | 2 | 0 | 3 | 4 | 1 | 0 | 1 | 1 | 2 | 0 | 0 | 0 | 5 | 0 |
| Rape | 1 | 7 | 1 | 0 | 9 | 0 | 0 | 0 | 0 | 6 | 10 | 10 | 1 | — | 9 | 1 |
| Rice | 0 | 0 | 1 | 0 | 2 | 0 | 0 | 0 | 0 | 4 | 7 | 3 | 6 | 5 | 10 | 0 |
| Sorghum | 0 | 0 | 1 | 0 | 0 | 0 | 0 | 0 | 2 | 1 | 3 | 0 | 0 | 0 | 6 | 0 |
| Soybean | 0 | 0 | 0 | 0 | 4 | 0 | 0 | 0 | 0 | 6 | 9 | 0 | 7 | 0 | 7 | 0 |
| Sugar beet | 5 | 10 | 9 | 0 | 8 | 0 | 0 | 0 | 0 | 8 | 10 | 10 | 2 | 9 | 10 | 0 |
| Velvetleaf | 9 | 9 | 9 | 6 | 9 | 1 | 2 | 3 | 0 | 10 | 10 | 10 | 2 | 4 | 10 | 0 |
| Wheat | 2 | 0 | 2 | 0 | 0 | 0 | 0 | 0 | 0 | 3 | 7 | 4 | 2 | 3 | 7 | 2 |
| Wild buckwheat | 7 | 3 | 9 | 0 | 9 | 0 | — | 0 | 0 | 10 | 10 | 7 | 3 | 1 | 10 | 0 |
| Wild oat | 2 | 0 | 2 | 0 | 1 | 0 | 0 | 0 | 0 | 3 | 6 | 4 | 5 | 3 | 7 | 0 |

| | COMPOUND | | | | | | | | |
|---|---|---|---|---|---|---|---|---|---|
| Rate 100 g/ha | 24 | 37 | 101 | 102 | 103 | 104 | 106 | 108 | 109 |
| POSTEMERGENCE | | | | | | | | | |
| Barley | 1 | 6 | 3 | 2 | 0 | 0 | 2 | 2 | 0 |
| Barnyardgrass | 1 | 3 | 2 | 1 | 1 | 2 | 2 | 1 | 1 |
| Bedstraw | 2 | 7 | 5 | 2 | 0 | 0 | 3 | — | — |
| Blackgrass | 0 | 2 | 0 | 1 | 1 | 0 | 2 | 1 | 1 |
| Cheatgrass | 1 | 3 | — | — | — | — | — | — | — |
| Chickweed | 1 | 3 | 3 | 2 | 2 | 0 | 2 | 2 | 2 |
| Cocklebur | 4 | 7 | 3 | 2 | 1 | 1 | 4 | 3 | 1 |
| Corn | 1 | 3 | 1 | 1 | 1 | 1 | 2 | 1 | 1 |
| Cotton | 9 | 9 | 9 | 7 | 3 | 2 | 9 | 10 | 9 |
| Crabgrass | 1 | 5 | 2 | 1 | 1 | 2 | 3 | 1 | 1 |
| Downy brome | — | — | 0 | 1 | 0 | 0 | 2 | 0 | 0 |
| Giant foxtail | 1 | 4 | 2 | 2 | 1 | 1 | 3 | 1 | 1 |
| Lambsquarter | 3 | 8 | 2 | 2 | 2 | 2 | — | 7 | 3 |
| Morningglory | 5 | 8 | 8 | 2 | 0 | 2 | 10 | 5 | 3 |
| Nutsedge | 1 | 3 | 1 | 0 | — | — | 2 | 2 | 0 |
| Rape | 2 | 5 | 5 | 5 | 2 | 1 | 2 | 2 | 3 |
| Rice | 2 | 5 | 3 | 2 | 0 | 0 | 3 | 3 | 1 |
| Sorghum | 2 | 4 | 1 | 1 | 1 | 1 | 4 | 1 | 1 |
| Soybean | 2 | 6 | 4 | 3 | 2 | 3 | 4 | 4 | 2 |
| Sugar beet | 2 | 7 | 6 | 6 | 3 | 3 | 6 | 8 | 5 |
| Velvetleaf | 2 | 8 | 3 | 1 | 0 | 3 | 5 | 1 | 2 |
| Wheat | 1 | 2 | 3 | 1 | 1 | 1 | 2 | 0 | 0 |
| Wild buckwheat | 2 | 7 | 5 | 3 | 3 | 2 | 3 | 4 | 2 |
| Wild oat | 1 | 2 | 0 | 2 | 1 | 1 | 3 | 0 | 0 |

TABLE B-continued

| Rate 100 g/ha | COMPOUND | | | | | | | | |
|---|---|---|---|---|---|---|---|---|---|
| | 24 | 37 | 101 | 102 | 103 | 104 | 106 | 108 | 109 |
| PREEMERGENCE | | | | | | | | | |
| Barley | 0 | 0 | 0 | 0 | 0 | 0 | 3 | 0 | 0 |
| Barnyardgrass | 0 | 1 | 0 | 0 | 0 | 0 | 8 | 0 | 0 |
| Bedstraw | 0 | 0 | 1 | 0 | 4 | 0 | 10 | — | 0 |
| Blackgrass | 0 | 1 | 0 | 0 | 3 | 0 | 4 | 2 | 0 |
| Cheatgrass | 0 | 1 | — | — | — | — | — | — | — |
| Chickweed | 0 | 1 | 0 | 0 | 2 | 0 | 9 | 0 | 0 |
| Cocklebur | 0 | 0 | 0 | 0 | 0 | 0 | 7 | 0 | 0 |
| Corn | 0 | 0 | 0 | 0 | 0 | 0 | 8 | 0 | 0 |
| Cotton | 0 | 0 | 0 | 0 | 0 | 0 | 2 | 0 | 0 |
| Crabgrass | 0 | 1 | 0 | 0 | 0 | 0 | 8 | 0 | 0 |
| Downy brome | — | — | 1 | 1 | 0 | 0 | 3 | 0 | 0 |
| Giant foxtail | 0 | 1 | 0 | 0 | 0 | 0 | 9 | 0 | 0 |
| Lambsquarter | 0 | 8 | 1 | 0 | 8 | 1 | 10 | 5 | 2 |
| Morningglory | 0 | 0 | 0 | 0 | 0 | 0 | 7 | 0 | 0 |
| Nutsedge | — | 2 | 0 | 0 | — | 0 | 5 | 0 | 0 |
| Rape | 0 | 0 | 0 | 0 | 4 | 3 | 10 | 0 | 1 |
| Rice | 0 | 1 | 0 | 0 | 0 | 0 | 6 | 0 | 0 |
| Sorghum | 0 | 0 | 0 | 0 | 0 | 0 | 5 | 0 | 0 |
| Soybean | 0 | 0 | 0 | 0 | 0 | 0 | 7 | 0 | 0 |
| Sugar beet | 0 | 4 | 1 | 1 | 3 | 2 | 9 | 3 | 1 |
| Velvetleaf | 0 | 7 | 0 | 0 | 0 | 0 | 9 | 0 | 0 |
| Wheat | 0 | 2 | 0 | 0 | 0 | 0 | 4 | 0 | 0 |
| Wild buckwheat | 0 | 0 | 0 | 0 | 6 | 0 | 10 | 2 | 1 |
| Wild oat | 0 | 0 | 0 | 0 | 0 | 0 | 6 | 0 | 0 |

| Rate 50 g/ha | COMPOUND | | | | Rate 50 g/ha | COMPOUND | | | |
|---|---|---|---|---|---|---|---|---|---|
| | 9 | 94 | 96 | 110 | | 9 | 94 | 96 | 110 |
| POSTEMERGENCE | | | | | PREEMERGENCE | | | | |
| Barley | 0 | 4 | 2 | 0 | Barley | 0 | 0 | 0 | 0 |
| Barnyardgrass | 1 | 7 | 3 | 1 | Barnyardgrass | 0 | 6 | 1 | 0 |
| Bedstraw | 0 | 8 | 6 | — | Bedstraw | 0 | 5 | 2 | 0 |
| Blackgrass | 0 | 6 | 3 | 0 | Blackgrass | 0 | 6 | 3 | 0 |
| Cheatgrass | 0 | 5 | 3 | — | Cheatgrass | 0 | 4 | 2 | — |
| Chickweed | 0 | 4 | 5 | 1 | Chickweed | 0 | 9 | 2 | 0 |
| Cocklebur | 0 | 8 | — | 0 | Cocklebur | 0 | 0 | 0 | 0 |
| Corn | 1 | 3 | 2 | 0 | Corn | 0 | 2 | 0 | 0 |
| Cotton | 1 | 10 | 9 | 2 | Cotton | 0 | 0 | 0 | 0 |
| Crabgrass | 1 | 5 | 3 | 1 | Crabgrass | 0 | 6 | 2 | 0 |
| Downy brome | — | — | — | 0 | Downy brome | — | — | — | 0 |
| Giant foxtail | 1 | 5 | 4 | 1 | Giant foxtail | 0 | 3 | 0 | 0 |
| Lambsquarter | 0 | 10 | 5 | 1 | Lambsquarter | 0 | 10 | 10 | 0 |
| Morningglory | 0 | 8 | 6 | 2 | Morningglory | 0 | 2 | 0 | 0 |
| Nutsedge | 0 | — | — | 0 | Nutsedge | 0 | 0 | 0 | 0 |
| Rape | 0 | 9 | 7 | 0 | Rape | 0 | 6 | 3 | 0 |
| Rice | 1 | 7 | 5 | 0 | Rice | 0 | 3 | 0 | 0 |
| Sorghum | 0 | 4 | 3 | 0 | Sorghum | 0 | 1 | 0 | 0 |
| Soybean | 0 | 7 | 3 | 0 | Soybean | 0 | 4 | 0 | 0 |
| Sugar beet | 0 | 10 | 9 | 3 | Sugar beet | 0 | 9 | 7 | 0 |
| Velvetleaf | 0 | 10 | 9 | 0 | Velvetleaf | 0 | 10 | 9 | 0 |
| Wheat | 0 | 5 | 3 | 0 | Wheat | 0 | 1 | 1 | 0 |
| Wild buckwheat | 0 | 10 | 10 | 0 | Wild buckwheat | 0 | 9 | 3 | 0 |
| Wild oat | 0 | 3 | 2 | 0 | Wild oat | 0 | 3 | 1 | 0 |

TEST C

The compounds evaluated in this test were formulated in a non-phytoxic solvent and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgare*), bedstraw (*Galium aparine*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), giant foxtail (*Setaria faberi*), johnsongrass (*Sorghum halepense*), lambsquarters (*Chenopodium album*), morningglory (*Ipomoea hederacea*), pigweed (*Amaranthus retroflexus*), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza saliva*), umbrella sedge (*Cyperus difformis*), duck salad (*Heteranthera limosa*), barnyardgrass (*Echinochloa crus-galli*) and watergrass grown to the 1 and 2 leaf stage for testing.

All plant species were grown using normal greenhouse practices. Visual evaluations of injury expressed on treated plants, when compared to untreated controls, were recorded approximately fourteen to twenty one days after application of the test compound. Plant response ratings, summarized in Table C, were recorded on a 0 to 100 scale where 0 is no effect and 100 is complete control. A dash (–) response means no test result.

TABLE C

| Rate 500 g/ha | COMPOUND 100 | Rate 250 g/ha | COMPOUND 100 | |
| --- | --- | --- | --- | --- |
| POSTEMERGENCE | | POSTEMERGENCE | | |
| Barnyardgrass 2 | 0 | Barnyardgrass 2 | 0 | |
| Duck salad | 0 | Duck salad | 0 | |
| Watergrass 2 | 20 | Watergrass 2 | 0 | |
| Rice Japonica | 30 | Rice Japonica | 0 | |
| Umbrella sedge | 0 | Umbrella sedge | 0 | |
| Rate 500 g/ha | COMPOUND 100 | Rate 250 g/ha | COMPOUND 100 | |
| PREEMERGENCE | | PREEMERGENCE | | |
| Barley Igri | 85 | Barley Igri | 0 | 65 |
| Barnyardgrass | 100 | Barnyardgrass | — | 95 |
| Blackgrass | 95 | Blackgrass | 30 | — |
| Cotton | 100 | Cotton | 10 | 100 |
| Crabgrass | 100 | Crabgrass | 40 | 100 |
| Downy Brome | 100 | Downy Brome | — | 85 |
| Galium | 100 | Galium | 0 | 100 |
| Giant foxtail | 100 | Giant foxtail | 70 | 100 |
| Ryegrass | 100 | RYegrass | 0 | 95 |
| Johnsongrass | 100 | Johnsongrass | — | 100 |
| Lambsquarters | 100 | Lambsquarters | 100 | 100 |
| Morningglory | 100 | Morningglory | 10 | 100 |
| Rape | 100 | Rape | 10 | 100 |
| Redroot Pigweed | 100 | Redroot Pigweed | 100 | 100 |
| Sorghum | — | Sorghum | 40 | — |
| Soybean | 95 | Soybean | 0 | 90 |
| Sugar beet | 100 | Sugar beet | 90 | 100 |
| Velvetleaf | 100 | Velvetleaf | 100 | 100 |
| Speedwell | 100 | Speedwell | 100 | 100 |
| Wheat | 100 | Wheat | 0 | 80 |
| Wild buckwheat | 100 | Wild buckwheat | 100 | 100 |
| Wild oat | 95 | Wild oat | 20 | 95 |
| Rate 125 g/ha | COMPOUND 100 | Rate 62 g/ha | COMPOUND 6 | 100 |
| POSTEMERGENCE | | POSTMERGENCE | | |
| Barnyardgrass 2 | 0 | Barley Igri | 0 | 25 |
| Duck salad | 0 | Barnyardgrass | — | 80 |
| Watergrass 2 | 0 | Blackgrass | 0 | 35 |
| Rice Japonica | 0 | Chickweed | 0 | 65 |
| Umbrella sedge | 0 | Cocklebur | — | 40 |
| | | Corn | 0 | 70 |
| Rate 125 g/ha | COMPOUND 6 100 | Cotton | 0 | 55 |
| | | Crabgrass | 0 | 75 |
| PREEMERGENCE | | Downy Brome | 0 | 30 |
| Barley Igri | 0 40 | Galium | 0 | 100 |
| Barnyardgrass | — — | Giant foxtail | 0 | 90 |
| Blackgrass | 20 65 | Ryegrass | 0 | 55 |
| Chickweed | 0 65 | Johnsongrass | — | 95 |
| Cocklebur | — 45 | Lambscluarters | 100 | 100 |
| Corn | 0 70 | Morningglory | 0 | 70 |
| Cotton | 0 55 | Rape | 0 | 80 |
| Crabgrass | 0 95 | Redroot Pigweed | 60 | 100 |
| Downy Brome | 0 65 | Sorghum | 0 | — |
| Galium | 0 100 | Soybean | 0 | 70 |
| Giant foxtail | 0 100 | Sugar beet | 0 | 90 |

TABLE C-continued

| | | | | | |
|---|---|---|---|---|---|
| Ryegrass | 0 | 75 | Velvetleaf | 0 | 100 |
| Johnsongrass | — | 100 | Speedwell | 100 | 100 |
| Lambsquarters | 100 | 100 | Wheat | 0 | 30 |
| Morningglory | 0 | 75 | Wild buckwheat | 100 | 100 |
| Rape | 0 | 100 | Wild oat | 0 | 70 |
| Redroot Pigweed | 100 | 100 | | | |
| Sorghum | 10 | — | | | |
| Soybean | 0 | — | | | |
| Sugar beet | 20 | 100 | | | |
| Velvetleaf | 20 | 100 | | | |
| Speedwell | 100 | 100 | | | |
| Wheat | 0 | 65 | | | |
| Wild buckwheat | 100 | 100 | | | |
| Wild oat | 0 | 75 | | | |
| Rate 31 g/ha | | COMPOUND 6 | | | |

| PREEMERGENCE | | | | |
|---|---|---|---|---|
| Barley Igri | 0 | Ryegrass | 0 | |
| Barnyardgrass | — | Johnsongrass | — | |
| Blackgrass | 0 | Lambsquarters | 50 | |
| Chickweed | 0 | Morningglory | 0 | |
| Cocklebur | — | Rape | 0 | |
| Corn | 0 | Redroot Pigweed | 0 | |
| Cotton | 0 | Sorghum | 0 | |
| Crabgrass | 0 | Soybean | 0 | |
| Downy Brome | 0 | Sugar beet | 0 | |
| Galium | 0 | Velvetleaf | 0 | |
| Giant foxtail | 0 | Speedwell | 90 | |
| | | Wheat | 0 | |
| | | Wild buckwheat | 0 | |
| | | Wild oat | 0 | |

TEST D

Compounds evaluated in this test were formulated in a non-phytoxic solvent and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include winter barley (*Hordeum vulgare* cv. 'Igri'), chickweed (*Stellaria media*), downy brome (*Bromus tectorum*), field violet (*Viola arvensis*), galium (*Galium aparine*), kochia (*Kochia scoparia*), lambsquarters (*Chenopodium album*), speedwell (*Veronica persica*), rape (*Brassica napus*), sugar beet (*Beta vulgaris* cv. 'US1'), sunflower (*Helianthus annuus* cv. 'Russian Giant'), spring wheat (*Triticum aestivum* cv. 'ERA'), winter wheat (*Triticum aestivum* cv. 'Talent'), wild buckwheat (*Polygonum convolvulus*), wild mustard (*Sinapis arvensis*), and wild radish (*Raphanus raphanistrum*).

Galium was treated at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table D, are based upon a 0 to 100 scale where 0 is no effect and 100 is complete control. A dash response (–) means no test result.

TABLE D

| Rate 250 g/ha | COMPOUND 6 | Rate 125 g/ha | COMPOUND 6 |
|---|---|---|---|
| PREEMERGENCE | | PREEMERGENCE | |
| Chickweed | 0 | Chickweed | 0 |
| Field violet | 0 | Field violet | 0 |
| Galium (1) | 0 | Galium (1) | 0 |
| Galium (2) | 0 | Galium (2) | 0 |
| Kochia | 0 | Kochia | 0 |
| Lambsquarters | — | Lambsquarters | 0 |
| Speedwell | — | Speedwell | 100 |
| Rape | 0 | Rape | 0 |

TABLE D-continued

| | | | |
|---|---|---|---|
| Sugar beet | 80 | Sugar beet | 20 |
| Sunflower | 0 | Sunflower | 0 |
| Wheat (Spring) | 0 | Wheat (Spring) | 0 |
| Wheat (Winter) | 0 | Wheat (Winter) | 0 |
| Wild buckwheat | 0 | Wild buckwheat | 0 |
| Wild mustard | 60 | Wild mustard | 0 |
| Wild radish | 0 | Wild radish | 0 |
| Winter Barley | 0 | Winter Barley | 0 |

| | COMPOUND | | COMPOUND |
|---|---|---|---|
| Rate 62 g/ha | 6 | Rate 31 g/ha | 6 |
| PREEMERGENCE | | PREEMERGENCE | |
| Chickweed | 0 | Chickweed | 0 |
| Field violet | 0 | Field violet | 0 |
| Galium (1) | 0 | Galium (1) | 0 |
| Galium (2) | 0 | Galium (2) | 0 |
| Kochia | 0 | Kochia | 0 |
| Lambsquarters | — | Lambsquarters | — |
| Speedwell | 100 | Speedwell | 100 |
| Rape | 0 | Rape | 0 |
| Sugar beet | 20 | Sugar beet | 0 |
| Sunflower | 0 | Sunflower | 0 |
| Wheat (Spring) | 0 | Wheat (Spring) | 0 |
| Wheat (Winter) | 0 | Wheat (Winter) | 0 |
| Wild buckwheat | 0 | Wild buckwheat | 0 |
| Wild mustard | 0 | Wild mustard | 0 |
| Wild radish | 0 | Wild radish | 0 |
| Winter Barley | 0 | Winter Barley | 0 |

What is claimed is:

1. A compound of Formula I

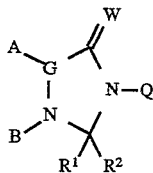

I wherein

Q is

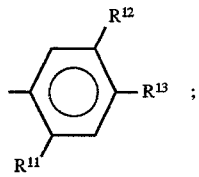

Q-1

$R^1$ is H; $C_1$–$C_4$ alkyl, $C_1$–$C_4$ haloalkyl; or halogen;

$R^2$ is $C_1$–$C_2$ alkyl optionally substituted with one or more halogens, $OR^8$, CN, $COR^9$, $CO_2R^{31}$ or $CONR^{32}R^{33}$; CN; $CO_2R^{34}$; $CONR^{35}R^{36}$; $S(O)_nR^8$; $S(O)_nNR^{19}R^8$ or $COR^{37}$; or $R^1$ and $R^2$ can be taken together along with the carbon to which they are attached to form C=CHCO$_2R^{31}$; C=C(CH$_3$)CO$_2R^{31}$; C=C(C$_2$H$_5$)CO$_2R^{31}$; C=CHCONR$^{32}R^{33}$; C=C(CH$_3$)CONR$^{32}R^{33}$ or C=C(C$_2$H$_5$)CONR$^{32}R^{33}$;

G is CH or C($C_1$–$C_4$ alkyl);

A is $C_1$–$C_4$ alkyl; $C_1$–$C_4$ haloalkyl; $C_2$–$C_4$ alkenyl; $C_2$–$C_4$ alkynyl; $OR^{10}$; $SR^{10}$ or halogen;

B is $C_1$–$C_4$ alkyl; $C_1$–$C_4$ haloalkyl; $C_3$–$C_4$ alkenyl or $C_3$–$C_4$ alkynyl;

A and B can be taken together as Selected from the group consisting of $CHR^7CHR^6CHR^3$, $CHR^7CHR^6CHR^4CHR^5$, $CHR^7OCHR^4CHR^5$, $CHR^7SCHR^4CHR^5$, $CHR^7S(O)_2CHR^4CHR^5$, $CHR^7NR^{38}CHR^4CHR^5$, $CHR^4$-$CHR^5NR^{38}CHR^3$, $CHR^7CR^6$=$CR^6CHR^3$, $CHR^4CHR^5S(O)_2CHR^4CHR^5$ and $CHR^7S(O)_2CHR^3$, and the directionality of the linkage is defined such that the moiety depicted on the left side of the linkage is bonded to G and the moiety depicted on the right side of the linkage is bonded to nitrogen;

n is independently 0; 1 or 2;

$R^3$, $R^4$, $R^5$, $R^6$ and $R^7$ are independently H; halogen; $C_1$–$C_4$ alkyl or $C_1$–$C_4$ haloalkyl;

$R^3$ and $R^6$, or $R^6$ and $R^7$, can be taken together to form —$CH_2$—;

$R^8$ and $R^9$ are independently H; $C_1$–$C_6$ alkyl; $C_2$–$C_6$ alkenyl; $C_3$–$C_6$ cycloalkyl or phenyl optionally substititued with one or more $CH_3$, $OCH_3$, $NO_2$, CN or halogens;

W is independently O or S;

$R^{10}$ is $C_1$–$C_4$ alkyl or $C_1$–$C_4$ haloalkyl;

$R^{11}$ is halogen;

$R^{12}$ is H; $C_1$–$C_8$ alkyl; $C_1$–$C_8$ haloalkyl; halogen; OH; $OR^{17}$; SH; $S(O)_nR^{17}$; $COR^{17}$; $CO_2R^{17}$; $C(O)SR^{17}$; $C(O)NR^{19}R^{20}$; CHO; $CR^{19}$=$NOR^{26}$; CH=$CR^{27}CO_2R^{17}$; $CH_2CHR^{27}CO_2R^{17}$; $CO_2N$=$CR^{21}R^{22}$; $NO_2$; CN; $NHSO_2R^{23}$; $NHSO_2NHR^{23}$; $NR^{17}R^{28}$; $NH_2$ or phenyl optionally substituted with $R^{29}$;

$R^{13}$ is $C_1$–$C_2$ alkyl; $C_1$–$C_2$ haloalkyl; $OCH_3$; $SCH_3$; $OCHF_2$; halogen; CN or $NO_2$;

$R^{17}$ is $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_4$–$C_8$ alkoxyalkoxyalkyl; $C_4$–$C_8$ cycloalkylalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; C$_4$–C$_8$ haloalkenyloxyalkyl; C$_4$–C$_8$haloalkynyloxyalkyl; C$_6$–C$_8$ cycloalkylthioalkyl; C$_4$–C$_8$ alkenylthioalkyl; C$_4$–C$_8$ alkynylthioalkyl; C$_1$–C$_4$ alkyl substituted with phenoxy or benzyloxy, each ring optionally substituted with halogen, C$_1$–C$_3$ alkyl or C$_1$–C$_3$haloalkyl; C$_4$–C$_8$ trialkylsilylalkyl; C$_3$–C$_8$ cyanoalkyl; C$_3$–C$_8$ halocycloalkyl; C$_3$–C$_8$ haloalkenyl; C$_5$–C$_8$ alkoxyalkenyl; C$_5$–C$_8$ haloalkoxyalkenyl; C$_5$–C$_8$ alkylthioalkenyl; C$_3$–C$_8$ haloalkynyl; C$_5$–C$_8$ alkoxyalkynyl; C$_5$–C$_8$ haloalkoxyalkynyl; C$_5$–C$_8$ alkylthioalkynyl; C$_2$–C$_8$ alkyl carbonyl; benzyl optionally substituted with halogen, C$_1$–C$_3$ alkyl or C$_1$–C$_3$ haloalkyl; CHR$^{24}$COR$^{18}$; CHR$^{24}$p(O)(OR$^{18}$)$_2$; CHR$^{24}$P(S)(OR$^{18}$)$_2$; CHR$^{24}$C(O)NR$^{19}$R$^{20}$; CHR$^{24}$C(O)NH$_2$; CHR$^{24}$CO$_2$R$^{18}$; CO$_2$R$^{18}$;SO$_2$R$^{18}$; phenyl optionally substituted with R$^{29}$;

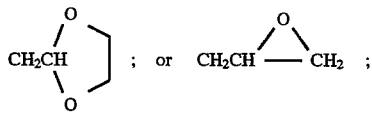

R$^{18}$ is C$_1$–C$_6$ alkyl; C$_1$–C$_6$ haloalkyl; C$_3$–C$_6$ alkenyl or C$_3$–C$_6$ alkynyl;

R$^{19}$ and R$^{21}$ are independently H or C$_1$–C$_4$ alkyl;

R$^{20}$ and R$^{22}$ are independently C$_1$–C$_4$ alkyl or phenyl optionally substituted with halogen, C$_1$–C$_3$ alkyl or C$_1$–C$_3$ haloalkyl;

R$^{19}$ and R$^{20}$ may be taken together along with the nitrogen to which they are attached to form a piperidinyl, pyrrolidinyl or morpholinyl ring, each ring optionally substituted with C$_1$–C$_3$ alkyl, phenyl or benzyl;

R$^{21}$ and R$^{22}$ may be taken together with the carbon to which they are attached to form C$_3$–C$_8$ cycloalkyl;

R$^{23}$ is C$_1$–C$_4$ alkyl or C$_1$–C$_4$ haloalkyl;

R$^{24}$ is H or C$_1$–C$_4$ alkyl;

R$^{26}$ is H, C$_1$–C$_6$ alkyl, C$_3$–C$_6$ alkenyl or C$_3$–C$_6$ alkynyl;

R$^{27}$ is H, C$_1$–C$_4$ alkyl or halogen;

R$^{28}$ is H or C$_1$–C$_4$ alkyl; and

R$^{29}$ is C$_1$–C$_2$ alkyl; C$_1$–C$_2$haloalkyl; OCH$_3$; SCH$_3$; OCHF$_2$; halogen; CN or NO$_2$;

R$^{31}$, R$^{32}$, R$^{33}$, R$^{34}$, R$^{35}$, R$^{36}$ and R$^{37}$ are independently H; C$_1$–C$_6$ alkyl; C$_2$–C$_6$ alkenyl; C$_3$–C$_6$ alkynyl; C$_3$–C$_6$ cycloalkyl; or benzyl or phenyl each optionally substituted on the phenyl ring with one or more CH$_3$, OCH$_3$, NO$_2$, CN or halogen;

R$^{38}$ is H; C$_1$–C$_4$ alkyl or C$_1$–C$_4$ haloalkyl; and their corresponding N-oxides and agriculturally suitable salts provided that when R$^2$ is methyl or ethyl, then A and B are taken together as selected from CHR$^7$CHR$^6$CHR$^3$, CHR$^7$CHR$^6$CHR$^4$CHR$^5$, CHR$^7$OCHR$^4$CHR$^5$, CHR$^7$SCHR$^4$CHR$^5$, CHR$^7$S(O)$_2$CHR$^4$CHR$^5$, CHR$^7$NR$^{38}$CHR$^4$CHR$^5$, CHR$^4$CHR$^5$NR$^{38}$CHR$^3$, CHR$^7$CR$^6$=CR$^6$CHR$^3$, CHR$^4$CHR$^5$S(O)$_2$CHR$^4$CHR$^5$ and CHR$^7$S(O)$_2$CHR$^3$, and the directionality of the linkage is defined such that the moiety depicted on the left side of the linkage is bonded to G and the moiety depicted on the right side of the linkage is bonded to nitrogen.

2. A compound of claim 1 wherein:

A and B are taken together as selected from CHR$^7$CHR$^6$CHR$^3$, CHR$^7$CHR$^6$CHR$^4$CHR$^5$ and CHR$^7$OCHR$^4$CHR$^5$, and the directionality of the linkage is defined such that the moiety depicted on the left side of the linkage is bonded to G and the moiety depicted on the right side of the linkage is bonded to nitrogen;

R$^{12}$ is H; C$_1$–C$_8$ alkyl; C$_1$–C$_8$ haloalkyl; halogen; OH; OR$^{17}$; SH; S(O)$_n$R$^{17}$; COR$^{17}$; CO$_2$R$^{17}$; C(O)SR$^{17}$; C(O)NR$^{19}$R$^{20}$; CHO; CH=CHCO$_2$R$^{17}$; CO$_2$N=CR$^{21}$R$^{22}$; NO$_2$; CN; NHSO$_2$R$^{23}$; or NHSO$_2$NHR$^{23}$; and R$^3$, R$^4$, R$^5$, R$^6$ and R$^7$ are independently H; halogen; CF$_3$ or C$_1$–C$_4$ alkyl; provided that only one of R$^3$, R$^4$, R$^5$, R$^6$ and R$^7$ is other than hydrogen; or R$^3$ and R$^6$, or R$^6$ and R$^7$, can be taken together to form —CH$_2$—.

3. A herbicidal composition comprising a herbicidally effective mount of a compound according to claim 1 and at least one of the following: surfactant, solid or liquid diluent.

4. A method for controlling undesired vegetation comprising contacting the vegetation or its environment with a herbicidally effective mount of a compound according to claim 1.

5. A method for controlling undesired vegetation comprising contacting the vegetation or its environment with a herbicidally effective mount of a composition of claim 3.

* * * * *